United States Patent
Koblish et al.

(10) Patent No.: US 11,278,541 B2
(45) Date of Patent: *Mar. 22, 2022

(54) LOW DOSE COMBINATION THERAPY FOR TREATMENT OF MYELOPROLIFERATIVE NEOPLASMS

(71) Applicants: Incyte Corporation, Wilmington, DE (US); H. Lee Moffitt Cancer Center and Research Institute, Inc., Tampa, FL (US)

(72) Inventors: Holly Koblish, Exton, PA (US); Gary Reuther, Tampa, FL (US)

(73) Assignees: Incyte Corporation, Wilmington, DE (US); H. Lee Moffitt Cancer Center and Research Institute, Inc., Tampa, FL (US)

( * ) Notice: Subject to any disclaimer, the term of this patent is extended or adjusted under 35 U.S.C. 154(b) by 108 days.

This patent is subject to a terminal disclaimer.

(21) Appl. No.: 16/783,663

(22) Filed: Feb. 6, 2020

(65) Prior Publication Data

US 2020/0179364 A1 Jun. 11, 2020

Related U.S. Application Data

(63) Continuation of application No. 16/213,550, filed on Dec. 7, 2018, now Pat. No. 10,596,161.

(60) Provisional application No. 62/596,553, filed on Dec. 8, 2017.

(51) Int. Cl.
| | | |
|---|---|---|
| *A61K 31/4545* | (2006.01) | |
| *A61P 35/00* | (2006.01) | |
| *A61K 31/519* | (2006.01) | |
| *A61K 31/4709* | (2006.01) | |

(52) U.S. Cl.
CPC ...... *A61K 31/4545* (2013.01); *A61K 31/4709* (2013.01); *A61K 31/519* (2013.01); *A61P 35/00* (2018.01)

(58) Field of Classification Search
CPC .... A61K 31/4545; A61K 31/519; A61P 35/00
See application file for complete search history.

(56) References Cited

U.S. PATENT DOCUMENTS

| | | |
|---|---|---|
| 2,985,589 A | 5/1961 | Broughton et al. |
| 3,832,460 A | 8/1974 | Kosti |
| 4,140,755 A | 2/1979 | Sheth |
| 4,402,832 A | 9/1983 | Gerhold |
| 4,498,991 A | 2/1985 | Oroskar |
| 4,512,984 A | 4/1985 | Seufert et al. |
| 4,548,990 A | 10/1985 | Mueller et al. |
| 4,814,477 A | 3/1989 | Wijnberg et al. |
| 5,378,700 A | 1/1995 | Sakuma et al. |
| 5,472,949 A | 12/1995 | Arasaki |
| 5,510,101 A | 4/1996 | Stroppolo |
| 5,521,184 A | 5/1996 | Zimmermann |
| 5,630,943 A | 5/1997 | Grill |
| 5,795,909 A | 8/1998 | Shashoua et al. |
| 5,856,326 A | 1/1999 | Anthony |
| 5,919,779 A | 7/1999 | Proudfoot et al. |
| 6,025,366 A | 2/2000 | Walsh et al. |
| 6,060,038 A | 5/2000 | Burns |
| 6,075,056 A | 6/2000 | Quigley, Jr. et al. |
| 6,136,198 A | 10/2000 | Adam et al. |
| 6,217,895 B1 | 4/2001 | Guo et al. |
| 6,335,342 B1 | 1/2002 | Longo et al. |
| 6,375,839 B1 | 4/2002 | Adam et al. |
| 6,413,419 B1 | 7/2002 | Adam et al. |
| 6,486,322 B1 | 11/2002 | Longo et al. |
| 6,518,265 B1 | 2/2003 | Kato et al. |
| 6,548,078 B2 | 4/2003 | Guo |
| 6,569,443 B1 | 5/2003 | Dawson |
| 6,579,882 B2 | 6/2003 | Stewart et al. |
| 6,624,138 B1 | 9/2003 | Sung et al. |
| 6,635,762 B1 | 10/2003 | Blumenkopf et al. |
| 6,712,973 B2 | 3/2004 | Adam et al. |
| 6,713,089 B1 | 3/2004 | Bertelsen et al. |
| 6,852,727 B2 | 2/2005 | Goulet et al. |
| 6,953,776 B2 | 10/2005 | Di Napoli |
| 6,987,116 B2 | 1/2006 | Boschelli et al. |
| 7,005,436 B2 | 2/2006 | Lloyd et al. |
| 7,167,750 B2 | 1/2007 | Knudson et al. |
| 7,265,108 B2 | 9/2007 | Ozaki |
| 7,335,667 B2 | 2/2008 | Rodgers et al. |
| 7,358,255 B2 | 4/2008 | Nakamura |

(Continued)

FOREIGN PATENT DOCUMENTS

| | | |
|---|---|---|
| CN | 101568527 | 10/2009 |
| CN | 102026999 | 4/2011 |

(Continued)

OTHER PUBLICATIONS

International Preliminary Report on Patentability in International Application No. PCT/US2018/064534, dated Jun. 9, 2020, 7 pages.
26th Annual JPMorgan Healthcare Conference presentation dated Jan. 8, 2008, 28 pages.
Abe et al., "Effective Methods for Introducing Some Aryl and Heteroaryl Substituent onto 1-Azaazulene Nuclei," Heterocycles, 2005, 66: 229-240.
Abelson et al., "Alternate reference values for tear film break-up time in normal and dry eye populations, Lacrimal Gland, Tear Film, and Dry Eye Syndromes 3 Part B," Adv Exp Med Biol, 2002, 506: 1121-1125.

(Continued)

*Primary Examiner* — Noble E Jarrell
(74) *Attorney, Agent, or Firm* — Fish & Richardson P.C.

(57) ABSTRACT

The present application relates to treatment of myeloproliferative neoplasms using the JAK1/JAK2 inhibitor, ruxolitinib, in combination with a low dose of a Pim inhibitor, N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, wherein the combination is unexpectedly synergistic at a very low dose of the Pim inhibitor.

36 Claims, 7 Drawing Sheets

(56) References Cited

U.S. PATENT DOCUMENTS

| | | |
|---|---|---|
| 7,517,870 B2 | 4/2009 | Auricchio |
| 7,598,257 B2 | 10/2009 | Rodgers et al. |
| 7,683,171 B2 | 3/2010 | Pitts et al. |
| 7,745,437 B2 | 6/2010 | Ren et al. |
| 7,750,007 B2 | 7/2010 | Bearss et al. |
| 7,834,022 B2 | 11/2010 | Rodgers et al. |
| 8,053,433 B2 | 11/2011 | Rodgers et al. |
| 8,158,616 B2 | 4/2012 | Rodgers et al. |
| 8,168,794 B2 | 5/2012 | Burger et al. |
| 8,309,718 B2 | 11/2012 | Li et al. |
| 8,329,732 B2 | 12/2012 | Burger et al. |
| 8,410,265 B2 | 4/2013 | Zhou et al. |
| 8,415,362 B2 | 4/2013 | Rodgers et al. |
| 8,420,629 B2 | 4/2013 | Rodgers et al. |
| 8,440,679 B2 | 5/2013 | McAllister |
| 8,445,488 B2 | 5/2013 | Rodger et al. |
| 8,486,902 B2 | 7/2013 | Rodgers et al. |
| 8,513,270 B2 | 8/2013 | Arvanitis et al. |
| 8,530,485 B2 | 9/2013 | Rodgers et al. |
| 8,541,425 B2 | 9/2013 | Rodgers et al. |
| 8,563,541 B2 | 10/2013 | Arvanitis et al. |
| 8,604,043 B2 | 12/2013 | Li et al. |
| 8,637,529 B2 | 1/2014 | Woller |
| 8,691,807 B2 | 4/2014 | Yao et al. |
| 8,716,303 B2 | 5/2014 | Rodgers et al. |
| 8,722,693 B2 | 5/2014 | Rodgers et al. |
| 8,741,895 B2 | 6/2014 | Rodgers et al. |
| 8,748,401 B2 | 6/2014 | Rodgers et al. |
| 8,765,734 B2 | 7/2014 | Huang et al. |
| 8,822,481 B1 | 9/2014 | Rodgers et al. |
| 8,829,013 B1 | 9/2014 | Rodgers et al. |
| 8,835,423 B2 | 9/2014 | Arvanitis et al. |
| 8,841,318 B2 | 9/2014 | Arvanitis et al. |
| 8,883,806 B2 | 11/2014 | Zhou et al. |
| 8,889,697 B2 | 11/2014 | Rodgers et al. |
| 8,933,085 B2 | 1/2015 | Rodgers et al. |
| 8,933,086 B2 | 1/2015 | Rodgers et al. |
| 8,946,245 B2 | 2/2015 | Rodgers et al. |
| 8,987,442 B2 | 3/2015 | Tung et al. |
| 8,987,443 B2 | 3/2015 | Liu |
| 8,993,582 B2 | 3/2015 | Zhou et al. |
| 9,000,161 B2 | 4/2015 | Zhou et al. |
| 9,023,840 B2 | 5/2015 | Yao et al. |
| 9,034,884 B2 | 5/2015 | Rodgers et al. |
| 9,079,912 B2 | 7/2015 | Rodgers et al. |
| 9,090,611 B2 | 7/2015 | Rodgers et al. |
| 9,181,271 B2 | 11/2015 | Li et al. |
| 9,200,004 B2 | 12/2015 | Xue et al. |
| 9,206,187 B2 | 12/2015 | Rodgers et al. |
| 9,216,984 B2 | 12/2015 | Li |
| 9,221,845 B2 | 12/2015 | Cao |
| 9,278,950 B2 | 3/2016 | Li et al. |
| 9,290,506 B2 | 3/2016 | Zhou et al. |
| 9,334,274 B2 | 5/2016 | Rodgers |
| 9,340,546 B2 | 5/2016 | Ahmad |
| 9,359,358 B2 | 6/2016 | Rodgers |
| 9,376,439 B2 | 6/2016 | Rodgers |
| 9,464,088 B2 | 10/2016 | Huang |
| 9,487,521 B2 | 11/2016 | Zhou et al. |
| 9,498,467 B2 | 11/2016 | Leopold et al. |
| 9,540,347 B2 | 1/2017 | Vechorkin et al. |
| 9,550,765 B2 | 1/2017 | Xue et al. |
| 9,556,197 B2 | 1/2017 | Li et al. |
| 9,580,418 B2 | 2/2017 | Sun et al. |
| 9,611,269 B2 | 4/2017 | Yao et al. |
| 9,623,029 B2 | 4/2017 | Li et al. |
| 9,655,854 B2 | 5/2017 | Yeleswaram |
| 9,676,750 B2 | 6/2017 | Li et al. |
| 9,802,918 B2 | 10/2017 | Vechorkin et al. |
| 9,822,124 B2 | 11/2017 | Vechorkin et al. |
| 9,849,120 B2 | 12/2017 | Xue et al. |
| 9,862,705 B2 | 1/2018 | Jia et al. |
| 9,920,032 B2 | 3/2018 | Vechorkin et al. |
| 9,974,790 B2 | 5/2018 | Rodgers et al. |
| 9,999,619 B2 | 6/2018 | Huang et al. |
| 10,000,507 B2 | 6/2018 | Li et al. |
| 10,265,307 B2 | 4/2019 | Xue et al. |
| 10,596,161 B2 * | 3/2020 | Koblish ............... A61K 31/519 |
| 2002/0111353 A1 | 8/2002 | Ledeboer et al. |
| 2003/0064969 A1 | 4/2003 | Bhagwat et al. |
| 2003/0100756 A1 | 5/2003 | Adams et al. |
| 2003/0144309 A1 | 7/2003 | Choon-Moon |
| 2003/0165576 A1 | 9/2003 | Fujii et al. |
| 2004/0009222 A1 | 1/2004 | Chou et al. |
| 2004/0009983 A1 | 1/2004 | Cox et al. |
| 2004/0029857 A1 | 2/2004 | Hale et al. |
| 2004/0077654 A1 | 4/2004 | Bouillot |
| 2004/0099204 A1 | 5/2004 | Nestor |
| 2004/0198737 A1 | 10/2004 | Cox et al. |
| 2004/0204404 A1 | 10/2004 | Zelle |
| 2004/0214928 A1 | 10/2004 | Aronov |
| 2004/0235862 A1 | 11/2004 | Burns |
| 2005/0014966 A1 | 1/2005 | Tabe |
| 2005/0054568 A1 | 3/2005 | Ling |
| 2005/0153989 A1 | 7/2005 | Grotzfeld et al. |
| 2006/0004010 A1 | 1/2006 | Habashita et al. |
| 2006/0020011 A1 | 1/2006 | Wu et al. |
| 2006/0079511 A1 | 4/2006 | Liu et al. |
| 2006/0106020 A1 | 5/2006 | Rodgers et al. |
| 2006/0106027 A1 | 5/2006 | Furet et al. |
| 2006/0128803 A1 | 6/2006 | Klimko |
| 2006/0135537 A1 | 6/2006 | Knegtel et al. |
| 2006/0178393 A1 | 8/2006 | Pitts |
| 2006/0183761 A1 | 8/2006 | Ledeboer et al. |
| 2006/0183906 A1 | 8/2006 | Rodgers et al. |
| 2006/0223864 A1 | 10/2006 | Biju |
| 2006/0293311 A1 | 12/2006 | Li et al. |
| 2007/0135461 A1 | 6/2007 | Rodgers et al. |
| 2007/0135466 A1 | 6/2007 | Ledeboer et al. |
| 2007/0149506 A1 | 6/2007 | Arvanitis et al. |
| 2007/0149561 A1 | 6/2007 | Dhanak et al. |
| 2007/0191364 A1 | 8/2007 | Braun et al. |
| 2007/0191405 A1 | 8/2007 | Noronha |
| 2007/0208053 A1 | 9/2007 | Wang et al. |
| 2007/0225286 A1 | 9/2007 | Ren et al. |
| 2007/0259904 A1 | 11/2007 | Noronha |
| 2008/0021026 A1 | 1/2008 | Borchardt et al. |
| 2008/0085898 A1 | 4/2008 | Lu |
| 2008/0096852 A1 | 4/2008 | Yanni |
| 2008/0119496 A1 | 5/2008 | Ohlmeyer |
| 2008/0161346 A1 | 7/2008 | Cheng |
| 2008/0188500 A1 | 8/2008 | Arvanitis et al. |
| 2008/0194468 A1 | 8/2008 | Bodor |
| 2008/0207570 A1 | 8/2008 | Segura-Orsoni |
| 2008/0207584 A1 | 8/2008 | Habashita et al. |
| 2008/0280876 A1 | 11/2008 | Hobson et al. |
| 2008/0312258 A1 | 12/2008 | Rodgers et al. |
| 2008/0312259 A1 | 12/2008 | Rodgers et al. |
| 2009/0018156 A1 | 1/2009 | Tang et al. |
| 2009/0076070 A1 | 3/2009 | Harada et al. |
| 2009/0088445 A1 | 4/2009 | Ledeboer et al. |
| 2009/0131403 A1 | 5/2009 | Kusuda |
| 2009/0181959 A1 | 7/2009 | Rodgers et al. |
| 2009/0197869 A1 | 8/2009 | Arvanitis et al. |
| 2009/0203637 A1 | 8/2009 | Hocek et al. |
| 2009/0215766 A1 | 8/2009 | Rodgers et al. |
| 2009/0221608 A1 | 9/2009 | Cui et al. |
| 2009/0233903 A1 | 9/2009 | Rodgers et al. |
| 2009/0318405 A1 | 12/2009 | Li et al. |
| 2010/0022522 A1 | 1/2010 | Rodgers et al. |
| 2010/0069381 A1 | 3/2010 | Itoh et al. |
| 2010/0113416 A1 | 5/2010 | Friedman et al. |
| 2010/0190981 A1 | 7/2010 | Zhou et al. |
| 2010/0210627 A1 | 8/2010 | Mao et al. |
| 2010/0298334 A1 | 11/2010 | Rodgers et al. |
| 2010/0298355 A1 | 11/2010 | Li et al. |
| 2011/0059951 A1 | 3/2011 | Rodgers et al. |
| 2011/0059961 A1 | 3/2011 | Wang et al. |
| 2011/0082159 A1 | 4/2011 | Rodgers et al. |
| 2011/0086810 A1 | 4/2011 | Rodgers et al. |
| 2011/0086835 A1 | 4/2011 | Rodgers et al. |
| 2011/0201593 A1 | 8/2011 | Babu et al. |
| 2011/0207754 A1 | 8/2011 | Li et al. |
| 2011/0223210 A1 | 9/2011 | Rodgers et al. |

(56) References Cited

U.S. PATENT DOCUMENTS

| | | |
|---|---|---|
| 2011/0224157 A1 | 9/2011 | Rodgers et al. |
| 2011/0224190 A1 | 9/2011 | Huang et al. |
| 2011/0288107 A1 | 11/2011 | Parikh et al. |
| 2012/0014989 A1 | 1/2012 | Rodgers |
| 2012/0077798 A1 | 3/2012 | Rodgers et al. |
| 2012/0114663 A1 | 5/2012 | Gelfand et al. |
| 2012/0149681 A1 | 6/2012 | Rodgers |
| 2012/0149682 A1 | 6/2012 | Rodgers et al. |
| 2012/0214825 A1 | 8/2012 | Vannucchi et al. |
| 2012/0225057 A1 | 9/2012 | Flynn |
| 2012/0225062 A1 | 9/2012 | Burger et al. |
| 2012/0252779 A1 | 10/2012 | Ramsden |
| 2012/0301464 A1 | 11/2012 | Friedman et al. |
| 2012/0329782 A1 | 12/2012 | Arvanitis et al. |
| 2013/0018034 A1 | 1/2013 | Yao et al. |
| 2013/0040973 A1 | 2/2013 | Vannucchi et al. |
| 2013/0045963 A1 | 2/2013 | Rodgers et al. |
| 2013/0057956 A1 | 3/2013 | Iwasa |
| 2013/0060026 A1 | 3/2013 | Zhou et al. |
| 2013/0137681 A1 | 5/2013 | Rodgers et al. |
| 2013/0225556 A1 | 8/2013 | Rodgers et al. |
| 2013/0253190 A1 | 9/2013 | Zhou et al. |
| 2013/0253191 A1 | 9/2013 | Zhou et al. |
| 2013/0253193 A1 | 9/2013 | Zhou et al. |
| 2013/0274257 A1 | 10/2013 | Arvanitis et al. |
| 2013/0296299 A1 | 11/2013 | Rodgers et al. |
| 2014/0004516 A1 | 1/2014 | Sattler et al. |
| 2014/0005166 A1 | 1/2014 | Rodgers et al. |
| 2014/0005210 A1 | 1/2014 | Rodgers et al. |
| 2014/0018374 A1 | 1/2014 | Rodgers et al. |
| 2014/0031344 A1 | 1/2014 | Arvanitis et al. |
| 2014/0073657 A1 | 3/2014 | Li et al. |
| 2014/0086941 A1 | 3/2014 | Reddy et al. |
| 2014/0088117 A1 | 3/2014 | Burch et al. |
| 2014/0094477 A1 | 4/2014 | Rodgers et al. |
| 2014/0121198 A1 | 5/2014 | Li et al. |
| 2014/0135350 A1 | 5/2014 | Ni et al. |
| 2014/0163000 A1 | 6/2014 | Ahmad |
| 2014/0171409 A1 | 6/2014 | Yao et al. |
| 2014/0200216 A1 | 7/2014 | Li et al. |
| 2014/0200227 A1 | 7/2014 | Xue et al. |
| 2014/0221379 A1 | 8/2014 | Rodgers et al. |
| 2014/0228346 A1 | 8/2014 | Rodgers et al. |
| 2014/0243360 A1 | 8/2014 | Rodgers et al. |
| 2014/0256941 A1 | 9/2014 | Liu et al. |
| 2014/0275031 A1 | 9/2014 | Huang et al. |
| 2014/0303196 A1 | 10/2014 | Rodgers et al. |
| 2014/0343030 A1 | 11/2014 | Li et al. |
| 2014/0378400 A1 | 12/2014 | Rodgers et al. |
| 2015/0057265 A1 | 2/2015 | Li et al. |
| 2015/0065447 A1 | 3/2015 | Sandor |
| 2015/0065484 A1 | 3/2015 | Yeleswaram et al. |
| 2015/0087632 A1 | 3/2015 | Rodgers et al. |
| 2015/0087662 A1 | 3/2015 | Li et al. |
| 2015/0152117 A1 | 6/2015 | Gibbons |
| 2015/0164900 A1 | 6/2015 | Rodgers et al. |
| 2015/0183805 A1 | 7/2015 | Liu et al. |
| 2015/0225411 A1 | 8/2015 | Yao et al. |
| 2015/0225412 A1 | 8/2015 | Brameld |
| 2015/0238492 A1 | 8/2015 | Rodgers et al. |
| 2015/0246046 A1 | 9/2015 | Vaddi |
| 2015/0250790 A1 | 9/2015 | Parikh et al. |
| 2015/0315185 A1 | 11/2015 | Rodgers et al. |
| 2015/0329534 A1 | 11/2015 | Xue et al. |
| 2015/0342952 A1 | 12/2015 | Leopold |
| 2015/0344497 A1 | 12/2015 | Zhou et al. |
| 2016/0000795 A1 | 1/2016 | Scherle |
| 2016/0009714 A1 | 1/2016 | Sun et al. |
| 2016/0009726 A1 | 1/2016 | Vechorkin et al. |
| 2016/0015695 A1 | 1/2016 | Li et al. |
| 2016/0024109 A1 | 1/2016 | Li |
| 2016/0067253 A1 | 3/2016 | Li et al. |
| 2016/0137626 A1 | 5/2016 | Li et al. |
| 2016/0272648 A1 | 9/2016 | Rodgers et al. |
| 2016/0346286 A1 | 12/2016 | Rodgers et al. |
| 2016/0347734 A1 | 12/2016 | Liu et al. |
| 2016/0347735 A1 | 12/2016 | Vechorkin et al. |
| 2017/0015674 A1 | 1/2017 | Zhou et al. |
| 2017/0071947 A1 | 3/2017 | Rodgers et al. |
| 2017/0087158 A1 | 3/2017 | Friedman et al. |
| 2017/0096411 A1 | 4/2017 | Vechorkin et al. |
| 2017/0121310 A1 | 5/2017 | Jia et al. |
| 2017/0158670 A1 | 6/2017 | Vechorkin et al. |
| 2017/0182017 A1 | 6/2017 | Xue et al. |
| 2017/0190716 A1 | 7/2017 | Li et al. |
| 2017/0246157 A1 | 8/2017 | Huang et al. |
| 2017/0253587 A1 | 9/2017 | Sun et al. |
| 2017/0253598 A1 | 9/2017 | Yao et al. |
| 2017/0319487 A1 | 11/2017 | Yeleswaram et al. |
| 2018/0170907 A1 | 6/2018 | Jia et al. |
| 2018/0193323 A1 | 7/2018 | Xue et al. |
| 2018/0282302 A1 | 10/2018 | Vechorkin et al. |
| 2018/0338978 A1 | 11/2018 | Rodgers et al. |
| 2018/0353499 A1 | 12/2018 | Huang et al. |
| 2019/0111058 A1 | 4/2019 | Vaddi |
| 2019/0125750 A1 | 5/2019 | Rodgers et al. |
| 2019/0135813 A1 | 5/2019 | Rodgers et al. |
| 2019/0175578 A1 | 6/2019 | Koblish et al. |
| 2019/0209537 A1 | 7/2019 | Xue et al. |
| 2019/0290627 A1 | 9/2019 | Cao et al. |

FOREIGN PATENT DOCUMENTS

| | | |
|---|---|---|
| CN | 102458581 | 5/2012 |
| CN | 102985417 | 3/2013 |
| CN | 102985426 | 3/2013 |
| CN | 103664878 | 3/2014 |
| DE | 30 36 390 | 5/1982 |
| EP | 0223420 | 5/1987 |
| EP | 0727217 | 8/1996 |
| EP | 0795556 | 9/1997 |
| EP | 2637650 | 9/2013 |
| EP | 2743269 | 6/2014 |
| JP | 07-010876 | 1/1995 |
| JP | 2003-155285 | 5/2003 |
| JP | 2006-502183 | 1/2006 |
| JP | 2006-518341 | 8/2006 |
| JP | 2008-508241 | 3/2008 |
| JP | 2008-545660 | 12/2008 |
| JP | 2009-504619 | 2/2009 |
| JP | 2010-529209 | 8/2010 |
| JP | 2011-503194 | 1/2011 |
| JP | 2011-514909 | 5/2011 |
| WO | WO 96/030343 | 10/1996 |
| WO | WO 97/002262 | 1/1997 |
| WO | WO 97/036587 | 10/1997 |
| WO | WO 97/038664 | 10/1997 |
| WO | WO 97/045412 | 12/1997 |
| WO | WO 98/044797 | 10/1998 |
| WO | WO 98/051391 | 11/1998 |
| WO | WO 99/000654 | 1/1999 |
| WO | WO 99/062908 | 12/1999 |
| WO | WO 99/065909 | 12/1999 |
| WO | WO 00/009495 | 2/2000 |
| WO | WO 00/051614 | 9/2000 |
| WO | WO 00/053595 | 9/2000 |
| WO | WO 00/063168 | 10/2000 |
| WO | WO 2001/014402 | 3/2001 |
| WO | WO 2001/027104 | 4/2001 |
| WO | WO 2001/042246 | 6/2001 |
| WO | WO 2001/064655 | 9/2001 |
| WO | WO 2001/081345 | 11/2001 |
| WO | WO 2001/081346 | 11/2001 |
| WO | WO 2001/098344 | 12/2001 |
| WO | WO 2002/000196 | 1/2002 |
| WO | WO 2002/000661 | 1/2002 |
| WO | WO 2002/046184 | 6/2002 |
| WO | WO 2002/055084 | 7/2002 |
| WO | WO 2002/055489 | 7/2002 |
| WO | WO 2002/055496 | 7/2002 |
| WO | WO 2002/060492 | 8/2002 |
| WO | WO 2002/080926 | 10/2002 |
| WO | WO 2002/092573 | 11/2002 |
| WO | WO 2002/093173 | 11/2002 |

(56) References Cited

FOREIGN PATENT DOCUMENTS

| | | |
|---|---|---|
| WO | WO 2002/096909 | 12/2002 |
| WO | WO 2003/000688 | 1/2003 |
| WO | WO 2003/000695 | 1/2003 |
| WO | WO 2003/011285 | 2/2003 |
| WO | WO 2003/024967 | 3/2003 |
| WO | WO 2003/037347 | 5/2003 |
| WO | WO 2003/048162 | 6/2003 |
| WO | WO 2003/092595 | 11/2003 |
| WO | WO 2003/099771 | 12/2003 |
| WO | WO 2003/099796 | 12/2003 |
| WO | WO 2003/106681 | 12/2003 |
| WO | WO 2004/003026 | 1/2004 |
| WO | WO 2004/005281 | 1/2004 |
| WO | WO 2004/005282 | 1/2004 |
| WO | WO 2004/024895 | 3/2004 |
| WO | WO 2004/026406 | 4/2004 |
| WO | WO 2004/041814 | 5/2004 |
| WO | WO 2004/046120 | 6/2004 |
| WO | WO 2004/047843 | 6/2004 |
| WO | WO 2004/056786 | 7/2004 |
| WO | WO 2004/072063 | 8/2004 |
| WO | WO 2004/080980 | 9/2004 |
| WO | WO 2004/090106 | 10/2004 |
| WO | WO 2004/092154 | 10/2004 |
| WO | WO 2004/099204 | 11/2004 |
| WO | WO 2004/099205 | 11/2004 |
| WO | WO 2005/005988 | 1/2005 |
| WO | WO 2005/013986 | 2/2005 |
| WO | WO 2005/020921 | 3/2005 |
| WO | WO 2005/026129 | 3/2005 |
| WO | WO 2005/028444 | 3/2005 |
| WO | WO 2005/028624 | 3/2005 |
| WO | WO 2005/033310 | 4/2005 |
| WO | WO 2005/049033 | 6/2005 |
| WO | WO 2005/051393 | 6/2005 |
| WO | WO 2005/060972 | 7/2005 |
| WO | WO 2005/061463 | 7/2005 |
| WO | WO 2005/062795 | 7/2005 |
| WO | WO 2005/089502 | 9/2005 |
| WO | WO 2005/095400 | 10/2005 |
| WO | WO 2005/105146 | 11/2005 |
| WO | WO 2005/105814 | 11/2005 |
| WO | WO 2005/105988 | 11/2005 |
| WO | WO 2005/110410 | 11/2005 |
| WO | WO 2005/117909 | 12/2005 |
| WO | WO 2005/121130 | 12/2005 |
| WO | WO 2005/123719 | 12/2005 |
| WO | WO 2006/004984 | 1/2006 |
| WO | WO 2006/006569 | 1/2006 |
| WO | WO 2006/013114 | 2/2006 |
| WO | WO 2006/022459 | 3/2006 |
| WO | WO 2006/039718 | 4/2006 |
| WO | WO 2006/046023 | 5/2006 |
| WO | WO 2006/046024 | 5/2006 |
| WO | WO 2006/052913 | 5/2006 |
| WO | WO 2006/056399 | 6/2006 |
| WO | WO 2006/067445 | 6/2006 |
| WO | WO 2006/069080 | 6/2006 |
| WO | WO 2006/071960 | 7/2006 |
| WO | WO 2006/077499 | 7/2006 |
| WO | WO 2006/078228 | 7/2006 |
| WO | WO 2006/096270 | 9/2006 |
| WO | WO 2006/101783 | 9/2006 |
| WO | WO 2006/108103 | 10/2006 |
| WO | WO 2006/122806 | 11/2006 |
| WO | WO 2006/127587 | 11/2006 |
| WO | WO 2006/129199 | 12/2006 |
| WO | WO 2006/136823 | 12/2006 |
| WO | WO 2007/002433 | 1/2007 |
| WO | WO 2007/011760 | 1/2007 |
| WO | WO 2007/025090 | 3/2007 |
| WO | WO 2007/041130 | 4/2007 |
| WO | WO 2007/041712 | 4/2007 |
| WO | WO 2007/043677 | 4/2007 |
| WO | WO 2007/044050 | 4/2007 |
| WO | WO 2007/044724 | 4/2007 |
| WO | WO 2007/044894 | 4/2007 |
| WO | WO 2007/048065 | 4/2007 |
| WO | WO 2007/049041 | 5/2007 |
| WO | WO 2007/052843 | 5/2007 |
| WO | WO 2007/062459 | 6/2007 |
| WO | WO 2007/070514 | 6/2007 |
| WO | WO 2007/076423 | 7/2007 |
| WO | WO 2007/077949 | 7/2007 |
| WO | WO 2007/084557 | 7/2007 |
| WO | WO 2007/084857 | 7/2007 |
| WO | WO 2007/090141 | 8/2007 |
| WO | WO 2007/090748 | 8/2007 |
| WO | WO 2007/116313 | 10/2007 |
| WO | WO 2007/117494 | 10/2007 |
| WO | WO 2007/129195 | 11/2007 |
| WO | WO 2007/131191 | 11/2007 |
| WO | WO 2007/135461 | 11/2007 |
| WO | WO 2007/140222 | 12/2007 |
| WO | WO 2008/002676 | 1/2008 |
| WO | WO 2008/013925 | 1/2008 |
| WO | WO 2008/022164 | 2/2008 |
| WO | WO 2008/028937 | 3/2008 |
| WO | WO 2008/035376 | 3/2008 |
| WO | WO 2008/043031 | 4/2008 |
| WO | WO 2008/045252 | 4/2008 |
| WO | WO 2008/054749 | 5/2008 |
| WO | WO 2008/058126 | 5/2008 |
| WO | WO 2008/064157 | 5/2008 |
| WO | WO 2008/067119 | 6/2008 |
| WO | WO 2008/077712 | 7/2008 |
| WO | WO 2008/079291 | 7/2008 |
| WO | WO 2008/079292 | 7/2008 |
| WO | WO 2008/082198 | 7/2008 |
| WO | WO 2008/082839 | 7/2008 |
| WO | WO 2008/082840 | 7/2008 |
| WO | WO 2008/106692 | 9/2008 |
| WO | WO 2008/121687 | 10/2008 |
| WO | WO 2008/124323 | 10/2008 |
| WO | WO 2008/127728 | 10/2008 |
| WO | WO 2008/133955 | 11/2008 |
| WO | WO 2008/139161 | 11/2008 |
| WO | WO 2008/143759 | 11/2008 |
| WO | WO 2008/145681 | 12/2008 |
| WO | WO 2008/145688 | 12/2008 |
| WO | WO 2008/157207 | 12/2008 |
| WO | WO 2008/157208 | 12/2008 |
| WO | WO 2009/007839 | 1/2009 |
| WO | WO 2009/014637 | 1/2009 |
| WO | WO 2009/016460 | 2/2009 |
| WO | WO 2009/017701 | 2/2009 |
| WO | WO 2009/049028 | 4/2009 |
| WO | WO 2009/064486 | 5/2009 |
| WO | WO 2009/064835 | 5/2009 |
| WO | WO 2009/065080 | 5/2009 |
| WO | WO 2009/071577 | 6/2009 |
| WO | WO 2009/100130 | 8/2009 |
| WO | WO 2009/108912 | 9/2009 |
| WO | WO 2009/109576 | 9/2009 |
| WO | WO 2009/114512 | 9/2009 |
| WO | WO 2009/115572 | 9/2009 |
| WO | WO 2009/151845 | 12/2009 |
| WO | WO 2009/158687 | 12/2009 |
| WO | WO 2010/000978 | 1/2010 |
| WO | WO 2010/001169 | 1/2010 |
| WO | WO 2010/002933 | 1/2010 |
| WO | WO 2010/020905 | 2/2010 |
| WO | WO 2010/022076 | 2/2010 |
| WO | WO 2010/022081 | 2/2010 |
| WO | WO 2010/026121 | 3/2010 |
| WO | WO 2010/026122 | 3/2010 |
| WO | WO 2010/026124 | 3/2010 |
| WO | WO 2010/039939 | 4/2010 |
| WO | WO 2010/048314 | 4/2010 |
| WO | WO 2010/057833 | 5/2010 |
| WO | WO 2010/071885 | 6/2010 |
| WO | WO 2010/081692 | 7/2010 |
| WO | WO 2010/083283 | 7/2010 |
| WO | WO 2010/135401 | 11/2010 |

(56) References Cited

FOREIGN PATENT DOCUMENTS

| | | |
|---|---|---|
| WO | WO 2010/135571 | 11/2010 |
| WO | WO 2010/135581 | 11/2010 |
| WO | WO 2010/135621 | 11/2010 |
| WO | WO 2010/135650 | 11/2010 |
| WO | WO 2010/148351 | 12/2010 |
| WO | WO 2011/008487 | 1/2011 |
| WO | WO 2011/025685 | 3/2011 |
| WO | WO 2011/025859 | 3/2011 |
| WO | WO 2011/028685 | 3/2011 |
| WO | WO 2011/029802 | 3/2011 |
| WO | WO 2011/031554 | 3/2011 |
| WO | WO 2011/031979 | 3/2011 |
| WO | WO 2011/035019 | 3/2011 |
| WO | WO 2011/035022 | 3/2011 |
| WO | WO 2011/035900 | 3/2011 |
| WO | WO 2011/044481 | 4/2011 |
| WO | WO 2011/053861 | 5/2011 |
| WO | WO 2011/057784 | 5/2011 |
| WO | WO 2011/058139 | 5/2011 |
| WO | WO 2011/060295 | 5/2011 |
| WO | WO 2011/063398 | 5/2011 |
| WO | WO 2011/066369 | 6/2011 |
| WO | WO 2011/068667 | 6/2011 |
| WO | WO 2011/069141 | 6/2011 |
| WO | WO 2011/075613 | 6/2011 |
| WO | WO 2011/075630 | 6/2011 |
| WO | WO 2011/075643 | 6/2011 |
| WO | WO 2011/079274 | 6/2011 |
| WO | WO 2011/101643 | 8/2011 |
| WO | WO 2011/112662 | 9/2011 |
| WO | WO 2011/124580 | 10/2011 |
| WO | WO 2011/130146 | 10/2011 |
| WO | WO 2011/130342 | 10/2011 |
| WO | WO 2011/144338 | 11/2011 |
| WO | WO 2011/146808 | 11/2011 |
| WO | WO 2011/163195 | 12/2011 |
| WO | WO 2012/003457 | 1/2012 |
| WO | WO 2012/004217 | 1/2012 |
| WO | WO 2012/007375 | 1/2012 |
| WO | WO 2012/015474 | 2/2012 |
| WO | WO 2012/016217 | 2/2012 |
| WO | WO 2012/045010 | 4/2012 |
| WO | WO 2012/064981 | 5/2012 |
| WO | WO 2012/065297 | 5/2012 |
| WO | WO 2012/065546 | 5/2012 |
| WO | WO 2012/068440 | 5/2012 |
| WO | WO 2012/068450 | 5/2012 |
| WO | WO 2012/071612 | 6/2012 |
| WO | WO 2012/078777 | 6/2012 |
| WO | WO 2012/080990 | 6/2012 |
| WO | WO 2012/087881 | 6/2012 |
| WO | WO 2012/101029 | 8/2012 |
| WO | WO 2012/101032 | 8/2012 |
| WO | WO 2012/120415 | 9/2012 |
| WO | WO 2012/120428 | 9/2012 |
| WO | WO 2012/125629 | 9/2012 |
| WO | WO 2012/129338 | 9/2012 |
| WO | WO 2012/135009 | 10/2012 |
| WO | WO 2012/137089 | 10/2012 |
| WO | WO 2012/139930 | 10/2012 |
| WO | WO 2012/145617 | 10/2012 |
| WO | WO 2012/146933 | 11/2012 |
| WO | WO 2012/146936 | 11/2012 |
| WO | WO 2012/148775 | 11/2012 |
| WO | WO 2012/154274 | 11/2012 |
| WO | WO 2012/156367 | 11/2012 |
| WO | WO 2012/156756 | 11/2012 |
| WO | WO 2012/163942 | 12/2012 |
| WO | WO 2012/170827 | 12/2012 |
| WO | WO 2012/175591 | 12/2012 |
| WO | WO 2012/177606 | 12/2012 |
| WO | WO 2013/013188 | 1/2013 |
| WO | WO 2013/020369 | 2/2013 |
| WO | WO 2013/20370 | 2/2013 |
| WO | WO 2013/020371 | 2/2013 |
| WO | WO 2013/023119 | 2/2013 |
| WO | WO 2013/024002 | 2/2013 |
| WO | WO 2013/026025 | 2/2013 |
| WO | WO 2013/033569 | 3/2013 |
| WO | WO 2013/034570 | 3/2013 |
| WO | WO 2013/036611 | 3/2013 |
| WO | WO 2013/041634 | 3/2013 |
| WO | WO 2013/045461 | 4/2013 |
| WO | WO 2013/050446 | 4/2013 |
| WO | WO 2013/050448 | 4/2013 |
| WO | WO 2013/130660 | 9/2013 |
| WO | WO 2013/134079 | 9/2013 |
| WO | WO 2013/066684 | 10/2013 |
| WO | WO 2013/144189 | 10/2013 |
| WO | WO 2013/149909 | 10/2013 |
| WO | WO 2013/151930 | 10/2013 |
| WO | WO 2013/160873 | 10/2013 |
| WO | WO 2013/163279 | 10/2013 |
| WO | WO 2013/170068 | 11/2013 |
| WO | WO 2013/171639 | 11/2013 |
| WO | WO 2013/173720 | 11/2013 |
| WO | WO 2013/175388 | 11/2013 |
| WO | WO 2013/177219 | 11/2013 |
| WO | WO 2013/186692 | 12/2013 |
| WO | WO 2013/188783 | 12/2013 |
| WO | WO 2014/001377 | 1/2014 |
| WO | WO 2014/011974 | 1/2014 |
| WO | WO 2014/022752 | 2/2014 |
| WO | WO 2014/033630 | 3/2014 |
| WO | WO 2014/033631 | 3/2014 |
| WO | WO 2014/041131 | 3/2014 |
| WO | WO 2014/048939 | 4/2014 |
| WO | WO 2014/053568 | 4/2014 |
| WO | WO 2014/060411 | 4/2014 |
| WO | WO 2014/071031 | 5/2014 |
| WO | WO 2014/076162 | 5/2014 |
| WO | WO 2014/079011 | 5/2014 |
| WO | WO 2014/079136 | 5/2014 |
| WO | WO 2014/009447 | 6/2014 |
| WO | WO 2014/089379 | 6/2014 |
| WO | WO 2014/097151 | 6/2014 |
| WO | WO 2014/099880 | 6/2014 |
| WO | WO 2014/100158 | 6/2014 |
| WO | WO 2014/100323 | 6/2014 |
| WO | WO 2014/100719 | 6/2014 |
| WO | WO 2014/106706 | 7/2014 |
| WO | WO 2014/110574 | 7/2014 |
| WO | WO 2014/113388 | 7/2014 |
| WO | WO 2014/134426 | 9/2014 |
| WO | WO 2014/138168 | 9/2014 |
| WO | WO 2014/138906 | 9/2014 |
| WO | WO 2014/138907 | 9/2014 |
| WO | WO 2014/139145 | 9/2014 |
| WO | WO 2014/140597 | 9/2014 |
| WO | WO 2014/140644 | 9/2014 |
| WO | WO 2014/140861 | 9/2014 |
| WO | WO 2014/141171 | 9/2014 |
| WO | WO 2014/142290 | 9/2014 |
| WO | WO 2014/142292 | 9/2014 |
| WO | WO 2014/143601 | 9/2014 |
| WO | WO 2014/143768 | 9/2014 |
| WO | WO 2014/145051 | 9/2014 |
| WO | WO 2014/150258 | 9/2014 |
| WO | WO 2014/150276 | 9/2014 |
| WO | WO 2014/151008 | 9/2014 |
| WO | WO 2014/151634 | 9/2014 |
| WO | WO 2014/186706 | 11/2014 |
| WO | WO 2015/021153 | 2/2015 |
| WO | WO 2015/027124 | 2/2015 |
| WO | WO 2015/131031 | 9/2015 |
| WO | WO 2015/157257 | 10/2015 |
| WO | WO 2015/168246 | 11/2015 |
| WO | WO 2015/184305 | 12/2015 |
| WO | WO 2015/191677 | 12/2015 |
| WO | WO 2017/044730 | 3/2017 |
| WO | WO 2015/184087 | 4/2018 |

(56) References Cited

OTHER PUBLICATIONS

Abelson et al., "Dry eye syndrome: diagnosis, clinical trials, and pharmaceutical treatment- 'improving clinical trials'. Lacrimal Gland, Tear Film, and Dry Eye Syndromes 3 Part B," Adv Exp Med Biol, 2002, 506: 1079-86.
Abstract of Chilean patent application No. 3496-06 published in Official Gazette of the Republic of Chile (Jun. 1, 2007) and publication (2 pages).
Ahmed et al., "Treatment of Pemphigus Vulgaris with Rituximab and Intravenous Immune Globulin," The New England Journal of Medicine, 2006, 1772-1779.
Aho et al., "Expression of human pim family genes is selectively up-regulated by cytokines promoting T helper type 1, but not T helper type 2, cell differentiation," Immunology, 2005, 116: 82-88.
Albach et al., "Diagnosis of keratoconjunctivitis sicca in rheumatoid arthritis. The value of various tests," Ophthalmologe, Apr. 1994; 91(2):229-34—in German (with English abstract/summary contained therein).
Amson et al., "The human protooncogene product p33pim is expressed during fetal hematopoiesis and in diverse leukemias," Proc. Nat. Acad. Sci., USA, 1989, 86:8857-61.
Anderson et al., "Biochemical characterization of GSK1070916, a potent and selective inhibitor of Aurora B and Aurora C kinases with an extremely long residence time," Biochem J., 2009, 420(2):259-265.
Anonymous, "Ruxolitinib for Patients with Low or Intermediate-1 Risk Myelodysplastic Syndrome (MDS)," ClinicalTrials.gov archive, Aug. 2013, XP002739581, Retrieved from the Internet: URL: clinicaltrials.gov/archive/NCT01895842/2013_08_19 [retrieved on Apr. 30, 2015], 5 pages.
Arber et al., "The 2016 revision to the World Health Organization classification of myeloid neoplasms and acute leukemia," Blood, May 2016, 2391-2405.
Arunesh et al., "Small molecule inhibitors of PIM1 kinase: Jul. 2009 to Feb. 2013 patent update," Expert Opin Ther Pat, Jan. 2014, 24(1):5-17.
Asano et al., "The serine/threonine kinase Pim-2 is a novel anti-apoptotic mediator in myeloma cells," Leukemia, 2011, 25: 1182-1188.
Australian Office Action in Australian Application No. 2014207691, dated Aug. 17, 2017, 4 pages.
Australian Office Action in Australian Application No. 2016204689, dated Mar. 22, 2017, 4 pages.
Australian Office Action in Australian Application No. 2018217210, dated Feb. 22, 2019, 4 pages.
Bachmann et al., "The serine/threonine kinase Pim-1," The International Journal of Biochemistry and Cell Biology, 2005, 37: 726-730.
Bain et al., "Chronic neutrophilic leukaemia," in: Swerdlow, et al., eds. WHO Classification of Tumors of Haematopoietic and Lymphoid Tissues (ed 4th). Lyon: IARC Press, 2008: 38-39.
Bamborough, "Assessment of Chemical Coverage of Kinome Space and Its Implications for Kinase Drug Discovery," J. Med. Chem., 2008, 51: 7898-7914.
Banker et al., "Modern Pharmaceuticals" Third Edition, 1996, 596.
Barabino et al., "Tear film and ocular surface tests in animal models of dry eye; uses and limitations," Experimental Eye Research, 2004, 79: 613-621.
Baron et al., "PIM1 gene cooperates with human BCL6 gene to promote the development of lymphomas," PNAS, Apr. 2012, 109(15): 5735-5739.
Barr et al., "Corneal scarring in the Collaborative Longitudinal Evaluation of Keratoconus (CLEK) Study: baseline prevalence and repeatability of detection," Cornea, 1999, 18(1):34-46.
Baudouin et al., "Flow cytometry in impression cytology specimens. A new method for evaluation of conjunctival Inflammation," Invest Ophthalmol Vis Sci, 1997, 38: 1458-1464.
Baxter et al., "Acquired mutation of the tyrosine kinase JAK2 in human myeloproliferative disorders," Lancet, 2005, 365:1054-1061.
Baxter et al., "Reductive Aminations of Carbonyl Compounds with Borohydride and Borane Reducing Agents," Organic Reactions, 2002, 1-57.
Baytel et al., "The human Pim-2 proto-oncogene and its testicular expression," Biochimica et Biophysica Acta, 1998, 1442: 274-285.
Beck et al., "Brief Report: Alleviation of Systemic Manifestations of Castleman's Disease by Monoclonal Anti-Interleukin-6 Antibody," N. Engl. J. Med., 1994, 330(9):602-605.
Begley et al., "Use of the dry eye questionnaire to measure symptoms of ocular irritation in patients with aqueous tear deficient dry eye," Cornea, 2002, 21: 664-70.
Bell and Zalay, "Synthesis of Substituted 3-Amino[6,5-b]triazinoindoles," Journal of Heterocyclic Chemistry, Oct. 1975, 12(5): 1001-1004.
Bennett et al., "Proposals for the classification of the myelodysplastic syndromes," British Journal of Haematology, 1982,51: 189-199.
Berge et al., "Pharmaceutical Salts," Journal of Pharmaceutical Science, 1977, 66(2): 1-19.
Beyer, "Uber die Synthese von 2-Methylmercapto-1,3,4-thiodiazinen und deren Umlagerung in Pyrazolderivate (The synthesis of 2-methylthio-1,3,4-thiadiazines and their rearrangement to pyrazole derivatives)," Chem. Berichte Jahrg., 92:2593-2599 (1959) (abstract provided).
Bhattacharya et al., "Polymorphism in Pharmaceutical Solids," Second Edition, 2009, 192:327-345.
Bhovi et al., "1,3-Dipolar Cycloaddition Reaction: Synthesis and Antimicrobial, Activity of Some New 3-Ethoxycarbonyl-s-Methoxy-6-Bromo-2-Triazolylmethylindoles," Indian Journal of Heterocyclic Chemistry, Jul.-Sep. 2004, 14: 15-18.
Blanco-Aparicio, "Pim kinases in cancer: Diagnostic, prognostic and treatment opportunities," Biochemical Pharmacology, 2013, 85:629-643.
Blom et al., "Optimizing Preparative LC/MS Configurations and Methods for Parallel Synthesis Purification," J. Comb. Chem., 2003, 5: 670-683.
Blom et al., "Preparative LC-MS Purification: Improved Compound Specific Method Optimization," J. Comb. Chem., 2004, 6:874-883.
Blom, "Two-Pump at Column Dilution Configuration for Preparative Liquid Chromatography—Mass Spectrometry," J. Comb. Chem., 2002, 4:295-301.
Blume-Jensen et al., "Oncogenic kinase signaling," Nature, 2001, 411(6835):355-365.
Bock et al. "Managing drug resistance in cancer: lessons from HIV therapy," Nature, Jul. 2012, 12:494-501.
Bolen, "Nonreceptor tyrosine protein kinases," Oncogene, 1993, 8(8):2025-31.
Bollrath et al., "gpl30-Mediated Stat3 Activation in Enterocytes Regulates Cell Survival and Cell-Cycle Progression during Colitis-Associated Tumorigenesis," Cancer Cell, 2009, 15:91-102.
Bondoux et al., "Palladium-catalyzed C-C coupling: efficient preparation of new 5-thio-B-D-xylopyranosides as oral venous antithrombotic drugs," Tetrahedron Letters, 2009, 50(27): 3872-3876.
Borie et al., "Combined Use of the Jak3 Inhibitor CP-690, 550 with Mycophenolate Mofetil to Prevent Kidney Allograft Rejection in Nonhuman Primates," Transplantation, Dec. 2005, 80(12): 1756-64.
Bose and Verstovsek, "JAK Inhibitors for myeloproliferative neoplasms: What is next?" Blood, Jul. 13, 2017, 130(2): 115-125.
Bosworth, "JAK1/JAK2 Inhibitor Ruxolitinib Is a Rising Start," Clinical Oncology, Apr. 2011, 06:04, 3 pages.
Boudny et al., "JAK/STAT signaling pathways and cancer," Neoplasm, 2002, 49:349-355.
Bourcier et al., "Expression of CD40 and CD40 ligand in the human conjunctival epithelium," Invest Ophthalmol Vis Sci, 2000, 41:120-126.
Bowman et al. "STATs in oncogenesis," Oncogene, 2000, 19:2474-2488.
Brault et al., "PIM kinases are progression markers and emerging therapeutic targets in diffuse large B-cell lymphoma," British Journal of Cancer, 2012, 107: 491-500.
Brett et al., "Structural chemistry of polycyclic heteroaromatic compound. Part 4. Electronic structures of angular dithienopyridines," J Chem Soc, Perkin Trans 2, Jan. 1, 1994, 9:2045.

(56) References Cited

OTHER PUBLICATIONS

Brignole et al., "Expression of Fas-Fas Ligand Antigens and Apoptotic Marker APO2-7 by the Human Conjunctival Epithelium. Positive correlation with class II HLA DR expression in inflammatory Ocular Surface Disorders," Exp Eye Res, 1998, 67:687-697.
Brignole et al., "Flow cytometric analysis of inflammatory markers in conjunctival epithelial cells of patients with dry eyes," Invest Ophthalmol Vis Sci, 2000, 41:1356-1363.
Brignole et al., "Flow cytometric analysis of inflammatory markers in KCS: 6-month treatment with topical cyclosporin A," Invest Ophthalmol Vis Sci, 2001, 42:90-95.
Brignole et al., "Flow cytometry in conjunctival impression cytology: a new tool for exploring ocular surface pathologies," Exp Eye Res, 2004, 78:473-481.
Bromberg et al., "Inflammation and Cancer: IL-6 and STAT3 Complete the Link," Cancer Cell, 2009, 15:79-80.
Bron et al., "Grading of corneal and conjunctival staining in the context of other dry eye tests," Cornea, 2003, 22(7):640-50.
Bron et al., "Methodologies to Diagnose and Monitor Dry Eye Disease: Report of the Diagnostic Methodology Subcommittee of the International Dry Eye Workshop (2007)," The Ocular Surface, Apr. 2007, 5(2): 108-152.
Brunning et al., "Myelodysplastic syndromes/neoplasms, overview," WHO Classification of Tumours of Haematopoietic and Lymphoid Tissues, 4th edition, 2008, 88-103.
Brunton et al., "Chemotherapy of Neoplastic Diseases," Goodman & Gillman's: The Pharmacological Basis of Therapeutics, 11th edition, 2008, 853-908.
Burger et al. "Structure Guided Optimization, in Vitro Activity, and in Vivo Activity of Pan-PIM Kinase Inhibitors," ACS Med Chem Lett., 2013, 4:1193-1197.
Burger et al., "Gp130 and ras mediated signaling in human plasma cell line IN/a-6: a cytokine-regulated tumor model for plasmacytoma," Hematol J., 2001, 2:42-53.
Burger et al., "Janus kinase inhibitor INCB20 has antiproliferative and apoptotic effects on human myeloma cells in vitro and in vivo," Mol. Cancer Ther., Jan. 2009, 8(1): 26-35.
Caira, "Crystalline Polymorphism of Organic Compounds," Topics in Current Chemistry, Jan. 1998, 198: 163-208.
Campas-Moya, "Ruxolitinib. Tyrosine-protein kinase JAK1/2 inhibitor, treatment of myelofibrosis, treatment of myeloproliferative neoplasms, treatment of psoriasis," Drugs of the Future, Jun. 2010, 35(6):457-465.
Canadian Office Action in Canadian Application No. 2,738,520, dated Jul. 16, 2018, 7 pages.
Cancer [online], [retrieved on Jul. 6, 2007] Retrieved from the Internet, URL: http://www.nlm.nih.gov/medlineplus/cancer.html.
Cancer.org "Breast Cancer," American Cancer Society, [retrieved on Dec. 1, 2014] retrieved from URL <http://www.cancer.org.cancer/breastcancer/detailedguide/breast-cancer-prevention>, 4 pages.
Candotti et al., "Molecular aspects of primary immuno-deficiencies: lessons from cytokine and other signaling pathways.," J Clin Invest, May 2002, 109(10): 1261-9.
Candotti et al., "Structural and functional basis for JAK3-deficient severe combined immunodeficiency.," Blood, 1997, 90(10): 3996-4003.
Carey and Sundberg, "Part B: Reactions and Synthesis," Advanced Organic Chemistry, Kluwer Academic/Plenum Publishers: New York, 2001, 4th ed., 111-119.
Carey and Sundberg, "Part B: Reactions and Synthesis, Oxidations," Advanced Organic Chemistry, Kluwer Academic/Plenum Publishers: New York, 2001, 4th ed., 747-757.
Casetti et al., "Efficacy of Ruxolitinib in Chronic Eosinophilic Leukemia Associated with t(8,9)(p22;p24) and PCM1-JAK2 Fusion Gene," Blood, 2012, 120:2833.
Cazzola et al., American Society of Hematology (ASH Education Book), 2011(1), 2011, 264-272.
Cermak et al., "Is complete androgen insensitivity syndrome associated with alterations in the meibomian gland and ocular surface," Cornea, 2003, 22:516-521.

Cervantes et al., "Three-year efficacy, safety, and survival findings from COMFORT-II, a phase 3 study comparing ruxolitinib with best available therapy for myelofibrosis," Blood, Dec. 12, 2013, 122(25):4047-4053.
Cervantes-Gomez et al., "Biological Effects of the Pim Kinase Inhibitor, SGI-1776, in Multiple Myeloma," Clinical Lymphoma, Myeloma & Leukemia, Sep. 2013, S317-S329.
Cetkovic-Cvrlje et al., "Targeting JAK3 with JANEX-1 for prevention of autoimmune type 1 diabetes in NOD mice.," Clin Immunol, 2003, 106(3): 213-25.
Chaichian "Targeted Therapies in Systemic Lupus Erythematosus: A State-of-the-Art-Review" J Clin Cell Immunol 2013, S6, 1-8.
Chalandon, "Targeting mutated protein tyrosine kinases and their signaling pathways in hematologic malignancies," Haematologica, 2005, 90(7):949-68.
Chan et al., "New N- and O-arylations with phenylboronic acids and cupric acetate," Tetrahedron Letters, May 1998, 39(19): 2933-2936.
Chan, "Skin inflammatory disorders," In In Vivo Models of Inflammation, 2006, 85-120.
Changelian et al., "Prevention of Organ Allograft Rejection by a Specific Janus Kinase 3 Inhibitor," Science, 2003, 302: 875-878.
Chari et al., "Complete Remission Achieved with Single Agent CNTO 328, an Anti-IL-6 Monoclonal Antibody, in Relapsed and Refractory Myeloma," Clinical Lymphoma, Myeloma & Leukemia, 2013, 13(3)333-337.
Chauhan et al., "Autoimmunity in Dry Eye due to resistance of Th 17 to Treg Suppression," J. Immunology, 2009, 182(3): 1247-52.
Chauhan et al., "A concise review on sustained drug delivery system and its opportunities," International Journal on Pharmtech Research, Mar. 2012, 2: 227-238.
Chemical encyclopedia publication "Soviet Encyclopedia," Moscow, 1988, 1:242-243.
Chen et al., "Blockade of interleukin-6 signaling augments regulatory T-cell reconstitution and attenuates the severity of graft-versus-host disease," Blood, Jul. 2009, 114(4): 891-900.
Chen et al., "Mechanisms of cytotoxicity to Pim kinase inhibitor, SGI-1776, in acute myeloid leukemia," Blood, Jul. 2011, 118(3): 693-702.
Chen et al., "Pim kinase inhibitor, SGI-1776, induces apoptosis in chronic lymphocytic leukemia cells," Blood, 2009, 114:4150-57.
Chen et al., "Stat3 Activation in Human Endometrial and Cervical Cancer," British Journal of Cancer, 2007, 96: 591-599.
Chen et al., "Induction of myelodysplasia by myeloid-derived suppressor cells," J Clin Invest, Nov. 2013, 123(11): 4595-611.
Cheson et al., "Report of an international working group to standardize response criteria for myelodysplastic syndromes," Blood, Dec. 2000, 96(12): 3671-4.
Chew et al., "An instrument for quantifying meibomian lipid on the lid margin: the Meibometer," Curr Eye Res, 1993, 12:247-254.
Chew et al., "The casual level of meibomian lipids in humans," Current Eye Research, 1993, 12:255-259.
Chilean Office Action in Chilean Application No. 1985-2015, dated Mar. 23, 2017, 13 pages (English Translation).
Chilean Office Action in Chilean Application No. 201600398, dated Jul. 27, 2017, 16 pages (English Translation).
Chilean Office Action in Chilean Application No. 611-2018. dated May 16, 2019, 21 pages.
Chilean Office Action, Patent Application No. 1985-2015, dated Jul. 7, 2016, 22 pages (English Translation).
Chinese Notice of Reexamination in Chinese Application No. 201080033675.6, dated May 10, 2016, 18 pages (English Translation).
Chinese Office Action in Chinese Application No. 201480012783.3. dated Sep. 6, 2016, 16 pages (English Translation).
Chinese Office Action in Chinese Application No. 201480024761.9, dated Oct. 8, 2016, 21 pages (English Translation).
Chinese Office Action in Chinese Application No. 201480052299.3, dated Jan. 25, 2018, 13 pages.
Chinese Office Action in Chinese Application No. 201480057613.7, dated Apr. 5, 2017, 15 pages (English Translation).
Chinese Office Action in Chinese Application No. 201610989522.8, dated Jun. 4, 2018, 19 pages.

(56) References Cited

OTHER PUBLICATIONS

Cho et al., "Review of the tear break-up time and a closer look at the tear break-up time of Hong Kong Chinese," Optom Vis Sci, 1993, 70(1):30-8.
Choi Ha-Soon et al., "Design and synthesis of 7H-pyrrolo[2,3-d]pyrimidines as focal adhesion kinase inhibitors. Part 1," Bioorg. & Med. Chem. Lett., 2006, 16(8):2173-2176.
Choy et al., "Therapeutic Benefit of Blocking Interleukin-6 Activity With an Anti-Interleukin-6 Receptor Monoclonal Antibody in Rheumatoid Arthritis," Arthritis & Rheumatism, 2002, 46(12):3143-3150.
Chu-Moyer et al., "Preparation of the Four Regioisomeric 2-(Methylthio)oxazolopyridines: Useful Synthons for Elaboration to 2-(Amino substituted)oxazolopyridines," J. Org. Chem., 1995, 60(17):5721-5725.
Cilloni et al., "Emerging drugs for chronic myeloid leukemia," Expert Opinion on Emerging Drugs, Jun. 2010, 15(2): 175-184.
Claessens et al., "In vitro proliferation and differentiation of erythroyd progenitors from patients with myelodysplastic syndromes: evidence for Fas-dependent apoptosis," Blood, Mar. 2002, 1594-1601.
Claridge et al., "Discovery of a novel and potel series of thienol[3,2-b]pyridine-based inhibitors of c-Met and VEGFR2 tyrosine kinases," Bioorganic & Medical Chemistry Letters, 2008, 2793-2798.
Clark et al., "Discovery and Development of Janus Kinase (JAK) inhibitors for Inflammatory Diseases," J Med Cherm., 2014, A-P.
Claudio et al., "A molecular compendium of genes expressed in multiple myeloma," Blood, 2002, 100:2175-86.
Clevelandclinic.org, "Lupus," Feb. 2001, [retrieved on Dec. 15, 2018] retrieved from URL <https://my.clevelandclinic.org/health/diseases/4875-lupus>, 7 pages.
Clinical Trial NCT01787487 ('487 Trial), dated Feb. 7, 2013, 6 pages.
Clinicaltrials.gov, "A Study to Evaluate the Safety and Efficacy of INCB018424 Phosphate Cream Applied Topically to Adults With Atopic Dermatitis," Retrieved on Dec. 19, 2018, retrieved from URL <https://clinicaltrails.gov/ct/show/NCT03011892>, 7 pages.
Clinicaltrials.gov, "Topical Ruxolitinib for the Treatment of Vitiligo," Retrieved on Dec. 19, 2018, retrieved from URL <clinicaltrials.gov/ct2/show/NCT02809976>, 6 pages.
Clinicaltrials.gov, <http:clinicaltrials.gov/ct2/dhow/NCT00227591>, downloaded Dec. 6, 2016.
Coligan, "Current Protocols in Immunology," Wiley Press, 1988, vol. 3, Chapter abstracts only, 21 pages.
Colombian Office Action in Colombian Application No. 12-213.010, dated Jun. 17, 2014, 20 pages.
Colombian Office Action in Colombian Application No. 15-168.544, dated Aug. 10, 2016, 10 pages.
Colombian Office Action in Colombian Application No. 16-070.957, dated Sep. 13, 2017, 7 pages.
Conklyn et al., "The JAK3 inhibitor CP-0690550 selectivley reduces NK and CD+ cell numbers in cynomolgus monkey blood following chronic oral dosing," Journal of Leukocyte Biology, Dec. 2004, 76:1248-1255.
Coperet, "A simple and efficient method for the preparation of pyridine N-Oxides," The Journal of Organic Chemistry, Jan. 1998, 63:1740-1741.
Costa Rican Office Action in Costa Rican Application No. 10065, dated Jul. 16, 2013, 8 pages.
Costa Rican Office Action in Costa Rican Application No. 2013-506, dated May 21, 2018, 15 pages (English Translation).
Cottet and Schlosser, "Three Chloro(trifluoromethyl)pyridines as Model Substrates for Regioexhaustive Functionalization," Eur J Org Chem, 2004, 18:3793-3798.
Craig et al. "Tear lipid layer structure and stability following expression of the meibomian glands.," Ophthalmic Physiol Opt, 1995, 15(6):569-74.
Damia "Contemporary pre-clinical development of anticancer agents—What are the optimal preclinical models?" European Journal of Cancer, 2009, 45:2768-2781.

Daniels et al., "Imatinib mesylate inhibits the profibrogenic activity of TGF-? and prevents bleomycinmediated lung fibrosis," J. Clin, Invest., Nov. 2004, 114(9):1308-1316.
Danjo et al., "Observation of precorneal tear film in patients with Sjogren's syndrome," Acta Ophthalmol Scand, 1995, 73:501-505.
Dao et al., "Phase 2 Study of Ruxolitinib in Patients with Chronic Neutrophilic Leukemia or Atypical Chronic Myeloid Leukemia," Blood, 2018, 132(Suppl 1):350.
Database accession No. RN 1795440-67-3, Chemical Abstracts Service, Jul. 6, 2015, 1 page.
Davis et al., "Small Molecule Dual Antagonist of Pim 1 and 3 Kinases Ameliorate Experimental Autoimmune Encephalomyelitis," 26th Congress of the European Committee for Treatment and Research in Multiple Sclerosis, Oct. 13-16, 2010, Gothenburg, Sweden, Poster P436.
De Paiva et al., "IL-17 disrupts corneal barrier following desiccating stress," Mucosal Immunol., 2009, 2(3):243-53.
De Vos et al., "JAK2 tyrosine kinase inhibitor tyrphostin AG490 downregulates the mitogen-activated protein kinase (MAPK) and signal transducer and activator of transcription (STAT) pathways and induces apoptosis in myeloma cells.," Br J Haematol, 2000, 109(4):823-828.
Deng Jun et al., "Rh-catalyzed asymmetric hydrogenation of gamma-phthalimido-substituted esters: an efficient enantioselective synthesis of beta-aryl-gamma-amino acids," Org. Lett., 2007, 9(23):4825-4827.
Deuse et al., "Novel Immunosuppression: R348, a JAK3- and Syk-Inhibitor Attenuates Acute Cardiac Allograft Rejection," Transplantation, 2008, 85(6):885-892.
Divkovic et al., "Hapten-protein binding: from theory to practical application in the in vitro prediction of skin sensitization," Contact Dermatitis, 2005, 189-200.
Doane, "An instrument for in vivo tear film interferometry," Optom Vis Sci, 1989, 66:383-388.
Doleschall et al., "Thermal and Acid Catalysed Degradations of 3-alkylthio-6,7-dihydro[1.2.4]triazino[1,6-c]quinazolin-5-ium-1-olates," Tetrahedron, 1974, 30:3997-4012.
Dorwald F. A. Side Reactions in Organic Synthesis, 2005, Wiley: VCH, Weinheim p. IX of Preface p. 1-15.
Dorwald, "Side Reactions in Organic Synthesis: A Guide to Successful Synthesis Design," Wiley-VCH, 2005, Chapter 1, 32 pages.
Dudley et al. "A VEGF/JAK2/STAT5 axis may partially mediate endothelial cell tolerance to hypoxia," Biochem. J., 2005, 390(Pt 2):427-36.
Ecuador Examination Report in Ecuador Application No. SP-08-8540, dated Jun. 13, 2017, 30 pages.
Edward B. Roche, "Bioreversible Carriers in Drug Design," American Pharmaceutical Association and Pergamon Press, 1987, Front Matter, 4 pages.
Eghtedar et al., "Phase 2 study of the JAK kinase inhibitor ruxolitinib in patients with refractory leukemias, including postmyeloproliferative neoplasm acute myeloid leukemia," Blood, May 2012, 119(20):4614-4618.
Eghtedar, "Phase II Study of the JAK2 Inhibitor, INCBO18424, in Patients with Refractory Leukemias Including Post-Myeloproliferative Disorder Acute Myeloid Leukemia," American Society of Hematology (ASH) annual meeting in Orlando, FL (Dec. 6, 2010), Abstract/poster 509.
Einmahl et al., "Therapeutic applications of viscous and injectable poly(ortho esters)," Adv. Drug. Deliv. Rev., 2001, 53:45-73.
Eliason et al., "Staining of the conjunctiva and conjunctival tear film," Br J Ophthalmol, 1990, 74:519-22.
Elliott et al., "WHO-defined chronic neutrophilic leukemia: a long-term analysis of 12 cases and a critical review of the literature," Leukemia, 2005, 19:313-317.
Eurasian Office Action in Eurasian Application No. 201291310, dated Mar. 9, 2017, 4 pages (English Translation).
Eurasian Office Action in Eurasian Application No. 201690458/28, dated Jan. 25, 2017, 11 pages (with English translation).
Eurasian Office Action in Eurasian Application No. 201890663/28, dated Dec. 10, 2018, 8 pages (with English translation).
Eurasian Search Report in Eurasian Application No. 201200132, dated Sep. 1, 2016, 6 pages (English Translation).

(56) References Cited

OTHER PUBLICATIONS

European Communication in European Application No. 06839328.5, dated Jan. 22, 2009, 5 pages.
European Communication in European Application No. 13798840.8, dated May 11, 2018, 5 pages.
European Communication pursuant to Article 94(3) EPC in European Application No. 14753182.6, dated Nov. 6, 2017, 10 pages.
European Communication pursuant to Article 94(3) EPC in European Application No. 14753182.6, dated Sep. 10, 2018, 7 pages.
European Office Action in European Application No. 14702389.9-1109, dated Jun. 11, 2018.
European Office Action in European Application No. 15195698.4, dated Mar. 15, 2017, 4 pages.
European Search Report in European Application No. 16197502.4, dated Mar. 20, 2017, 15 pages.
Expert Scientific Group on Phase One Clinical Trials Final Report, Nov. 30, 2006, pp. Cl, C35-C38.
Farrell et al., "A classification for dry eyes following comparison of tear thinning time with Schirmer tear test," Acta Ophthalmol (Copenh), 1992, 70(3):357-60.
Farrell et al., "A clinical procedure to predict the value of temporary occlusion therapy in keratoconjunctivitis sicca," Ophthal Physiol Opt, 2003, 23:1-8.
Farris, "Tear osmolarity—a new gold standard?" Adv Exp Med Biol, 1994, 350:495-503.
Fayad et al., "Interleukin-6 and interleukin-10 levels in chronic lymphocytic leukemia: correlation with phenotypic characteristics and outcome," Blood, Jan. 2001, 97(1): 256-263.
Fenaux et al., "A randomized phase 3 study of lenalidomide versus placebo in RBC transfusion-dependent patients with Low-/Intermediate-l-risk myelodysplastic syndromes with del5q," Blood, Oct. 2011, 118(14): 3765-76.
Fenaux et al., "Efficacy of azacitidine compared with that of conventional care regimens in the treatment of higher-risk myelodysplastic syndromes: a randomised, open-label, phase III study," Lancet Oncol, Mar. 2009, 10: 223-32.
Fiskus et al., "Synergistic Activity of Combinations of JAK2 Kinase Inhibitor with PI3K/mTOR, MEK or PIM Kinase Inhibitor Against Human Myeloproliferative Neoplasm Cells Expressing JAK2V617F" J. American Chem. Soc., 52nd Annual Meeting of the American-Society-of-Hematology (ASH); Orlando, FL, USA; Dec. 4-7, 2010, ACS Publications; vol. 116, No. 21 Nov. 1, 2010 p. 349, XP002667216, ISSN: 0002-7863 (1 page).
Fleischman et al., "The CSF3R T618I mutation causes a lethal neutrophilic neoplasia in mice that is responsive to therapeutic JAK inhibition," Blood, Nov. 2013, 122: 3628-3632.
Flex et al., "Somatically acquired JAK1 mutations in adult acute lymphoblastic leukemia," J. Exp Med., 2008, 205:751-8.
Fonseca et al., "Interleukin-6 as a key player in systemic inflammation and joint destruction," Autoimmunity Reviews, 2009, 8:538-42.
Forbes et al., "Synthesis and evaluation of a series of aryl [e] fused pyrazolo [4,3-c]pyridines with potential anxiolytic activity," J Medicinal Chem., Jan. 1, 1990, 33(9):2640-2645.
Foucar, "Myelodysplastic/Myeloproliferative Neoplasms," Am J Olin Pathol, 2009, 132:281-289.
Freshney, Culture of Animal Cells, A Manual of Basic Technique, Alan R. Liss, Inc., 1983, New York, P4.
Fridman et al. "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA. Abstract #3538, poster #757, Dec. 10, 2007 (1 page).
Fridman et al. "Selective JAK Inhibition is Efficacious against Multiple Myeloma Cells and Reverses the Protective Effects of Cytokine and Stromal Cell Support" Abstract #0956, presented Sunday, Jun. 15, 2008 at the European Hematology Association, 13th Congress, Jun. 12-15, Copenhagen, Denmark (1 page).
Fridman et al., "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007 (1 page).
Fridman et al., "Discovery and Preclinical Development of Selective JAK Inhibitors for the Treatment of Myeloproliferative Disorders" poster presented at the 4th International Congress on Myeloproliferative Diseases and Myelodysplastic Syndromes, New York, NY. Nov. 8-10, 2007, Poster 0009 (1 page).
Fridman et al., "Efficacy and Tolerability of Novel JAK Inhibitors in Animal Models of Rheumatoid Arthritis" poster presented at the ACR/ARHP (American College of Rheumatology/Association of Rheumatology Health Professionals) Scientific Meeting 2007, Boston, MA, Nov. 10, 2007, Abstract 1771, poster 285 (1 page).
Fridman et al., "Preclinical evaluation of local JAK1 and JAK2 inhibition in cutaneous inflammation," Journal of Investigative Dermatology, Sep. 2011, 131(9): 1838-1844.
Froberg et al., "Demonstration of clonality in neutrophils using FISH in a case of chronic neutrophilic leukemia," Leukemia, 1998, 12:623-626.
Fujihara et al., "Evaluation of human conjunctival epithelium by a combination of brush cytology and flow cytometry: an approach to the quantitative technique," Diagn Cytopathol, 1997, 17:456-60.
Fujii et al., "Aberrant expression of serine-threonine kinase Pim-3 in hepatocellular carcinoma development and its role in the proliferation of human hepatoma cell lines," Int. J. Canc., 2005, 114:209-18.
Fukagawa et al., "Histological evaluation of brush cytology of rabbit conjunctiva," Nippon Ganka Gakkai Zasshi, 1993, 97:1173-8 (contains English abstract within the article).
Furqan et al., "Dysregulation of JAK-STAT pathway in hematological malignancies and JAK inhibitors for clinical application," Biomarker Research 2013, 1(1):1-10.
Gaertner, "Cyclization of 1-Alkylamino-3-halo-2-alkanols to 1-Alkyl-3-azetidinols," J. Org. Chem., 1967, 32: 2972-76.
Gaestel et al., "Targeting innate immunity protein kinase signalling in inflammation," Nat Rev Drug Discov., Jun. 2009, 8(6):480-99.
Georg Pilz, "Modern multiple sclerosis treatment—what is approved, what is on the horizon" Drug Discovery Today Dec. 2008, vol. 13, Nos. 23/24 1013-1025.
Ghelardi et al., "A Mucoadhesive Polymer Extracted from Tamarind Seed Improves the Intraocular Penetration and Efficacy of Rufloxacin in Topical Treatment of Experimental Bacterial Keratitis," Antimicrob. Agents Chemother., 2004, 48:3396-3401.
Gilchrist et al., "5H-2-Pyrindines from 2-Bromocyclopentene-l-carboxaldehyde," Tetrahedron, Jan. 1, 1995, 9119-9126.
Glasson et al., "Differences in clinical parameters and tear film of tolerant and intolerant contact lens wearers," Invest Ophthalmol Vis Sci, 2003, 44:5116-5124.
Glattfeld, Improvements in the Preparation of DL-Threonic and DL-Erythronic Acids, J. Am. Chem. Soc., 1940, 62:974-977.
Gobbels et al., "Tear secretion in dry eyes as assessed by objective fluorophotometry.," Ger J Ophthalmol, 1992, 1:350-353.
Golding et al., "X-ray and scanning electron microscopic analysis of the structural composition of tear ferns," Cornea, Jan. 1994, 13(l):58-66.
Golub et al., "Molecular Classification of Cancer: Class Discovery and Class Prediction by Gene Expression Monitoring," Science, 1999, 286: 531-537.
Gomez-Abad et al., "PIM2 inhibition as a rational therapeutic approach in B-cell lymphoma," Blood, 2011, 118:5517-27.
Gomtsyan et al., "Design, synthesis, and structure-activity relationship of 6-alkynylpyrimidines as potent adenosine kinase inhibitors," J. Med. Chem., 2002, 45(17):3639-3648.
Goodman et al., "IL-6 Signaling in Psoriasis Prevents Immune Suppression by Regulatory T Cells," J. Immunol., Sep. 2009, 183: 3170-3176.
Gooseman et al., "The intramolecular b-fluorine . . . ammonium interaction in 4- and 8-membered rings," Chem. Commun, 2006, 30:3190-3192.
Gorre et al., "Clinical Resistance to STI-571 Cancer Therapy Caused by BCR-ABL Gene Mutation or Amplification," Science, 2001, 293:876-880.

(56) References Cited

OTHER PUBLICATIONS

Goto et al., "Color mapping of tear lipid layer thickness distribution from the image analysis in DR-1 tear lipid layer interference images," ARVO abstract, 2004, 2 pages.

Goto et al., "Computer-synthesis of an interference color chart of human tear lipid layer by a colorimetric approach," Invest Ophthalmol Vis Sci, 2003, 44:4693-7.

Goto et al., "Differentiation of lipid tear deficiency dry eye by kinetic analysis of tear interference images," Arch Ophthalmol, 2003, 121:173-80.

Goto et al., "Evaluation of the tear film stability after laser in situ keratomileusis using the tear film stability analysis system," Am J Ophthalmol, Jan. 2004, 137(1):116-20.

Goto et al., "Kinetic analysis of tear interference images in aqueous tear deficiency dry eye before and after punctal occlusion," Invest Ophthalmol Vis Sci, 2003, 44:1897-905.

Goto et al., "Tear Film Stability Analysis System: Introducing a new application for videokeratography," Cornea, Nov. 2004, 23(8):S65-S70.

Gottlieb, "Psoriasis: Emerging Therapeutic Strategies," Nat Rev Drug Disc., Jan. 2005, 4:19-34.

Gottlieb, Alice, Presentation at the 2008 American Academy of Dermatology, 66th Annual Meeting, San Antonio, TX, Feb. 1, 2008, symposium-303 (12 pp.).

Gozgit et al., "Effects of the JAK2 Inhibitor, AZ960, on Pim/BAD/BCL-xL Survival Signaling in the Human JAK2 V617F Cell Line SET-2," Journal of Biological Chemistry, Nov. 2008, 283(47): 32334-32343.

Grabbe et al., "Immunoregulatory mechanisms involved in elicitation of allergic—contact hypersensitivity," Immunol Today, Jan. 1998, 19(1):37-44 (only 1 page provide and marked "best available copy").

Green and Wuts, P.G.M.. Protective Groups in Organic Synthesis, 3rd. Ed., Wiley & Sons, Inc., New York (1999) **Too Voluminous to Provide.

Greenberg, "The Role of Hemopoietic Growth Factors in the Treatment of Myelodysplastic Syndromes," International Journal of Pediatric Hematology/Oncology, 1997, 4(3): 231-238.

Greenberg, "The myelodysplastic syndromes" in Hoffman, et al., eds. Hematology: Basic Principles and Practice (3rd ed.), Churchill Livingston; 2000:1106-1129.

Greene et al., Greene's Protective Groups in Organic Synthesis, 2007, 4th Edition, 54-55.

Gregory et al., "Clinical and laboratory features of myelofibrosis and limitations of current therapies," Clinical Advances in Hematology and Oncology, (Sep. 2011) vol. 9, No. 9, pp. 1-3.

Grivennikov, et al., "IL-6 and STAT3 are required for survival of intestinal epithelial cells and the development of colitis-associated cancer," Cancer Cell, 15:103-111 (2009).

Groneberg et al., "Animal models of allergic and inflammatory conjunctivitis," Allergy, 2003, 58, 1101-1113.

Grossman et al., "Interleukin 6 is expressed in high levels in psoriatic skin and stimulates proliferation of cultured human keratinocytes," Proc. Natl. Acad., Sci. USA, Aug. 1989, 86: 6367-6371.

Gu and Li, "A concise synthesis of (2S,4R)- and (2S,4S)-4-methylglutamic acid," Tetrahedron Lett., 2003, 44:3203-3205.

Guillon, "Tear film photography and contact lens wear," J Br Contact Lens Assoc, 1982;5:84-7.

Guo et al., "Overexpression of Pim-1 in bladder cancer," J. Experimental & Clinical Cancer Research, 2010, 29: 161-167.

Gura, "Systems for Identifying New Drugs Are Often Faulty," Science, Nov. 1997, 278(5340): 1041-1042.

Gurram et al., "C-C Cross-Coupling Reactions of )6-Alkyl-2-Haloinosine Derivatives and a One-Pot Cross-Coupling/)6-Deprotection Procedure," Chem Asian J., Aug. 2012, 7(8):1853-1861.

Guschin et al., "A major role for the protein tyrosine kinase JAK1 in the JAK/STAT signal transduction pathway in response to interleukin-6," Embo J 14:1421-1429 (1995).

Hammerman et al., "Lymphocyte Transformation by Pim-2 Is Dependent on Nuclear Factor-kB Activation," Cancer Research, Nov. 2004, 64: 8341-8348.

Hamze' et al., "Synthesis of Various 3-Substituted 1,2,4-Oxadiazole-Containing Chiral β3 - and r-Amino Acids from Fmoc-Protected Aspartic Acid," J. Org. Chem., 2003, 68(19), pp. 7316-7321.

Hardwicke, et al., "GSK1070916, a potent Aurora B/C kinase inhibitor with broad antitumor activity in tissue culture cells and human tumor xenograft models," Molecular Cancer Therapeutics 8(7), 1808-1817 (2009).

Harris et al., "Alkyl 4-Chlorobenzoyloxycarbamates as Highly Effective Nitrogen Source Reagents for the Base-Free, Intermolecular Aminohydroxylation Reaction," J. Org. Chem., 2011, 76:358-372.

Harris et al., "World Health Organization classification of neoplastic diseases of the hematopoietic and lymphoid tissues: report of the Clinical Advisory Committee meeting-Airlie House, Virginia, Nov. 1997," J Clin Oncol, 1999, 17:3835-3849.

Heine et al., "The JAK-inhibitor ruxolitinib impairs dendritic cell function in vitro and in vivo," Blood, 2013, 122(7): 1192-1202.

Helal et al., "Stereoselective Synthesis of cis-1,3-Disubstituted Cyclobutyl Kinase Inhibitors," Organic Letters, 2004, 6(11): 1853-1856.

Hengge et al., "Adverse Effects of Topical Glucocorticosteroids," J Am Acad Dermatol., Jan. 2006, 54(1):1-15.

Hernandez et al., "Clinical, hematological and cytogenetic characteristics of atypical chronic myeloid leukemia," Ann. Oncol., Apr. 2000, 11(4):441-444.

Hickenbottom "Reactions of organic compounds," State Scientific-Technical Publishing Association, Chemical Literature Section, Moscow, 1939, pp. 360-362.

Higuchi et al., "Pro-drugs as Novel Delivery Systems," vol. 14 of the A.C.S. Symposium Series (1975)* too voluminous to provide.

Holly et al., "Lacrimation kinetics in Humans as determined by a novel technique," in Holly FJ (ed). The preocular tear film. Lubbock TX, Lubbock Dry Eye Institute, 1986, pp. 76-88).

Hong et al., "Total Synthesis of Onnamide A," J. Am. Chem. Soc., 1991, 113:9693-94.

Hsi et al., "Ki67 and PIM1 expression predict outcome in mantle cell lymphoma treated with high dose therapy, stem cell transplantation and rituximab: a Cancer and Leukemia Group B 59909 correlative science study," Leuk. Lymph., 2008, 49:2081-2090.

Hsu et al., "Pim-1 knockdown potentiates paclitaxel-induced apoptosis in human hormone-refractory prostate cancers through inhibition of NHEJ DNA repair," Cancer Lett., 2012, 319:214-222.

Hu et al., "PIM-1—specific mAb suppresses human and mouse tumor growth by decreasing PIM-1 levels, reducing Akt phosphorylation and activating apoptosis," J. Clinical Investigation, Feb. 2009, 119(2):362-375.

Huang et al., "Combination of PIM and JAK2 inhibitors synergistically suppresses cell proliferation and overcomes drug resistance of myeloproliferative neoplasms," Oncontarget, May 8, 2014, 5(10):3362-3374.

Huang et al., "Structure-based design and optimization of 2-aminothiazole-4-carboxamide as a new class of CHK1 inhibitors," Bioorganic Med Chem Lett., Mar. 2013, 23(9):2590-2594.

Huang, "Inhibition of STAT3 activity with AG490 decreases the invasion of human pancreatic cancer cells in vitro," Cancer Sci. 97(12): 1417-23 (2006).

Hungarian Office Action in Hungarian Application No. S1700017/5, dated Aug. 28, 2018, 5 pages.

Huttel, et al., "Lithium pyrazole compounds," Liebigs Ann. Chem. Bd., 625:55-65 (1959) (abstract provided).

Hyung-Bae et al., "CP-690550, a Janus Kinase Inhibitor, Suppresses CD4+ T-Cell-Mediated Acute Graft-Versus-Host Disease by Inhibiting the Interferon-Y Pathway," Transplantation, 2010, 90(8):825-835.

Indian Office Action in Indian Application No. 201627008738, dated May 16, 2019, 6 pages.

Indian Office Action in Indian Application No. 2177/DELNP/2014, dated May 8, 2018, 4 pages.

(56) References Cited

OTHER PUBLICATIONS

International Preliminary Report on Patentability (with Written Opinion) dated Nov. 22, 2011 for International Appln. No. PCT/US2010/035728, 8 pages.
International Preliminary Report on Patentability (with Written Opinion) dated Nov. 22, 2011 for International Appln, No. PCT/US2010/035783, 5 pages.
International Preliminary Report on Patentability (with Written Opinion) in International Application No. PCT/US2006/047369, dated Jun. 18, 2008, 10 pages.
International Preliminary Report on Patentability (with Written Opinion) in International Application No. PCT/US2010/047252, dated Mar. 6, 2012, 7 pages.
International Preliminary Report on Patentability for International Appln. No. PCT/US2008/066662 dated Dec. 17, 2009, 7 pages.
International Preliminary Report on Patentability for PCT/US2008/66658 dated Dec. 17, 2009, 7 pages.
International Preliminary Report on Patentability for PCT/US2009/036635 dated Sep. 14, 2010, 6 pages.
International Preliminary Report on Patentability for PCT/US2009/059203 dated Apr. 5, 2011, 6 pages.
International Preliminary Report on Patentability for PCT/US2010/021003 dated Jul. 19, 2011, 11 pages.
International Preliminary Report on Patentability for PCT/US2010/052011 dated Apr. 11, 2012, 4 pages.
International Preliminary Report on Patentability for PCT/US2011/025433 dated Aug. 21, 2012, 7 pages.
International Preliminary Report on Patentability for PCT/US2011/027665 dated Sep. 11, 2012, 7 pages.
International Preliminary Report on Patentability for PCT/US2011/037291 dated Nov. 27, 2012, 7 pages.
International Preliminary Report on Patentability for PCT/US2011/061351 dated May 30, 2013, 7 pages.
International Preliminary Report on Patentability for PCT/US2011/061374 dated May 30, 2013, 5 pages.
International Preliminary Report on Patentability for PCT/US2012/043099 dated Dec. 23, 2013, 6 pages.
International Preliminary Report on Patentability for PCT/US2012/050210 dated Feb. 11, 2014, 8 pages.
International Preliminary Report on Patentability for PCT/US2012/051439 dated Feb. 27, 2014, 7 pages.
International Preliminary Report on Patentability for PCT/US2012/053921 dated Mar. 20, 2014, 8 pages.
International Preliminary Report on Patentability for PCT/US2013/041601, dated Nov. 18, 2014, 7 pages.
International Preliminary Report on Patentability in International Application No. PCT/US2014/011486, dated Jul. 21, 2015, 7 pages.
International Preliminary Report on Patentability in International Application No. PCT/US2014/011487, dated Jul. 23, 2015, 6 pages.
International Preliminary Report on Patentability in International Application No. PCT/US2014/049940, dated Feb. 9, 2016, 9 pages.
International Preliminary Report on Patentability in International Application No. PCT/US2014/051678, dated Mar. 3, 2016, 15 pages.
International Preliminary Report on Patentability in International Application No. PCT/US2014/052214, dated Feb. 23, 2016, 7 pages.
International Preliminary Report on Patentability in International Application No. PCT/US2015/028224, dated Nov. 10, 2016, 7 pages.
International Preliminary Report on Patentability in International Application No. PCT/US2015/040146, dated Jan. 17, 2017, 8 pages.
International Preliminary Report on Patentability in International Application No. PCT/US2016/034520, dated Dec. 14, 2017, 7 pages.
International Preliminary Report on Patentability in International Application No. PCT/US2016/050925, dated Mar. 22, 2018, 8 pages.
International Search Report and the Written Opinion, PCT/US2012/051439, dated Nov. 30, 2012, 15 pages.
International Search Report and the Written Opinion, PCT/US2012/053921, dated Nov. 7, 2012, 19 pages.
International Search Report and Written Opinion dated Feb. 9, 2010 for International Appln. No. PCT/US2009/059203, 10 pages.
International Search Report and Written Opinion for International Appln. No. PCT/US2005/046207 dated May 15, 2007, 6 pages.
International Search Report and Written Opinion for International Appln. No. PCT/US2008/066662 dated Dec. 23, 2008, 11 pages.
International Search Report and Written Opinion for International Appln. No. PCT/US2009/036635 dated Jun. 3, 2009, 14 pages.
International Search Report and Written Opinion for PCT/US2006/047369, 16 pages (dated Apr. 24, 2007).
International Search Report and Written Opinion for PCT/US2008/083319, 29 pages dated Mar. 13, 2009.
International Search Report and Written Opinion for PCT/US2011/025433, 12 pages (dated Jul. 20, 2011).
International Search Report and Written Opinion for PCT/US2011/027665 dated Jun. 27, 2011, 14 pages.
International Search Report and Written Opinion for PCT/US2011/037291, 11 pages (dated Apr. 19, 2012).
International Search Report and Written Opinion for PCT/US2011/061351 dated Feb. 17, 2012, 12 pages.
International Search Report and Written Opinion for PCT/US2011/061374 dated Mar. 27, 2012, 12 pages.
International Search Report and Written Opinion for PCT/US2012/025581, 16 pages (dated Apr. 26, 2012).
International Search Report and Written Opinion for PCT/US2012/043099, 11 pages (dated Sep. 13, 2012).
International Search Report and Written Opinion for PCT/US2012/050252 dated Jan. 2, 2013, 17 pages.
International Search Report and Written Opinion in International Application No. PCT/US2013/067794, dated Dec. 17, 2013, 14 pages.
International Search Report and Written Opinion in International Application No. PCT/US2014/011486, dated Mar. 17, 2014, 12 pages.
International Search Report and Written Opinion in International Application No. PCT/US2014/011487, dated Apr. 4, 2014, 11 pages.
International Search Report and Written Opinion in International Application No. PCT/US2014/020554, dated Jul. 16, 2014, 17 pages.
International Search Report and Written Opinion in International Application No. PCT/US2014/049940, dated Nov. 4, 2014, 13 pages.
International Search Report and Written Opinion in International Application No. PCT/US2014/051678, dated Feb. 11, 2015, 22 pages.
International Search Report and Written Opinion in International Application No. PCT/US2014/052214, dated Oct. 28, 2014, 13 pages.
International Search Report and Written Opinion in International Application No. PCT/US2015/017963, dated Jun. 5, 2015, 13 pages.
International Search Report and Written Opinion in International Application No. PCT/US2015/028224, dated Jul. 21, 2015, 9 pages.
International Search Report and Written Opinion in International Application No. PCT/US2015/033254, dated Oct. 7, 2015, 12 pages.
International Search Report and Written Opinion in International Application No. PCT/US2015/040146, dated Oct. 5, 2015, 12 pages.
International Search Report and Written Opinion in International Application No. PCT/US2016/034520, dated Jul. 12, 2016, 11 pages.
International Search Report and Written Opinion in International Application No. PCT/US2016/050925, dated Oct. 21, 2016, 13 pages.
International Search Report and Written Opinion in International Application No. PCT/US2016/054779, dated Dec. 9, 2016, 12 pages.

(56) References Cited

OTHER PUBLICATIONS

International Search Report and Written Opinion in International Application No. PCT/US2018/064534, dated Mar. 11, 2019, 12 pages.
International Search Report for PCT/US2008/66658 dated Dec. 23, 2008, 4 pages.
International Search Report for PCT/US2010/021003 dated Aug. 16, 2010, 8 pages.
International Search Report for PCT/US2010/035728 dated Jul. 8, 2010, 3 pages.
International Search Report for PCT/US2010/035783 dated Aug. 23, 2010, 4 pages.
International Search Report for PCT/US2010/047252 dated Nov. 17, 2010, 4 pages.
International Search Report for PCT/US2010/052011 dated Nov. 30, 2010, 3 pages.
International Search Report in International Application No. PCT/US2013/041601, dated Sep. 3, 2013, 3 pages.
Iranpoor, "A Rapid and Facile Conversion of Primary Amides and Aldoximes to Nitriles and Ketoximes to Amides with Triphenylphosphine and N-Chlorosuccinimide," G Syn., 2002, Commun 32:2535-41.
Irino et al., "JAK2 V617F-Dependent Upregulation of PU.1 Expression in the Peripheral Blood of Myeloproliferative Neoplasm Patients," PLOS One, Jul. 2011, 6(7):e22148.
Isaac et al., "The oncogenic PIM kinase family regulates drug resistance through multiple mechanisms," Drug Resis. Updates, 2011, 14:203-11.
Ishchenko et al., "Structure-based design of low-nanomolar PIM kinase inhibitors," Bioorg Med Chem Lett., 2015, 25:474-480.
Ishizaki et al., "Pharmacological Properties of Y-27632, a Specific Inhibitor of Rho-Associated Kinases," Molecular Pharmacology, 2000, 57, 976-983.
Israeli Office Action in Israel Application No. 244,224, dated May 18, 2018, 8 pages (English Translation).
Israeli Office Action in Israeli Application No. 239,886, dated Apr. 2, 2019, 4 pages.
Itagaki et al, "Expedient Synthesis of Potent Cannabinoid Receptor Agonist (-)-CP55,940," Organic Letters, 2005, 7(19): 4181-4183.
Jädersten et al., "Long-term outcome of treatment of anemia in MDS with erythropoietin and G-CSF," Blood, Aug. 2005, 106(3): 803-11.
James et al., "A unique clonal JAK2 mutation leading to constitutive signalling causes polycythaemia vera," Nature, 434 (7037): 1144-8 (2005).
Janes et al., "Effective and selective targeting of leukemia cells using a TORC1/2 kinase inhibitor.," Nature Medicine (2010) LNKD-PUBMED:20072130, vol. 16, No. 2, pp. 205-213 XP002673719.
Japanese Office Action in Japanese Application No. 2013-540049, dated Aug. 11, 2015, 3 pages (English Translation).
Japanese Office Action in Japanese Application No. 2015-042933, dated Feb. 2, 2016, 6 pages (English Translation).
Japanese Office Action in Japanese Application No. 2015-219637, dated Oct. 4, 2016, 6 pages.
Japanese Office Action in Japanese Application No. 2015-241393, dated Sep. 27, 2016, 5 pages (English Translation).
Japanese Office Action in Japanese Application No. 2015-552896, dated Nov. 28, 2017, 8 pages (English Translation).
Japanese Office Action in Japanese Application No. 2015-561582, dated Feb. 13, 2018, 9 pages (English Translation).
Japanese Office Action in Japanese Application No. 2016-143513, dated May 23, 2017, 3 pages (English Summary).
Japanese Office Action in Japanese Application No. 2016-536470, dated Apr. 24, 2018, 4 pages (English Translation).
Japanese Office Action in Japanese Application No. 2017-000685, dated Jan. 31, 2017, 7 pages (with English translation).
Japanese Office Action in Japanese Application No. 2017-246-134, dated Oct. 16, 2018, 12 pages.
Jee et al., "Overview: animal models of osteopenia and osteoporosis," J Musculoskel. Neuron, Interact., 2001, 1(3):193-207.

Jester et al., "In vivo biomicroscopy and photography of meibomian glands in a rabbit model of meibomian gland dysfunction," Invest Ophthalmol Vis Sci, 1982, 22:660-7.
Jiang et al., "3,5-Disubstituted quinolines as novel c-Jun N-terminal kinase inhibitors," Bioorganic & Medicinal Chemistry Letters, 2007, 17: 6378-6382.
Jin et al., "Expressions of Osteopontin (OPN), anb3 an Pim-1 Associated with Poor Prognosis in Non-small Cell Lung Cancer (NSCLC)," Chin J. Cancer Res, 2012, 24(2): 103-108.
Johnson et al., "Relationship between drug activity in NCI preclinical in vitro and in vivo models and early clinical trials" British Journal of Cancer, 2001, 84, 1424-1437.
Johnson et al., "The effect of instilled fluorescein solution volume on the values and repeatability of TBUT measurements," Cornea, 2005, 24:811-7.
Kaddis et al., "Second-Line Treatment for Pancreatic Cancer," Journal of the Pancreas, Jul. 2014, XP055147286, Retrieved from the Internet: URL: http://www.serena.unina.it/index.php/jop/article/viewFile/2691/2737 [retrieved on Oct. 17, 2014].
Kaercher, "Ocular symptoms and signs in patients with ectodermal dysplasia syddromes," Graefe's Arch Clin Exp Ophthalmol, 2004, 495-500.
Kamb, "What's wrong with our cancer models?," Nature Reviews, Feb. 2005, 161-165.
Kantarjian et al., "Decitabine improves patient outcomes in myelodysplastic syndromes: results of phase III randomized study," Cancer, Apr. 2006, 106(8): 1794-803.
Katano et al., "Synthesis and biological activity of (cyclopentenopyridinium)thiomethylcephalosporins," The Journal of Antibiotics, Jan. 1990, 43(9): 1150-1159.
Kaushansky, "Lineage-Specific Hematopoietic Growth Factors," NEJM, 2006, 354:2034-45.
Kawamura et al., "Molecular cloning of L-JAK, a Janus family protein-tyrosine kinase expressed in natural killer cells and activated leukocytes," Proc Natl Acad Sci USA, 1994, 91(14): 6374-8.
Kelly et al., "Targeting PIM kinase activity significantly augments the efficacy of cytarabine," British Journal of Haematology, 2011, 156: 129-152.
Kharas et al., "ABL Oncogenes and Phosphoinositide 3-Kinase: Mechanism of Activation and Downstream Effectors," Cancer Res., Mar. 2005, 65(6):2047-2053.
Killedar et al., "Early pathogenic events associated with Sjogren's syndrome (SjS)-like disease of the NOD mouse using microarray analysis," Lab Invest, Dec. 2006, 86(12): 1243-1260.
Kim et al., "Clinical significances of preoperative serum interleukin-6 and C-reactive protein level in operable gastric cancer," BMC Cancer, May 20, 2009, 9(155):1-9.
Kim et al., "Zinc-Modified Cyanoborohydride as a Selective Reducing Agent," J. Org. Chem., 1985, 50: 1927-1932.
Kim et al., Abstract #1956, "A Phase 2, Randomized, Dose-Ranging, Vehicle-and Active-Controlled Study to Evaluate the Safety and Efficacy of Ruxolitinib Cream in Adult Patients with Atopic Dermatitis," Presentation, Presented at the 27th European Academy of Dermatology and Venereology Congress, Sep. 12-16, 2018, Paris, France, 11 pages.
King-Smith et al., "Three interferometric methods for measuring the thickness of layers of the tear film," Optom Vis Sci, 1999, 76:19-32.
Kirschner, "PIM Kinase Inhibitor AZD1208 for Treatment of MYC-Driven Prostate Cancer," JNCI J Natl Cancer Inst, 2015, 107(2): 1-11.
Kiss, "Recent developments on JAK2 inhibitors: A patent review," Expert Opinion on Therapeutic Patents, Apr. 2010, 20(4):471-495.
Kojima et al., "A new noninvasive tear stability analysis system for the assessment of dry eyes," Invest Ophthalmol Vis Sci, 2004, 45(5):1369-74.
Kola, "Can the pharmaceutical industry reduce attrition rates?" Nature Reviews Drug Discovery, 2004, 3:711-715.
Komuro et al., "Assessment of meibomian gland function by a newly developed laser meibometer," Adv Exp Med Biol, 2002, 506:517-520.

(56) References Cited

OTHER PUBLICATIONS

Konstantinos Markrilakis "Pathophysiology of Type 2 diabetes" Chapter 3 in Diabetes in Clinical Practice: Questions and Answers from Case Studies, Nicholas Katsilambros et al. eds. John Wiley & Sons: 2006, pp. 43-58.
Kontzias et al., "Jakinibs: a new class of kinase inhibitors in cancer and autoimmune disease," Curr. Opin. Pharm., 2012, 12: 464-470.
Korb et al., "Increase in tear film lipid layer thickness following treatment of meibomian gland dysfunction," Adv Exp Med Biol, 1994, 350:293-8.
Korb et al., "The effect of two novel lubricant eye drops on tear film lipid layer thickness in subjects with dry eye symptoms," Optom Vis Sci, 2005, 82: 594-601.
Korean Office Action in Korean Application No. 10-2012-7033308, dated Mar. 21, 2017, 6 pages (English Translation Only).
Korean Office Action in Korean Application No. 10-2018-7025131, dated Oct. 31, 2018, 7 pages (English Translation Only).
Korolev et al., "Pd-EDTA as an efficient catalyst for Suzuki-Miyaura reactions in water," Tet. Lett., 2005, 46: 5751-5754.
Kortylewski et al., "Regulation of the IL-23 and IL-12 balance by Stat3 signaling in the tumor microenvironment," Cancer Cell, 2009, 15:114-123.
Kruh et al., "The complete coding sequence of arg defines the Abelson subfamily of cytoplasmic tyrosine kinases.," Proc. Natl. Acad. Sci., Aug. 1990, 87:5802-5806.
Kubinyi, "QSAR: Hansch Analysis and Related Approaches," Methods and Principles in Medicinal Chemistry, Manhold, R. ed. Weinheim, NY, 1993, 42 pages.
Kudelacz et al. "The JAK-3 inhibitor CP-690550 is a potent anti-inflammatory agent in a murine model of pulmonary eosinophilia," European Journal of Pharmacology, 2008, 582: 154-161.
Kuppens et al., "Basal tear turnover and topical timolol in glaucoma patients and healthy controls by Fluorophotometry," Invest Ophthalmol Vis Sci, 1992, 33:3442-3448.
Kurzrock et al., "Serum Interleukin 6 Levels Are Elevated in Lymphoma Patients and Correlate with Survival in Advanced Hodgkin's Disease and with B Symptoms," Cancer Res., May 1993, 52: 2118-2122.
Kurzrock et al., "A Phase I, Open-Label Study of Siltuximab, an Anti-IL-6 Monoclonal Antibody, in Patients with B-cell Non-Hodgkin Lymphoma, Multiple Myeloma, or Castleman Disease," Clin. Cancer Res., published online May 9, 2013, 39 pages.
Kuster, "Kinase Inhibitors," Methods and Protocols, 2012, 46 pages.
Lai et al., "Mechanistic Study on the Inactivation of General Acyl-CoA Dehydrogenase by a Metabolite of Hypoglycin A," J. Am. Chem. Soc., 1991, 113: 7388-7397.
Lala et al., "Role of nitric oxide in tumor progression: Lessons from experimental tumors," Cancer and Metastasis Reviews, 1998, 17: 91-106.
Lam et al., "Tear Cytokine Profiles in Dysfunctional Tear Syndrome," Am J Ophthalmol., 2009, 147(2):198-205.
Lam et al., "New aryl/heteroaryl C N bond cross-coupling reactions via arylboronic acid/cupric acetate arylation," Tetrahedron Letters, May 1998, 39(19): 2941-2944.
Larock, "Comprehensive Organic Transformations," Wiley-VCH, 2nd Ed. (1999) pp. 1949-1950, 1958-1959, 1976, and 1983-1985.
Larson, "Myelodysplasia: when to treat and how," Best Pract Res Clin Haematol, 2006, 19(2): 293-300.
Lasho et al., "Chronic neutrophilic leukemia with concurrent CSF3R and SETBP1 mutations: single colony clonality studies, in vitro sensitivity to JAK inhibitors and lack of treatment response to ruxolitinib," Leukemia, 2014, 3 pages.
Leaf, "Why are we losing the war on cancer (and how to win it)," Clifton, Health Administrator vol. XVII, 2005, 1:172-183.
Lee et al., "Ruxolitinib Used to Treat Hypereosinophilic Syndrome," Blood, 2016, 128:5500.
Lemp "Report of National Eye Institute/Industry Workshop on clinical trials in dry eyes," CLAO J, 1995, 21:221-232.

Lemp et al., "Corneal desiccation despite normal tear volume," Ann Ophthalmol, 1970 (2) pp. 258-261 & 284.
Lemp et al., "The Definition and Classification of Dry Eye Disease: Report of the Definition and Classification Subcommittee of the International Dry Eye Workshop," The Ocular Surface, 5(2), 75-92 Apr. 2007.
Letter translation of Office Action, Chilean Application No. 3496-2006 as received from the foreign associate (Jul. 5, 2010) (4 pages).
Levine et al., "Activating mutation in the tyrosine kinase JAK2 in polycythemia vera, essential thrombocythemia, and myeloid metaplasia with myelofibrosis," Cancer Cell, 2005, 7:387-397.
Levitzki, "Tyrosine kinases as targets for cancer therapy," Eur. J. Cancer, 2002, 38(suppl. 5):S11-S18.
Levy et al. "INCB018424 A Selective Janus Kinase 1/2 Inhibitor" Presentation at the 50th American Society of Hematology Annual Meeting (ASH), Dec. 8, 2008, 27 pages.
Li et al., "Pim-3, a Proto-Oncogene with Serine/Threonine Kinase Activity, is Aberrantly Expressed in Human Pancreatic Cancer and Phosphorylates Bad to Block Bad-Mediated Apoptosis in Human Pancreatic Cancer Cell Lines," Canc. Res., 2006, 66:6741-7.
Li et al., "The synthesis and the antitumor activity of 5,7-disubstituted pyrazolo [1,5-a] pyrimidines," Chinese J Med Chem., Feb. 28, 2007, 17(1):18-22.
Liesveld and Lichtman, Chapter 88. "Myelodysplastic Syndromes (Clonal Cytopenias and Oligoblastic Myelogenous Leukemia)," in Prchal et al., eds. Williams Hematology. 8th ed., New York: McGraw-Hill; 2010.
Lima and Barreiro, "Bioisosterism: a useful strategy for molecular modification and drug design," Curr Med Chem., 2005, 12(1):23-49.
Lin et al., "A small molecule inhibitor of Pim protein kinases blocks the growth of precursor T-cell lymphoblastic leukemia/lymphoma," Blood, Jan. 2010, 115(4): 824-833.
Lin et al., "Enantioselective synthesis of Janus kinase inhibitor INCB018424 via an organocatalytic aza-Michael reaction," Organic Letters, 2009, 11(9): 1999-2002.
Lin, "Constitutive Activation of JAK3/STAT3 in Colon Carcinoma Tumors and Cell Lines," Am J Pathol., 2005, 167(4):969-80.
Ling et al., "Knockdown of STAT3 Expression by RNA Interference Inhibits the Induction of Breast Tumors in Immunocompetent Mice," Cancer Res, Apr. 2005 65:2532.
List et al., "Efficacy of lenalidomide in myelodysplastic syndromes," N Engl J Med, Feb. 2005, 352(6): 549-57.
Liu et al., "Overexpression of Pim-1 is associated with poor prognosis in patients with esophageal squamous cell carcinoma," J. Surg. Oncol., 2010,102:683-88.
Liu et al., "Synthesis and SAR of 1,9-dihydro-9-hydroxypyrazolo[3,4-b]quinolin-4-ones as novel, selective c-Jun N-terminal kinase inhibitors," Bioorganic & Medicinal Chemistry Letters, 2006, 16: 2590-2594.
Liu et al., "Combined Inhibition of Janus Kinase 1/2 for the Treatment of JAK2V617F-Driven Neoplasms: Selective Effects on Mutant Cells and Improvements in Measures of Disease Severity," Clin Cancer Res, 2009, 15(22):6891-6900.
Lu et al., "Pim2 is required for maintaining multiple myeloma cell growth through modulating TSC2 phosphorylation," Blood, Aug. 2013, 122(9): 1610-1620.
Lübbert et al., "Cytogenic responses in high-risk myelodysplastic syndrome following low-dose treatment with the DNA methylation inhibitor 5-aza-2'-deoxycytidine," Br J Haematol, Aug. 2001, 114(2): 349-57.
Lübbert et al., "Low-dose decitabine versus best supportive care in elderly patients with intermediate- or high-risk myelodysplastic syndrome (MDS) ineligible for intensive chemotherapy: final results of the randomized phase III study of the European Organisation for Research and Treatment of Cancer Leukemia Group and the German MDS Study Group," J Clin Oncol, May 2011, 29(15): 1987-96.
Lucet et al., "The structural basis of Janus kinas 2 inhibition by a potent and specific pan-Janus kinase inhibitor," Blood, 2006, 107(1):176-183.
Macchi et al., "Mutations of Jak-3 gene in patients with autosomal severe combined immune deficiency (SCID)," Nature, 1995, 377:65-8.

(56) References Cited

OTHER PUBLICATIONS

Madden et al., "Comparative study of two non-invasive tear film stability techniques," Curr Eye Res, 1994, 13(4):263-9.
Madhusudan et al., "Tyrosine kinase inhibitors in cancer therapy," Clin Biochem., 2004, 37(7):618-35.
Maffioli et al., "Mild and Reversible Dehydration of Primary Amides with PdC12 in Aqueous Acetonitrile," Organic Letters, 2005, 7(23): 5237-39.
Magnuson, "Why target PIM1 for cancer diagnosis and treatment?" Future Oncol., Sep. 2010, 6(9): 1461-1478.
Mahalingam et al., "Targeting PIM kinase enhances the activity of sunitinib in renal cell carcinoma," British J. Cancer, Oct. 2011, 105: 1563-1573.
Main et al., "High throughput synthesis of diverse 2,5-disubstituted indoles using titanium carbenoids bearing boronate functionality," Tetrahedron, 2007, 64(5):901-914.
Mainstone et al., "Tear meniscus measurement in the diagnosis of dry eye," Curr Eye Res, 1996, 15:653-661.
Malaysian Examination Report in Malaysian Application No. PI2013002970, dated May 31, 2016, 4 pages.
Mancini et al., "RAD 001 (everolimus) prevents mTOR and Akt late re-activation in response to imatinib in chronic myeloid leukemia.," J. Cellular Biochemistry (2010) LNKD-PUBMED:20014066, XP-002673720 vol. 109, No. 2 (2010) pp. 320-328.
Mandal, "Cancer Classification," 2014. Available from: <http://www.news-medical.net/health/Cancer-Classification.aspx, 6 pages.
Manjula et al., "Rapid Method of Converting Primary Amides to Nitriles and Nitriles to Primary Amides by ZnC12 using Microwaves under Different Reaction Conditions," Syn. Commun, 2007, 37:1545-50.
Manning et al., "The Protein Kinase Complement of the Human Genome," Science, 2002, 298(5600):1912-16 and 1933-34.
Mao et al., "Advances in research of tyrosine kinases inhibitor of vascular endothelial growth factor receptor," Chinese J New Drugs, Dec. 31, 2008, 17(7):544-550.
March, Jerry, Advanced Organic Chemistry: Reactions, Mechanisms, and Structure, 3rd ed., John Wiley & Sons: New York, pp. 845-855 (1985).
Marelli et al., "Tumor targeting via integrin ligands," Frontiers in Oncology, 2013, 1-12.
Marquardt et al., "Modification of tear film break-up time test for increased reliability" in Holly ed. The Preocular Tear Film in Health, Disease and Contact Lens Wear. Lubbock, Texas: Dry Eye Institute, 1986:57-63.
Martin-Sanchez et al., "HDAC inhibitors induce cell cycle arrest, activate the apoptotic extrinsic pathway and synergize with a novel PIM inhibitor in Hodgkin lymphoma-derived cell lines," British J. Haematology, 2010, 152:347-362.
Maruyama et al., "Effect of environmental conditions on tear dynamics in soft contact lens wearers," Invest Ophthalmol Vis Sci, 2004, 45(8):2563-8.
Mascarenhas et al., "Ruxolitinib: The First FDA Approved Therapy for the Treatment of Myelofibrosis," Clinical Cancer Research, Jun. 2012, 18(11): 3008-3014.
Matano et al., "Deletion of the long arm of chromosome 20 in a patient with chronic neutrophilic leukemia: cytogenetic findings in chronic neutrophilic leukemia," Am. J. Hematol., Jan. 1997, 54(1): 72-5.
Mathers et al., "Assessment of the tear film with tandem scanning confocal microscopy," Cornea, 1997;16:162-8.
Mathers et al., "Tear film changes associated with normal aging," Cornea, 1996; 15:229-334.
Mathers et al., "Tear flow and evaporation in patients with and without dry eye," Ophthalmology, 1996, 103:664-669.
Mathers et al., "Video imaging of the meibomian gland," Arch Ophthalmol, 1994, 112:448-9.
Mathers, "Evaporation from the ocular surface," Exp Eye Res, 2004, 78:389-394.

Maxson et al., "Oncogenic CSF3R Mutations in Chronic Neutrophilic Leukemia and Atypical CML," N. Engl. J. Med., 2013, 368(19):1781-1790.
Mayo Clinic. Available at: < http://www.mayoclinic.com/health/pancreatic-cancer/DS00357 >. 2 pages, retrieved from the Internet Apr. 3, 2013.
Mayo Clinic. Available at: < http://www.mayoclinic.com/health/prostate-cancer-prevention/MC00027 >. 3 pages, retrieved from the Internet Apr. 3, 2013.
Mayo Clinic. Available at: <http://www.mayoclinic.com/health/crohns-disease/DS00104/DSECTION=treatments-and-drugs> 6 pages, retrieved from the Internet May 27, 2013.
Mayo Clinic. Available at: <http://www.mayoclinic.com/health/multiple-sclerosis/DS00188/DSECTION=treatments-and-drugs>. 3 pages, retrieved from the Internet May 27, 2013.
Mayo Clinic. Available at: <http://www.mayoclinic.com/health/myasthenia-gravis/DS00375> 2 pages, retrieved from the Internet May 27, 2013.
Mayo Clinic. Available at: <http://www.mayoclinic.com/health/rheumatoid-arthritis/DS00020/DSECTION=treatments-and-drugs> 3 pages, retrieved from the Internet May 26, 2013.
Mayo Clinic. Available at: <http://www.mayoclinic.org/diseases-conditions/type-1-diabetes/basics/prevention> 2014, 19 pages.
MayoClinic.org, "Heart Transplant," 2018, [retrieved Dec. 8, 2018] retrieved from URL <https://www.mayoclinic.org/tests-procedures/heart-transplant/about/pac-20384750>, 18 pages.
Mazzacurati et al., "The PIM inhibitor AZD1208 synergizes with ruxolitinib to induce apoptosis of ruxolitinib sensitive and resistant JAK2-V617F-driven cells and inhibit colony formation of primary MPN cells," Oncotarget, Oct. 12, 2015, 6(37):40141-40157.
McMillan, "The systemic inflammation-based Glasgow Prognostic Score: a decade of experience in patients with cancer," Cancer Treat Rev, Aug. 2013, 39(5): 534-40.
McNamara et al., "Fluorometry in contact lens research: The next step," Optom Vis Sci, 1998, 75:316-322.
MD Anderson Cancer Center. "Leukemia Prevention and Screening," 2014, 2 pages.
MD Anderson Cancer Center. "Myeloproliferative Disease Prevention and Screening," 2014, 2 pages.
Mengher et al., "Non-invasive tear film break-up time: sensitivity and specificity," Acta Ophthalmol (Copenh), 1986, 64(4):441-4.
Merkel et al., "PIM1 kinase as a target for cancer therapy," Exp. Opin. Investig. Drugs, 2012, 21:425-38.
Mesa et al. "INCBO18424, A Selective JAK 1/2 Inhibitor, Significantly Improves the Compromised Nutritional Status and Frank Cachexia in Patients with Myelofibrosis (MF)" Poster #1760 at the American Society of Hematology Annual Meeting (ASH), Dec. 6, 2008 (19 pages).
Mesa et al., "Emerging drugs for the therapy of primary and post essential thrombocythemia, post polycythemia vera myelofibrosis," Expert Opinion on Emerging Drugs England, 2009, 14(3): 471-479.
Mesa et al., "Evaluating the serial use of the myelofibrosis symptom assessment form for measuring symptomatic improvement: Performance in 87 myelofibrosis patients on a JAK1 and JAK2 inhibitor (INCB018424) clinical trial," Cancer, Nov. 2011, 117(21): 4869-4877.
Meydan et al., "Inhibition of acute lymphoblastic leukaemia by a Jak-2 inhibitor," Nature, Feb. 1996, 379(6566):645-8.
Meyer et al., "Anti-inflammatory activity and neutrophil reductions mediated by the JAK1/JAK3 inhibitor, CP-690,550, in rat adjuvant-induced arthritis," Journal of Inflammation, 2010, 1-12.
Michelotti et al., "Two classes of p38a MAP kinase inhibitors having a common diphenylether core but exhibiting divergent binding modes," 2005, 15: 5274-5279.
Miethchen, "Micelle-activated reactions. I. Micelle-activated iodination and partial dehalogenation of pyrazoles and 1,2,4-triazoles," Journal F. prakt. Chemie, Band 331, Heft 5, S. 799-805 (1989) (1 page abstract also provided).
Mikkers et al., "High-throughput retroviral tagging to identify components of specific signaling pathways in cancer," Nature Genet., 2002, 32:153-159.

(56) References Cited

OTHER PUBLICATIONS

Mikkers et al., "Mice deficient for all PIM kinases display reduced body size and impaired responses to hematopoietic growth factors," Mol. Cell. Biol., 2004, 24:6104-15.

Milici et al., "Cartilage preservation by inhibition of Janus kinase 3 in two rodent models of rheumatoid arthritis," Arthritis Research & Therapy, 2008, 10:R14 (http://arthritis-research.com/content/10/1/R14) (9 pages).

Minegishi et al., "Human Tyrosine Kinase 2 Deficiency Reveals Its Requisite Roles in Multiple Cytokine Signals Involved in Innate and Acquired Immunity," Immunity, 2006, 25:745-55.

Mishchenko et al., "Treatment options for hydroxyurea-refractory disease complications in myeloproliferative neoplasms: JAK2 inhibitors, radiotherapy, splenectomy and transjugular intrahepatic portosystemic shunt," Eur J Haematol., Sep. 2010, 85(3): 192-9 Epub Jun. 2, 2010.

Mishima et al., "Determination of tear volume and tear flow," Invest Ophthalmol, 1966, 5:264-276.

Mishima, "Some physiological aspects of the precorneal tear film," Arch Ophthalmol, 1965, 73:233-241.

Mitsunobu, "The Use of Diethyl Azodicarboxylate and Triphenylphosphine in Synthesis and Transformation of Natural Products," Synthesis, 1981, (1): 1-28.

Miyata et al., "Stereospecific nucleophilic addition reactions to olefins.," J. Org. Chem., 1991, 56:6556-6564.

Miyaura et al., "Palladium-Catalyzed Cross-Coupling Reactions of Organoboron Compounds," Chem. Rev., 1995, 95: 2457-2483.

Miyazaki et al., "Design and effective synthesis of novel templates, 3,7-diphenyl-4-amino-thieno and furo-[3,2-c]pyridines as protein kinase inhibitors and in vitro evaluation targeting angiogenetic kinases," Bioorganic & Medicinal Chemistry Letters, 2007, 17: 250-254.

Miyoshi et al., "Interleukin-8 concentrations in conjunctival epithelium brush cytology samples correlate with neutrophil, eosinophil infiltration, and corneal damage," Cornea, 2001, 20:743-7.

Mizuki et al., "Suppression of myeloid transcription factors and induction of STAT response genes by AML-specific Flt3 mutations," Blood, 2003, 101:3164-73.

Molldrem et al., "Antithymocyte globulin for patients with myelodysplastic syndrome," Br J Haematol, Dec. 1997, 99(3): 699-705.

Moreland et al. "A Randomized Placebo-Controlled Study of INCB018424, a Selective Janus Kinase 1&2 (JAK 1&2) Inhibitor in Rheumatoid Arthritis (RA)" Presentation at the American College of Rheumatology meeting, Oct. 26, 2008, (20 pages).

Moriarty et al., "The synthesis and SAR of 2-amino-pyrrolo[2,3-d]pyrimidines: A new class of Aurora-A kinase inhibitors," Bioorganic and Medicinal Chemistry Letters, 2006, 16(22), 5778-5783.

Morwick, "Pim kinase inhibitors: a survey of the patent literature," Exp. Opin. Ther. Patents, 2010, 20(2): 193-212.

Mosby's Dictionary of Medicine, Nursing, & Health Professions, sicca complex, 2009, Elsevier, printed from http://www.credoreference.com/entry/ehsmosbymed/sicca_complex, 2 pages.

Mukaida et al., "Roles of Pim-3, a novel survival kinase, in tumorgenesis," Cancer Science, Aug. 2011, 102(8):1437-1442.

Mullighan et al., "JAK mutations in high-risk childhood acute lymphoblastic leukemia," Proc Natl Acad Sci USA, 2009, 106:9414-8.

Mulvihill et al., "Novel 2-phenylquinolin-7-yl-derived imidazo [1,5-a]pyrazines as potent insulin-like growth factor-I receptor (IFG-IR) inhibitors," Bioorganic & Medicinal Chemistry, 2008, 16: 1359-1375.

Mundle et al., "Evidence for Involvement of Tumor Necrosis Factor-α in Apoptotic Death of Bone Marrow Cells in Myelodysplastic Syndromes," Am J Hematol, 1999, 60:36-47.

Naka, "The paradigm of IL-6: from basic science to medicine," Arthritis Res., 2002, 4 Suppl 3:S233-42.

Nakagawara, "Trk receptor tyrosine kinases: A bridge between cancer and neural development," Cancer Letters, 2001, 169:107-114.

Nally et al., "Ocular discomfort and tear film break-up time in dry eye patients: A correlation," Invest Ophthalmol Vis Sci, 2000, 41:4:1436 (Poster Presentation).

Namour et al., "Once-daily High Dose Regimens of GLPG0634 in Healthy Volunteers are Safe and Provide Continuous Inhibition of JAK1 but not JAK2," ACR/ARHP Annual Meeting 12, Nov. 9-14, 2012, Abstract No. 1331.

Naqvi et al., "A potential role of ruxolitinib in leukemia," Expert Opinion on Investigational Drugs, Aug. 2011, 20(8): 1159-1166.

National Cancer Institute, "Cancer Types by Site," Mar. 14, 2011, [retrieved from Dec. 15, 2018] retrieved from URL <https://web.archive.org/web/20110314030905/https://training.seer.cancer.gov/disease/categories/site.html>, 3 pages.

National Cancer Institute, "FDA Approval for Ruxolitinib Phosphate," http://www.cancer.gov/cancertopics/druginfo/fda-ruxolitinibphosphate posted Nov. 18, 2011 (3 pages).

Naus et al., "6-(Het)aryl-7-Deazapurine Ribonucleosides as Novel Potent Cytostatic Agents," J. Med. Chem., 2010, 53(1):460-470.

NavigatingCancer.com "List of Cancer Chemotherapy Drugs," Navigating Care, [retrieved on Nov. 26, 2013] retrieved from URL <https://www.navigatingcancer.com/library/all/chemotherapy_drugs>, 6 pages.

Neidle Cancer Drug Design and Discovery, (Elsevier/Academic Press, 2008) 427-431.

Nelson et al., "Tear film osmolality determination: an evaluation of potential errors in measurement," Curr Eye Res, 1986, 5(9):677-81.

Neubauer et al., "Jak2 Deficiency Defines an Essential Developmental Checkpoint in Definitive Hematopoiesis," Cell, 1998, 93(3): 397-409.

Neuner et al., "Increased IL-6 Production by Monocytes and Keratinocytes in Patients with Psoriasis," J. Invest. Dermatol., 1991, 97: 27-33.

Nicholoff et al., "Recent Insights into the immunopathogenesis of psoriasis provide new therapeutic opportunities," J. Clin, Invest., 2004, 113: 1664-1675.

Nichols et al., "The lack of association between signs and symptoms in patients with dry eye disease," Cornea, 2004, 23(8):762-770.

Nichols et al., "The repeatability of clinical measurements of dry eye," Cornea, 2004, 23(3):272-85.

Nishimoto et al., "Improvement in Castleman's disease by humanized anti-interleukin-6 receptor antibody therapy," Blood, 2000, 95(1):56-61.

Nishio et al., "Tyrosine kinase-dependent modulation by interferon-α of the ATP-sensitive K+ current in rabbit ventricular myocytes," FEBS Letters, 1999, 445: 87-91.

Nitta et al., "Peptide-Titanium Complex as Catalyst for Asymmetric Addition of Hydrogen Cyanide to Aldehyde," J. Am. Chem. Soc., 1992, 114: 7969-75.

Norman, "Selective JAK1 inhibitor and selective Tyk2 inhibitor patents," Expert Opinion, Informa Healthcare. 2012, available at: <http://informahealthcare.com/dol/pdfplus/10.1517/13543776.2012.723693>.

Norn, "Quantitative tear ferning: Clinical investigations," Acta Ophthalmol (Copenh), 1994, 72(3):369-72.

Notice of Allowance and Fee(s) Due dated Sep. 21, 2007 in connection with U.S. Appl. No. 11/313,394, 6 pages.

Notice of Hearing and Preliminary Report for EP Patent 1966202, dated Mar. 18, 2013 (7 pages).

Ocana, A. "Preclinical development of molecular targeted agents for cancer" Nat. Rev. Clin. Oncol. 2011, 8, 200-209.

Office Action (Non-final) dated Aug. 22, 2007 in connection with U.S. Appl. No. 11/115,702, 9 pages.

Office Action (Non-final) dated Dec. 3, 2007 in connection with U.S. Appl. No. 11/524,641, 13 pages.

Office Action (Non-final) dated Feb. 25, 2009 for U.S. Appl. No. 12/137,892, 13 pages.

Office Action (Final) dated Feb. 7, 2008 for U.S. Appl. No. 11/115,702, 5 pages.

Office Action (Final) dated Jan. 29, 2014 in U.S. Appl. No. 13/043,986, 10 pages.

Office Action (Final) dated Nov. 30, 2009 for U.S. Appln. U.S. Appl. No. 12/137,892 (9 pgs.).

(56) References Cited

OTHER PUBLICATIONS

Office Action (Non-final) dated Apr. 20, 2007 in connection with U.S. Appl. No. 11/313,394, 16 pages.
Office Action in U.S. Appl. No. 14/186,338, dated May 5, 2014, 18 pages.
Office Action received for European Application No. 06 839 328.9 (dated Jan. 22, 2009), 5 pages.
Office Action received for Japanese Application No. 2008-545733 dated Oct. 11, 2011 (5 pages).
Office Action received for New Zealand Application No. 569015 dated Feb. 24, 2010, 2 pages.
Office Action received for Singapore Application No. 2008-04386-1 (dated Aug. 24, 2010).
Office Action received for Vietnamese Patent Application No. 1-2011-03188 dated Mar. 8, 2012 as translated by foreign associate (10 pages).
Office Action, Canadian Patent Office, Application No. 2,632,466, dated May 8, 2012, 3 pages.
Office Action, China, Patent Application No. 201080033308.6 dated Aug. 2, 2013, 10 pages.
Office Action, Eurasian Patent Office Application No. 200870048, dated Feb. 5, 2010.
Office Action, European Patent Office, Application No. 06 839 328.9 dated Oct. 21, 2010.
Office Action, European Patent Office, dated Nov. 6, 2009.
Office Action, Mexico, Patent Appl. No. MX/a/2008/007635 as received from foreign associate dated Jun. 15, 2010, 1 page.
Office Action, Mexico, Patent Appl. No. MX/a/2008/007635 as received from foreign associate dated Nov. 13, 2009, 4 pages.
Office Action/Examination Report received for Pakistan Application No. 211/2009 dated Jan. 18, 2010, 1 page.
Ogawa et al., "Insights from Pim 1 structure for anti-cancer drug design," Expert Opin Drug Discov, Dec. 2012, 7(12): 1177-92.
Oguz et al., "The height and radius of the tear meniscus and methods for examining these parameters," Cornea, 2000, 19:497-500.
Opposition for EP Patent 1966202, filed on Jun. 21, 2012, 30 pages.
Opposition for India Patent Application No. 2365/KOLNP/2008 dated Nov. 12, 2012 (received by Applicants from Indian associate on Apr. 17, 2013) 37 pages.
Opposition, Costa Rica, translation from Foreign Associate Dated Jun. 13, 2012, 6 pages.
Opposition, Costa Rica, translation from Foreign Associate Dated Nov. 20, 2013, 9 pages.
Opposition, Ecuador Patent Office, dated Nov. 18, 2008, 6 pages (English Translation).
Ortmann et al., "Janus kinases and signal transducers and activators of transcription: their roles in cytokine signaling, development and immunoregulation," Arthritis Res, 2000, 2(1): 16-32.
O'Shea et al., "Janus Kinase Inhibitors in Autoimmune Diseases," Ann Theum Dis., Apr. 2013, 72(Suppl 2):ii111-ii115.
Osteoporosis.aaos.org[online], "Osteoporosis," Feb. 2001, [retrieved on Dec. 15, 2018] retrieved from URL <https://orthoinfo.aaos.org/en/diseases--conditions/osteoporosis/>, 7 pages.
Ostojic et al., "Ruxolitinib: a new JAK1/2 inhibitor that offers promising options for treatment of myelofibrosis," Future Oncology, 2011, 7(9): 1035-1043.
Ostojic et al., "Ruxolitinib for the treatment of myelofibrosis," Drugs of Today, Nov. 2011, 47(11): 817-827.
Ousler et al., "Factors that influence the inter-blink interval (IBI) as measured by the ocular protection index (OPT)," Invest Ophthalmol Vis Sci 2001; 43: E-abstract 56 (Poster presentation) ARVO (2002) 2 pages, downloaded from http://abstracts.iov.s.org/cgi/content/abstract/43/12/56?maxtoshow on Aug. 14, 2009.
Padron et al., "Promising Results of a Phase 1/2 Clinical Trial of Ruxolitinib in Patients with Chronic Myelomonocytic Leukemia," Blood, 2017, 130:162.
Palmer et al., "Multiple roles of ephrins in morphogenesis, neuronal networking, and brain function," Genes & Dev., 2003, 17:1429-1450.
Panteli et al., "Serum interleukin (IL)-l, IL-2, sIL-2Ra, IL-6 and thrombopoietin levels in patients with chronic myeloproliferative diseases," British Journal of Haematology, 2005, 130: 709-715.
Pardanani et al., "CSF3R T618I is a highly prevalent and specific mutation in chronic neutrophilic leukemia," Leukemia, 2013, 27: 1870-1873.
Pardanani, "JAK2 inhibitor therapy in myeloproliferative disorders: rationale, preclinical studies and ongoing clinical trials JAK2 inhibitor therapy in MPD," Leukemia, Jan. 2008, 22: 23-30.
Parganas et al., "Jak2 is Essential for Signaling through a Variety of Cytokine Receptors," Cell, 1998, 93(3): 385-95.
Park et al., "Homogeneous Proximity Tyrosine Kinase Assays: Scintillation Proximity Assay versus Homogeneous Time-Resolved Fluorescence," Analytical Biochemistry, 1999, 269: 94-104.
Parks, "Tofacitinib and Other Kinase Inhibitors Offer New Approach to Treating Rheumatoid Arthritis," Rheumatologist, Jun. 2013, pp. 1-12 Available from: <http://www.the-rheumatologist.org/details/article/4871781/Tofacitinib_and_Other_Kinase_Inhibitors_Offer_New_Approach_to_Treating_Rheumatoi.html>, 12 pages.
Patani et al., "Bioisosterism: A Rational Approach in Drug Design," Chem. Rev., 1996, 96: 3147-3176.
Patel et al., "Formulation and Evaluation of Controlled Release Matrix Tablet of a Model Antibiotic Drug," Am. J. PharmTech. Res., 2012 2(2).
Patrick, "An Introduction to medicinal chemistry" Oxford University Press Inc., New York, 1995 (31 pages) (cited in Opposition from India dated Nov. 12, 2012.
Pearce et al., "An improved fluorophotometric method for tear turnover assessment," Optom Vis Sci, 2001, 78(l):30-36.
Pearce et al., "Spatial location studies on the chemical composition of human tear ferns," Ophthalmic Physiol Opt, 2000, 20(4):306-13.
Pedranzini et al., "Pyridone 6, A Pan-Janus-Activated Kinase Inhibitor, Induces Growth Inhibition of Multiple Myeloma Cells," Cancer Res., 2006, 66(19):9714-9721.
Peltola et al., "Pim-1 kinase expression predicts radiation response in squamocellular carcinoma of head and neck and is under the control of epidermal growth factor receptor," Neoplasia, 2009, 11:629-36.
Pensyl et al., "The repeatability of tear mucus ferning grading," Optom Vis Sci, 1998, 75(8):600-4.
Pernis et al., "JAK-STAT signaling in asthma," J Clin Invest, 2002, 109(10): 1279-83.
Peruvian Office Action in Peruvian Application No. 1345.15, dated Mar. 21, 2019, 18 pages.
Peters et al., "Functional Significance of Tie2 Signaling in the Adult Vasculature," 2004, © The Endocrine Society (21 pages).
Peturssion, "Protecting Groups in Carbohydrate Chemistry," J. Chem. Educ., 1997, 74(11):1297-1303.
Pflugfelder et al., "Evaluation of subjective assessments and objective diagnostic tests for diagnosing tear-film disorders known to cause ocular irritation," Cornea, 1998, 17(l):38-56.
Philippines Examination Report in Philippines Application No. 1-2013-501001, dated Mar. 23, 2017, 3 pages.
Pillonel "Evaluation of phenylaminopyrimidines as antifungal protein kinase inhibitors," Pest Management Science, Wiley & Sons, Jun. 2005, 61: 1069-1076.
Pirard et al., "Classification of Kinase Inhibitors Using BCUT Descriptors," J. Chem. Inf. Comput. Sci., 2000, 40: 1431-1440.
Pisella et al., "Conjunctival proinflammatory and proapoptotic effects of latanoprost, preserved timolol and unpreserved timolol: an ex vivo and in vitro study," Invest Ophthalmol Vis Sci, 2004, 45:1360-1368.
Pisella et al., "Flow cytometric analysis of conjunctival epithelium in ocular rosacea and keratoconjunctivitis sicca," Ophthalmology, 2000, 107:1841-1849.
Portnaya et. al., "Azomethine dyes. IV. Indoaniline dyes derived from heterocyclic N-substituted 1-hydroxy-2-naphthamide," Ts Vses Nauchn Issled Kinofotoinst, 1960, Issue 40, 106-8 (with English abstract 20 pages total).
Prchal et al., "Williams Hematology," New York: McGraw-Hill, 2010, 8th ed., Front Matter, 7 pages.

(56) References Cited

OTHER PUBLICATIONS

Press Release dated Sep. 13, 2018: "Incyte Announces Positive Data from Phase 2b Trial of Ruxolitinib Cream in Patients with Atopic Dermatitis" (2 pages).
Press Release dated Sep. 18, 2008: "Incyte's Topical JAK Inhibitor Demonstrates Positive Proof-of-Concept Results in Patients with Mild to Moderate Psoriasis" (4 pages).
Prezent et al., "Boron chelates as intermediates in the synthesis of new functionalized pyridines and pyrimidines from a, a-dioxoketene aminals," Proceedings of the International Conference on the Chemistry of Boron, vol. 11 (2003) (abstract only—1 page).
Product Monograph, "Jakavi," Prepared Jun. 15, 2012, Last revised, Sep. 28, 2018, 51 pages.
PubChem CID: 222786, "Cortisone," retrieved on Mar. 6, 2019, retrieved from URL<https://pubchem.ncbi.nih.gov/compound/cortisone#section=Chemical-and-Physical-Properties>, 39 pages.
PubChem CID: 5865, "Prednisone," retrieved on Mar. 6, 2019, retrieved from URL<https://pubchem.ncbi.nlm.nih.gov/compound/prednisone#section=Top>, 90 pages.
Punwani et al., Poster/presentation, "Initial Efficacy and Safety of Topical INCYB018424 Cream, a Selective Janus Kinase 1&2 (JAK 1&2) Inhibitor in Psoriasis" 17th Congress of the European Academy of Dermatology and Venereology, Paris, France, Sep. 17, 2008 (15 pages).
Punwani, Naresh, et al., "Efficacy and safety of topical INCB018424, a selective Janus kinase 1 & 2 (JAK1&2) inhibitor in psoriasis," Journal of the American Academy of Dermatology, vol. 60, No. 3, 2009.
Quesada et al., "One-pot conversion of activated alcohols into 1,1-dibromoalkenes and terminal alkynes using tandem oxidation processes with manganese dioxide," Tetrahedron, 2006, 62: 6673-6680.
Quintas-Cardama et al., "Preclinical characterization of the selective JAK1/2 inhibitor INCB018424: therapeutic implications for the treatment of myeloproliferative neoplasms," Blood First Edition Paper, prepublished online Feb. 3, 2010, American Society of Hematology; DOI 10.1182/blood-2009-04-214957, 115(15):3109-3117.
Ravin, "Preformulation," Remington's Pharmaceutical Sciences, 17th ed., Mack Publishing Company, Easton, Pa., 1985, Chapter 76, 1409-1423.
Raza et al., "Novel insights into the biology of myelodyplastic syndromes: excessive apoptosis and the role of cytokines," Int J Hematol, 1996, 63:265-278.
Raza et al., "The Myelodysplastic Syndromes in 1996: Complex Stem Cell Disorders Confounded by Dual Actions of Cytokines," Leuk Res, 1996, 20:881-890.
Raza et al., "Apoptosis in bone marrow biopsy samples involving stromal and hematopoietic cells in 50 patients with myelodysplastic syndromes," Blood, Jul. 1995, 86(1): 268-76.
Raza et al., "Phase 2 Study of lenalidomide in transfusion-dependent, low-risk, and intermediate-1 risk myelodysplastic syndromes with karyotypes other than deletion 5q," Blood, Jan. 2008, 111(1): 86-93.
Remington's Pharmaceutical Sciences, Mack Publishing Company, Easton, 1985, 17th ed., p. 1418.
Ren et al., "Compounds and Compositions as Protein Kinase Inhibitors," U.S. Appl. No. 60/578,491, filed Jun. 10, 2004 (56 pages).
Response and Amendment dated Aug. 25, 2009 to non-final Office Action for U.S. Appl. No. 12/137,892, 34 pages.
Response and Amendment in Reply to Action of Apr. 20, 2007 filed Jul. 17, 2007 for U.S. Appl. No. 11/313,394, 39 pages.
Response to Action of Aug. 22, 2007 dated Nov. 19, 2007, U.S. Appl. No. 11/115,702, 7 pages.
Response to Restriction Requirement dated May 29, 2007, U.S. Appl. No. 11/115,702, 8 pages.
Restriction Requirement dated Mar. 6, 2007 in connection with U.S. Appl. No. 11/115,702, 8 pages.
Reuters, "Jakafi (ruxolitinib) improved advanced pancreas cancer outcomes in mid-stage trial," Internet Citation, Aug. 21, 2013, pp. 1-2, XP002717211, Retrieved from Internet: URL: http://www.curetoday.com/index.cfm/fuseaction/news.showNewsArticle/id/13/news_id/3785 [retrieved on Nov. 29, 2013].
Riese et al., "Inhibition of JAK kinases in patients with rheumatoid arthritis: scientific rationale and clinical outcomes," Best Practice & Research Clinical Rheumatology, 2010, 513-526.
Roberts et al., "Trends in the Risks and Benefits to Patients With Cancer Participating in Phase 1 Clinical Trials," JAMA, 2004, 292(17):2130-2140.
Robin et al., "In vivo transillumination biomicroscopy and photography of meibomian gland dysfunction," Ophthalmology, 1985, 92:1423-6.
Robinson et al., "A Dual PIM 1/3 Kinase Inhibitor Demonstrates Efficacy in Murine Models of Lupus and Multiple Sclerosis," J. Immunol., 2012, 188:119.9.
Rodig et al., "Disruption of the Jaki gene demonstrates obligatory and nonredundant roles of the Jaks in cytokine-induced biologic responses," Cell, 1998, 93(3): 373-83.
Rolando et al., "Tear mucus crystallization in children with cystic fibrosis," Ophthalmologica, 1988, 197(4):202-6.
Rolando et al., "Tear mucus feming test in keratoconjunctivitis sicca," Holly FJ, Lamberts DW, MacKeen DL (eds.): The preocular tear film in health, disease, and contact lens wear,. 1st Intern Tear Film Symposium, Lubbock (Texas, USA), Dry Eye Institute, 1986, 203-210.
Rolando et al., "The effect of hyperosmolarity on tear mucus feming," Fortschr Ophthalmol, 1986, 83:644-646.
Rolando et al., "The Ocular Surface and Tear Film and Their Dysfunction in Dry Eye Disease," Survey of Ophthalmology, Mar. 2001, 45 (Supplement 2): S203-S210.
Rolando, "Tear mucus feming test in normal and keratoconjunctivitis sicca eyes," Chibret Int J Ophthalmol, 1984, 2(4):32-41.
Rollison et al., "Epidemiology of myelodysplastic syndromes and chronic myeloproliferative disorders in the United States, 2001-2004, using data from the NAACCR and SEER programs," Blood, Jul. 2008, 112(1): 45-52.
Roudebush et al., "Pharmacologic manipulation of a four day marine delayed type hyper sensitivity model," Agents Actions, 1993, 38(1-2):116-21.
Rousvoal et al. "Janus kinase 3 inhibition with CP-690,550 prevents allograft vasculopathy," Transpl Int., 2006, 19(12):1014-21.
Roy et al., "Formulation and design of sustained release matrix tablets of metformin hydrochloride: Influence of hypromellose and polyacrylate polymers," Int J Appl Basic Med Res., Jan. 2013, 3(1):55-63.
Saemann et al., "Suppression of early T-cell-receptor-triggered cellular activation by the Janus kinase 3 inhibitor MHI-P-154," Transplantation, 2003, 75(11): 1864-1872.
Saemann et al., "Prevention of CD40-triggered dendritic cell maturation and induction of T-cell hyporeactivity by targeting of Janus kinase 3," Am J Transplant, 2003, 3(11): 1341-9.
Saettone and Salminen, "Ocular inserts for topical delivery," Advanced Drug Delivery Reviews, 1995, 16:95-106.
Samanta et al., "Janus kinase 2: a critical target in chronic myelogenous leukemia," Cancer Res., Jul. 2006, 66(13):6468-72.
Santini et al., "Hepcidin Levels and Their Determinants in Different Types of Myelodysplastic Syndromes," PLoS One, 2011, 6(8): e23109, pp. 1-8.
Sawada et al., "Increased Lipophilicity and Subsequent Cell Partitioning Decrease Passive Transcellular Diffusion of Novel, Highly Lipophilic Antioxidants," The Journal of Pharmacology and Experimental Therapeutics, 1999, 288(3):1317-1326, p. 1321, compound 26.
Schatz, et al., "Targeting cap-dependent translation blocks converging survival signals by AKT and PIM kinases in lymphoma," J. Exp. Med., 2011, 208:1799-1807.
Schiffer, "Clinical issues in the management of patients with myelodysplasia," Hematology Am Soc Hematol Educ Program, 2006, 205-10.
Schiffer, "Myelodysplasia: the good, the fair and the ugly," Best Pract Res Clin Haematol, Mar. 2007, 20(1): 49-55.

(56) References Cited

OTHER PUBLICATIONS

Schindler et al., "Hormones and Signaling: Cytokines and STAT Signaling," Adv Pharmacol., 2000, 47:113-74.
Schmidt et al., "Rituximab in autoimmune bullous diseases: mixed responses and adverse effects," British Journal of Dermatology, 2007, 352-356.
Schrader et al., "Animal Models of Dry Eye," Developmental Ophthalmology, 2008, 41:298-312.
Schwemmers et al., "JAK2V617F-negative ET Patients do not display constitutively active JAK/STAT signaling," Exp. Hematol., Nov. 2007, 35(11): 1695-1703.
Scott et al., "Jaks, STATs, Cytokines, and Sepsis," Clin Diagn Lab Immunol, 2002, 9(6):1153-9.
Scott et al., "Prolonged responses in patients with MDS and CMML treated with azacitidine and etanercept," (British Journal of Haematology), Mar. 2010, 148(6): 944-947.
Search Report in TW Application No. 100117866, dated Dec. 2014, 1 page.
Search Report, dated Jul. 2, 2014, 6 pages.
Search Report, dated Jul. 3, 2014, 4 pages.
Search Report, dated Jul. 8, 2014, 4 pages.
Search Report, dated Jul. 8, 2014, 4 pages Not Duplicate.
Seefeld et al., "Discovery of 5-pyrrolopyridinyl-2-thiophenecarboxamides as potent AKT kinase," Bioorganic & Medicinal Chemistry Letters, 2009, 19(8):2244-2248.
Seela et al., "Synthesis of Pyrrolo[2,3-d]pyrimidine 2',3'-Dideoxyribenucleosides Related to 2',3'-Dideoxyadenosine and 2',3'-Dideoxgtuanosine and Inhibitory Activity of 5'-Triphosphates on HIV-1 Reverse Transcriptase," Helvetica Chimica Acta, 1991, 74(3), 554-64.
Seki, "STAT3 and MAPK in human lung cancer tissues and suppression of oncogenic growth by JAB and dominant negative STAT3," Int J Oncol., 2004, 24(4):931-4.
Seto et al., "Enhanced Th2 cell-mediated allergic inflammation in Tyk2-deficient mice," J Immunol, 2003, 170(2): 1077-83.
Shah et al., "Multiple BCR-ABL kinase domain mutations confer polyclonal resistance to the tyrosine kinase inhibitor imatinib (STI571) in chronic phase and blast crisis chronic myeloid leukemia," Cancer Cell, Aug. 2002, 2:117-125.
Sharma "Cell line-based platforms to evaluate the therapeutic efficacy of candidate anticancer agents" Nature Reviews Cancer Apr. 2010, vol. 10, 241-253.
Shen et al., "Inhibition of Pim-1 kinase ameliorates dextran sodium sulfate-induced colitis in mice," Dig. Dis. Sci., 2012, 57:1822-31.
Shi et al., "The pharmacokinetics, pharmacodynamics, and safety of orally dosed INCB018424 phosphate in healthy volunteers," Journal of Clinical Pharmacology, Dec. 2011, 51(12): 1644-1654.
Shimazaki et al., "Meibomian gland dysfunction in patients with Sjogren syndrome," Ophthalmology, 1998, 105(8): 1485-8.
Shinto et al., "Moloney murine leukemia virus infection accelerates lymphomagenesis in Eµ-bcl-2 transgenic mice," Oncogene, 1995, 11:1729-36.
Silverman et al., "Further analysis of trials with azacitidine in patients with myelodysplastic syndrome: studies 8421, 8921, and 9221 by the Cancer and Leukemia Group B," J Clin Oncol, Aug. 2006, 24(24): 3895-903.
Silverman et al., "Randomized controlled trial of azacitidine in patients with the myelodysplastic syndrome: a study of the cancer and leukemia group B," J Clin Oncol, May 2002, 20(10): 2429-40.
Simone, Oncology: Introduction, Cecil Textbook of Medicine, 20th Edition, 1996 vol. 1, pp. 1004-1010.
Sloand et al., "Factors affecting response and survival in patients with myelodysplasia treated with immunosuppressive therapy," J Clin Oncol, May 2008, 26(15): 2505-11.
Smith et al., "Basic pathogenic mechanisms operating in experimental model acute anterior uveitis," Immunology and Cell Biology, 1998, 76: 497-512.

Smolen et al., "Effect of interleukin-6 receptor inhibition with tocilizumab in patients with rheumatoid arthritis (OPTION study): a double-blind, placebo-controlled, randomized trial," Lancet, 2008, 371:987.
Sonbol et al., "Comprehensive review of JAK inhibitors in myeloproliferative neoplasms," Therapeutic Advances in Hematology, 2013, 4(1): 15-35.
Song et al. "JAK1 Activates STAT3 Activity in Non-Small-Cell Lung Cancer cells and IL-6 Neutralizing Antibodies can Suppress JAK1-STAT3 Signaling," Mol Cancer Ther., Mar. 2011, 10(3): 481-94.
Spoerl et al., "Activity of therapeutic JAK 1/2 blockade in graft-versus-host disease," Blood, 2014, 123(24): 3832-3842.
Srdan et al., "Safety and Efficacy of INCB018424, a JAK1 and JAK2 Inhibitor, in Myelfibrosis," The New England Journal of Medicine, Sep. 16, 2010, 363:1117-1127.
Sriram et al., "Induction of gpl30-related Cytokines and Activation of JAK2/STAT3 Pathway in Astrocytes Precedes Up-regulation of Glial Fibrillary Acidic Protein in the 1-Methyl-4-phenyl-l,2,3,6-tetrahydropyridine Model of Neurodegeneration," J. Biol. Chem., 2004, 279(19):19936-47.
Staerk et al., "JAK1 and Tyk2 activation by the homologous polycythemia vera JAK2 V617F mutation: cross-talk with IGF1 receptor," J Biol Chem., 2005, 280:41893-41899.
Stahl et al., "Topical Administration," Handbook of Pharmaceutical Salts, 2008, 22(43):110.
State Intellectual Property Office, PR China, Office Action, dated Sep. 3, 2010 Pat. Appl. No. 200680052750.7.
Steensma et al., "The JAK2 V617F activating tyrosine kinase mutation is an infrequent event in both "atypical" myeloproliferative disorders and mylodysplastic syndromes," Blood, Aug. 2005, 106(4):1207-9.
Stirewalt et al., "Predictors of relapse and overall survival in Philadelphia chromosome-positive acute lymphoblastic leukemia after transplantation," Biol Blood Marrow Transplant., Mar. 2003, 9(3):206-12.
STN Search conducted Aug. 30, 2010 (17 pages).
STN Search conducted Jun. 24, 2011 (24 pages).
STN Search conducted Nov. 5, 2010 (5 pages).
STN Search conducted Nov. 9, 2010 (43 pages).
STN Search, Nov. 12, 2009 (180 pages).
STN Search, Oct. 20, 2009 (601 pages).
STN Search, Sep. 20, 2009 (864 pages).
Strassmann et al., "Suramin Interferes with Interleukin-6 Receptor Binding in Vitro and Inhibits Colon-26-mediated Experimental Cancer Cachexia in Vivo," J. Clin. Invest., Nov. 1993, 92: 2152-2159.
Sullivan et al., "4th International Conference on the Lacrimal Gland, Tear Film & Ocular Surface and Dry Eye Syndromes, Nov. 20, 2004" (2 pages).
Sweet et al., "A Phase 1 Study of Ruxolitinib Plus Nilotinib in Chronic Phase CML Patients with Molecular Evidence of Disease," Blood, 2016, 125:1892.
Swords et al., "The Pim kinases: new targets for drug development," Curr. Drug Targets, 2011, 12(14):2059-66.
Symington et al., "The relationship of serum IL-6 levels to acute graft-versus-host disease and hepatorenal disease after human bone marrow transplantation," Transplantation, 1992, 54(3): 457-462 (Abstract only).
Taiwanese Office Action in Taiwanese Application No. 103101314, dated Dec. 28, 2017, 18 pages (English Translation).
Taiwanese Office Action in Taiwanese Application No. 103126987, dated Dec. 28, 2017, 9 pages (English Translation).
Takahashi et al., "Solvent-Free Reaction Using Phosphonium Salts: Chlorination of Hydroxyheteroaromatics and dehydration of Primary Amides," Heterocycles, 2006, 68:1973-1979.
Takano et al., "Inflammatory cells in brush cytology samples correlate with the severity of corneal lesions in atopic keratoconjunctivitis," Br J Ophthalmol, 2004, 88:1504-5.
Takemoto et al., "Proliferation of adult T cell leukemia/lymphoma cells is associated with the constitutive activation of JAK/STAT proteins," Proc Natl Acad Sci USA, 1997, 94(25):13897-902.

(56) References Cited

OTHER PUBLICATIONS

Tamura et al., "Involvement of Human Interleukin 6 in Experimental Cachexia Induced by a Human Uterine Cervical Carcinoma Xenograft," Clin. Cancer Res., Nov. 1995, 1:1353-1358.
Tan et al, "Racemization processes at a quaternary carbon center in the context of the asymmetric Michael reaction," Tetrahedron Lett., 2001, 42(30):5021-5023.
Tang et al., "Knowledge-based design of 7-azaindoles as selective B-Raf inhibitors," Bioorganic & Medicinal Chemistry Letters, 2008, 18(16):4610-4614.
Tasian et al., "Understanding the biology of CRLF2-overexpressing acute lymphoblastic leukemia," Critical Reviews in Oncogenesis, 2011, 16(1): 13-24.
Tefferi et al. "The Clinical Phenotype of Myelofibrosis Encompasses a Chronic Inflammatory State that is Favorably Altered by INCB018424, A Selective Inhibitor of JAK1/2" Poster #2804 at the American Society of Hematology Annual Meeting (ASH), Dec. 7, 2008, (18 pages).
Tefferi et al., "Serious adverse events during ruxolitinib treatment discontinuation in patients with myelofibrosis," Mayo Clinic Proceedings, Dec. 2011, 86(12): 1188-1191.
Tefferi, "Primary myelofibrosis: 2012 update on diagnosis, risk stratification, and management," American Journal of Hematology, Dec. 2011, 86(12): 1017-1026.
Textbook of Clinical Trials 264 (D. Machin et al., eds., 2nd ed., 2006).
Thompson et al., "Photochemical Preparation of a Pyridone Containing Tetracycle: A Jak Protein Kinase Inhibitor," Bioorganic & Medicinal Chemistry Letters, 2002, 12: 1219-1223.
Tiffany et al., Meniscectomy using the Tearscope-plus (ARVO abstract). Invest Ophthalmol Vis Sci, 2001,42: s37 (1 page).
Tiffany, "Refractive index of meibomian and other lipids," Curr Eye Res, 1986, 5:887-9.
Ting et al., "The Synthesis of substituted bipiperidine amide compounds as CCR3 antagonists," Bioorg. Med. Chem. Lett., 2005, 15(5): 1375-1378.
Toyonaga, "Blockade of constitutively activated Janus kinase/signal transducer and activator of transcription-3 pathway inhibits growth of human pancreatic cancer," Cancer Lett., 2003, 201(1):107-16.
Trikha et al., "Targeted anti-interleukin-6 monoclonal antibody therapy for cancer: a review of the rationale and clinical evidence," Clinical Cancer Research, 2003, 9: 4653-4665.
Tsubota et al., "Brush cytology for the evaluation of dry-eye," Nippon Ganka Gakkai Zasshi, 1990, 94:224-30 (English Abstract).
Tsubota et al., "Conjunctival brush cytology," Acta Cytol, 1990, 34(2):233-5.
Tsubota et al., "Detection by brush cytology of mast cells and eosinophils in allergic and vernal conjunctivitis," Cornea, 1991, 10(6):525-31.
UCSFhealth.org, "Liver Cancer," UCSF Medical Center, [retrieved on Nov. 9, 2018], retrieved from URL <https://www.ucsfhealth.org/conditions/liver_cancer/<, 3 pages.
Ueda et al., "1,2-Benzisoxazol-3-yl Diphenyl Phosphate: A New, Reactive Activating Agent for the Synthesis of Amides, Esters, and Peptides via Condensation," J. Org. Chem., 1985, 50:760-763.
UMM.edu, "Myeloproliferative disorders," May 12, 2017, University of Maryland Medical Center, [retrieved on Aug. 17, 2017] retrieved from URL <http://www.umm.edu/health/medical/altmed/condition/myeloproliferative-disorders>, 8 pages.
United States Office Action in U.S. Appl. No. 14/155,134, dated Jul. 27, 2015, 12 pages.
Vaillant et al., "Turbidity of pulpy fruit juice: A key factor for predicting cross-flow microfiltration performance," J Membrane Sci., 2008, 325:404-412.
van Best et al., "Measurement of basal tear turnover using a standardized protocol," Graefe's Arch Clin Exp Ophthalmol, 1995, 233:1-7.
van Bijsterveld, "Diagnostic tests in the sicca syndrome," Arch Ophthalmol, 1969, 82:10-14.

van Rhee et al., "Anti-Interleukin-6 Monoclonal man's Disease," J. Clin. Oncol., 2010, 28(23):3701-3708.
Vanhoutte, "Selective JAK1 Inhibition in the Treatment of Rheumatoid Arthritis: Proof of Concept with GLPG0634," Arthritis Rheum, 2012, 64.10: S1051-1.
Vannucchi et al., "Inhibitors of PI3K/Akt and/or mTOR Inhibit the Growth of Cells of Myeloproliferative Neoplasms and Synergize with JAK2 Inhibitor and Interferon," Blood, 2011, 118(21): 1638-1639, XP008150742ASH Annual Meeting Abstract 3835 American Society of Hematology.
Vannucchi et al., "RAD001, An Inhibitor of mTOR, Shows Clinical Activity in a Phase I/II Study in Patients with Primary Myelofibrosis (PMF) and Post Polycythemia Vera/Essential Thrombocythemia Myelofibrosis (PPV/PET MF)," Blood, ASH Annual Meeting Abstracts 307, 2009, 114(22), 2 pages.
Vannucchi et al., "The mTOR Inhibitor, RAD001, Inhibits the Growth of Cells From Patients with Myeloproliferative Neoplasms," Blood: ASH Annual Meeting Abstracts, 51st Annual Meeting of the American Society of Hematology, 2009, 114(22), 2 pages.
Vardiman et al., "The 2008 revision of the World Health Organization (WHO) Classification of myeloid neoplasms and acute leukemia: rationale and important changes," Blood, 2009, 114:937-951.
Vardiman et al., "The World Health Organization (WHO) classification of the myeloid neoplasms," Blood, 2002, 100:2292-2302.
Vardiman et al., "Atypical chronic myeloid leukaemia, BCR-ABL1 negative," in: Swerdlow, et al., WHO Classification of Tumors of Haematopoietic and Lymphoid Tissues (ed 4th), Lyon: IARC Press; 2008:80-81.
Vasilevsky et al., "Ethyl Vinyl Ether—an Agent for Protection of the Pyrazole NH-Fragment. A Convenient Method for the Preparation of N-Unsubstituted 6Alkynylpyrazoles," Heterocycles, 2003, 60(4):879-886.
Venkatesh et al., "Role of the Development Scientist in Compound Lead Selection and Optimization," J. Pharm. Sci., 2000, 89:145-54.
Venugopal et al., "Special clinical concerns/problems in the management of MDS and secondary acute myeloid leukemias," Cancer Treat Res, 2001, 108: 257-65.
Verma et al., "Jak family of kinases in cancer," Cancer and Metastasis Reviews, 2003, 22(4): 423-434, DOI: 10.1023/A:1023805715476.
Verstovsek et al., "Efficacy, safety and survival with ruxolitinib in patients with myelofibrosis: results of a median 2-year follow-up of COMFORT-I," Haematologica, 2013, 98(12):1865-1871.
Verstovsek, "Therapeutic Potential of JAK2 Inhibitors," Hematology Am Soc Hematol Educ Program, 2009:636-42.
Verstovsek, et al., Blood (ASH Annual Meeting Abstracts) 2007 110: Abstract 558.
Verstovsek, et al., Blood (ASH Annual Meeting Abstracts) 2009 114: Abstract 311.
Verstovsek, et al., Blood (ASH Annual Meeting Abstracts) 2010 116: Abstract 313.
Verstovsek, S. et al. "The JAK Inhibitor INCB018424 Demonstrates Durable and Marked Clinical Responses in Primary Myelofibrosis (PMF) and Post-Polycythemia/Essential Thrombocythemia Myelofibrosis (Post-PV/ET-MF)" Poster #1762 at the American Society of Hematology Annual Meeting (ASH), Dec. 6, 2008 (19 pages).
Verstovsek, S. et al. "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET MF)" Abstract #0444, presented Saturday, Jun. 14, 2008 at the European Hematology Association, 13th Congress, June 12-15, Copenhagen, Denmark (2 pages).
Verstovsek, S. et al. INCB18424, an Oral, Selective JAK2 Inhibitor, Shows Significant Clinical Activity in a Phase I/II Study in Patient with Primary Myelofibrosis (PMF) and Post Polycythemia Vera/Essential Thrombocythemia Myelofibrosis (Post-PV/ET MF), presentation at the American Society of Hematology 49th Annual Meeting and Exposition, Dec. 10, 2007 (16 pages).

(56) References Cited

OTHER PUBLICATIONS

Verstovsek, Srdan et al., "Characterization of Jaks V617F Allele Burden in Advanced Myelofibrosis (MF) Patients: No Change in V617F:WT JAK2 Ratio in Patients with High Allele Burdens despite Profound Clinical Improvement Following Treatment with the JAKL Inhibitor, INCB018424, "50th ASH Annual Meeting and Exposition, Abstract No. 2802 (2008).
Vietnamese Office Action in Vietnamese Application No. 48930/SHTT-SC, dated Dec. 28, 2018, 2 pages.
Vitali et al. "The European Community Study Group on diagnostic criteria for Sjogren's syndrome. Sensitivity and specificity of tests for ocular and oral involvement in Sjogren's syndrome," Ann Rheum Dis, 1994, 53(10): 637-47.
Wagh et al., "Polymers used in ocular dosage form and drug delivery systems," Asian J. Pharm., Jan. 2008, 12-17.
Wang and Deisboeck, "Mathematical modeling in cancer drug discovery," Drug Discovery Today, 2014, 145-150.
Wang et al., "Inhibition of Pim1 kinase prevents peanut allergy by enhancing Runx3 expression and suppressing T(H)2 and T(H)17 T-cell differentiation," J. All. Clin. Immunol., 2012, 130:932-44.
WebMD. "Diabetes Health Center," Available at: < http://diabetes.webmd.com/guide/diabetestreatment_care >, 3 pages, retrieved from the Internet May 28, 2013.
Webster's New World Medical Dictionary, Sjogren's syndrome, 2003, Wiley Publishing, printed from http://www.credoreference.com/entry/webstermed/sjogren_s_syndrome, 2 pages.
Weiss et al., "Evaluation of a Series of Naphthamides as Potent, Orally Active Vascular Endothelial Growth Factor Receptor-2 Tyrosine Kinase Inhibitors," J. Med Chem., 2008, 51:1668-1680.
Welch et al., "An approach to a more standardized method of evaluating tear film break-up time," Invest Ophthalmol Vis Sci, 2003, 2485/B324 (abstract only—2 pages).
White et al., "Human basic tear fluid osmolality. I. Importance of sample collection strategy," Acta Ophthalmol (Copenh), Aug. 1993, 71(4):524-9.
Wilks, "The JAK kinases: Not just another kinase drug discovery target," Seminars in Cell & Developmental Biology, 2008, 319-328.
Williams and Ibrahim, "Carbodiimide Chemistry: Recent Advances," Chem. Rev., 1981, 81:589-636.
Williams et al., "Dissecting Specificity in the Janus Kinases: The Structures of JAK-Specific Inhibitors Complexed to the JAK1 and JAK2 Protein Tyrosine Kinase Domains," Journal of Molecular Biology, 2009, 219-232.
Williams, et al. "Initial Efficacy of INCB018424, a selective Janus Kinase1& 2 (JAK1&2) Inhibitor in Rheumatoid Arthritis (RA)," European League Against Rheumatism (EULAR) meeting presentation and abstract (Jun. 11-14, 2008, Paris, France). Annals Rheum Dis 67SII:62, 2008.
Winfield, Pharmaceutical Practice, Ophthalmic Products-pH adjustment, Churchill Livingstone, 2004, 264-271.
Winyard, P.G. and Willoughby, D.A., "Inflammation Protocols," Humana Press, Methods in Molecular Biology:, 2003, vol. 225, 359 pages.
Wolff et al., "Burger's Medicinal Chemistry and Drug Discovery," 5th Ed. Part I, 1995, 975-977.
Wu et al., One-Pot Two-Step Microwave-Assisted Reaction in Construction 4,5-Disubstituted Pyrazolopyrimidines Organic Letters, 2003, 5(20): 3587-3590.
Wuts and Greene, Protective Groups in Organic Synthesis, 4th ed., John Wiley & Sons: New Jersey, (2007) **Too Voluminous to Provide.
www.leukaemia.org [online], "Myeloproliferative neoplasms (MPN)," 2016, [retrieved on Dec. 5, 2016], Retrieved from the Internet: URL<http://www.leukaemia.org.au/blood-cancers/myeloproliferative-neoplasms-mpn>, 3 pages.

Xiong, "Inhibition of JAK1, 2/STAT3 Signaling Induces Apoptosis, Cell Cycle Arrest, and Reduces Tumor Cell Invasion in Colorectal Cancer Cells," Neoplasia, Mar. 2008, 10(3): 287-297.
Yacoub et al., "Ruxolitinib improves symptoms and quality of life in patient with systemic mastocytosis," Biomarker Research, 2016, 4:2.
Yamamura et al., "Circulating interleukin-6 levels are elevated in adult T-cell leukaemia/lymphoma patients and correlate with adverse clinical features and survival," Br. J. Haematol., 1998, 100: 129-134.
Yamaoka et al., "Janus kinase (JAK) inhibitors in rheumatoid arthritis," Current Rheumatology Reviews, Nov. 2011, 7(4): 306-312.
Yan et al., "Clinical and therapeutic relevance of PIM1 kinase in gastric cancer," Gastric Cancer, 2012, 15:188-197.
Yang et al., "Proviral integration site 2 is required for interleukin-6 expression induced by interleukin-1, tumour necrosis factor-$\alpha$ and lipopolysaccharide," Immunol., 2010, 131:174-182.
Yang et al., "Constitutive NF-KB activation confers interleukin 6 (IL6) independence and resistance to dexamethasone and Janus kinase inhibitor INCB018424 in murine plasmacytoma cells," Journal of Biological Chemistry, Aug. 2011, 286(32):27988-27997.
Yao et al. "Glucocorticoid-Induced Bone Loss in Mice Can Be Reversed by the Actions of Parathyroid Hormone and Risedronate on Different Pathways for Bone Formation and Mineralization," Arthritis and Rheumatism, 2008, 58(11):3485-3497.
Yao, et al., "Glucocorticoid Excess in Mice Results in Early Activation of Osteoclastogenesis and Adipogenesis and Prolonged Suppression of Osteogenesis," Arthritis and Rheumatism, 2008, 58(6), 1674-1686.
Yokoi et al., "A newly developed video-meibography system featuring a newly designed probe," Jpn J Ophthalmol, 2007, 51: 53-6.
Yokoi et al., "Assessment of meibomian gland function in dry eye using meibometry," Arch Ophthalmol, 1999, 117:723-9.
Yokoi et al., "Correlation of tear lipid layer interference patterns with the diagnosis and severity of dry eye," Am J Ophthalmol, 1996, 122:818-824.
Yokoi et al., "Non-invasive methods of assessing the tear film," Exp Eye Res, 2004, 78:399-407.
Younes et al., "Phase I Study of a Novel Oral Janus Kinase 2 Inhibitor, SB1518, in Patients With Relapsed Lymphoma: Evidence of Clinical and Biologic Activity in Multiple Lymphoma Subtypes," J. Clin. Oncol., 2012, 30(33):4161-4167.
Yu et al., "Role of Janus Kinase/Signal Transducers and Activators of Transcription in the Pathogenesis of Pancreatitis and Pancreatic Cancer," Gut and Liver, Oct. 2012, 6(4):417-422.
Yu et al., "Constitutive activation of the Janus kinase-STAT pathway in T lymphoma overexpressing the Lck protein tyrosine kinase," J Immunol., 1997, 159(11):5206-5210.
Zaidi et al., "Dermatology in Clinical Practice," Springer, 2010, 157 pages.
Zheng et al., "Discovery of INCB108201PF-4178903, a potent, selective, and orally bioavailable dual CCR2 and CCR5 antagonist," Bioorganic & Medicinal Chemistry Letters, 2011, 21: 1442-45.
Zippo, et al., "PIM 1-dependent phosphorylation of histone H3 at serine 10 is required for MYC-dependent transcriptional activation and oncogenic transformation," Nature Cell Biol., 2007, 9:932-44.
Zoppellaro et al., "A Multifunctional High-Spin Biradical Pyrazolylbipyridine-bisnitronylnitroxide," Org. Lett., 2004, 6(26):4929-4932.
Zou et al., "Signaling Pathways Activated by Oncogenic Forms of Abl Tyrosine Kinase," Journal of Biological Chemistry, 1999, 274(26):18141-18144.

\* cited by examiner

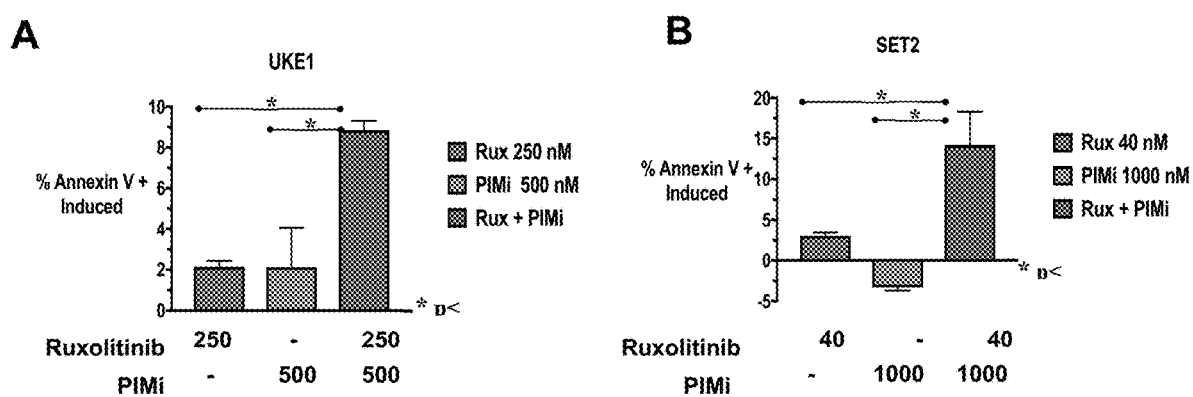
FIG. 2(A-B)

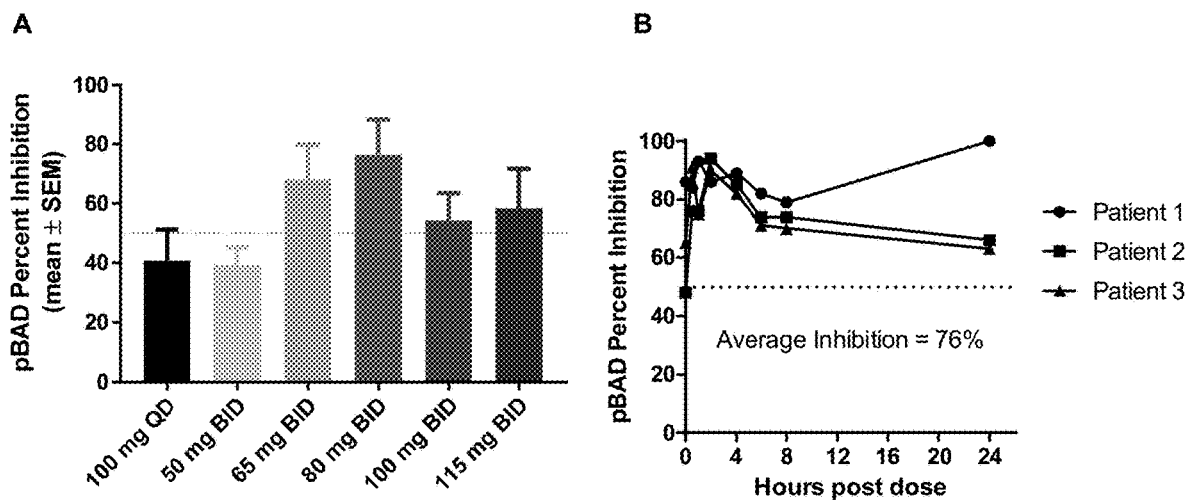
FIG. 5(A-B)

LOW DOSE COMBINATION THERAPY FOR TREATMENT OF MYELOPROLIFERATIVE NEOPLASMS

CROSS-REFERENCE TO RELATED APPLICATIONS

This application is a continuation of U.S. patent application Ser. No. 16/213,550, filed Dec. 7, 2018, which claims the benefit of U.S. Provisional Patent Application No. 62/596,553, filed Dec. 8, 2017, each of which is incorporated by reference in its entirety.

TECHNICAL FIELD

The present application relates to treatment of myeloproliferative neoplasms using the JAK1/JAK2 inhibitor, ruxolitinib, in combination with a low dose of a Pim inhibitor, N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, wherein the combination is unexpectedly synergistic at a very low dose of the Pim inhibitor.

BACKGROUND

The discovery of the activating V617F mutation in Janus kinase 2 (JAK2) in the majority of patients with the classic Philadelphia chromosome-negative (Ph−) myeloproliferative neoplasms (MPN) provided a strong impetus for the development of pharmacologic inhibitors of JAK2, culminating in the regulatory approval of the JAK1/2 inhibitor, ruxolitinib, for patients with myelofibrosis (MF) in 2011 and hydroxyurea (HU)-resistant/intolerant polycythemia vera (PV) in 2014. The activity of ruxolitinib in patients with MF without regard to JAK2 mutation status was an important observation that was vindicated by the finding of universal activation of the JAK-signal transducer and activator of transcription (STAT) pathway in MPNs.

However, because JAK2 signaling is not suppressed long term and molecular remission is not observed in patients treated with JAK2 inhibitors, there is a need for new therapies to improve patient outcome. This application is directed to this need and others.

SUMMARY

The present application provides, inter alia, methods of treating a myeloproliferative neoplasm in a patient in need thereof, comprising administering to said patient N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, and ruxolitinib, or a pharmaceutically acceptable salt thereof.

The present application further provides methods of treating a myeloproliferative neoplasm in a patient in need thereof, comprising administering to said patient a dose from about 5 mg/day to about 100 mg/day N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, and a therapeutically effective amount of ruxolitinib, or a pharmaceutically acceptable salt thereof.

The present application also provides methods of treating a myeloproliferative neoplasm in a patient in need thereof, comprising administering to said patient a dose from about 5 mg/day to about 100 mg/day N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, and a dose of from about 10 mg/day to about 50 mg/day of ruxolitinib, or a pharmaceutically acceptable salt thereof.

The present application further provides the use of the compounds at the doses recited herein for use in the manufacture of medicaments for use in treating a myeloproliferative neoplasm.

The present application also provides the compounds at the doses recited herein for use in treating a myeloproliferative neoplasm.

The details of one or more embodiments are set forth in the description below. Other features, objects, and advantages will be apparent from the description and from the claims.

DESCRIPTION OF THE FIGURES

FIGS. 2 (A and B) depict % annexin V+ in UKE1 and SET2 cells treated with vehicle (DMSO), ruxolitinib, Compound 1 (PIMi), or the two drugs together.

FIG. 5(A) depicts % pBAD inhibition in plasma samples from patients at 24 hours post dose of Compound 1.

FIG. 5(B) depicts % pBAD inhibition in plasma samples from patients at on cycle 1, day 8 for 80 mg BID of Compound 1.

DETAILED DESCRIPTION

Figure 1B:
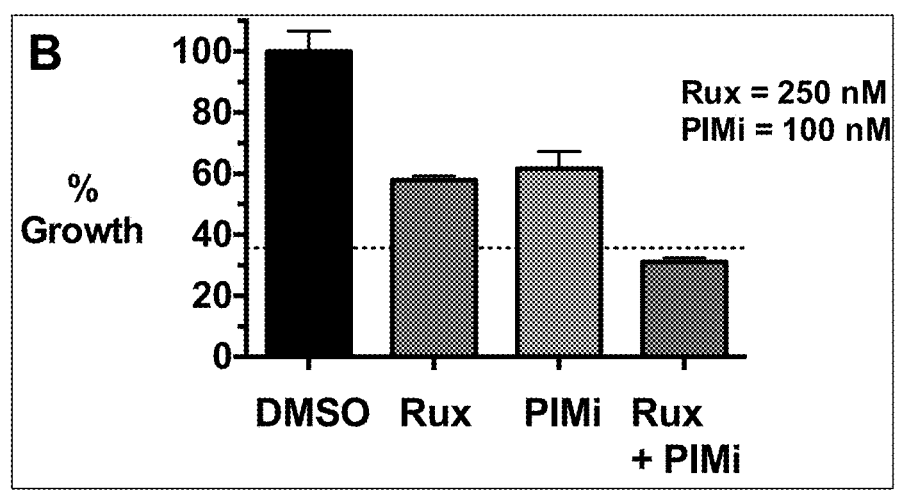
FIGS. 1(A, B, and C) depict the % growth in BaF3/EpoR/JAK2-V617F, UKE1, and SET2 cells, respectively, for untreated cells or cells treated with ruxolitinib (Rux) or Compound 1 (PIMi), and these two together (Rux+PIMi).

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

As used herein, the term "about" means "approximately" (e.g., plus or minus approximately 10% of the indicated value).

The present invention relates to the use of a JAK1/JAK2 inhibitor, ruxolitinib, in combination with a PIM inhibitor for treatment of a myeloproliferative neoplasm. It has been unexpectedly found that very low doses of the PIM inhibitor synergize with ruxolitinib at levels below $IC_{50}$ and much lower for the PIM inhibitor.

Ruxolitinib, (3R)-3-cyclopentyl-3-[4-(7H-pyrrolo[2,3-d]pyrimidin-4-yl)-1H-pyrazol-1-yl]propanenitrile, is an inhibitor of JAK1 and JAK2. The $IC_{50}$ of ruxolitinib was measured by Assay A infra at 1 mM ATP and found to be less than 10 nM at JAK1 and JAK2.

Ruxolitinib can be made by the procedure described in U.S. Pat. No. 7,598,257 (Example 67), filed Dec. 12, 2006, which is incorporated herein by reference in its entirety. Ruxolitinib phosphate can be prepared as described in US 2008/0312259, which is incorporated herein by reference in its entirety.

N-{(7R)-4-[(3R,4R,5S)-3-Amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide (Compound 1 below) is an inhibitor of Pim1, Pim2, and Pim3. Compound 1 can prepared as described in U.S. Pat. No. 9,200,004 or US 2017/0121310, each of which is incorporated herein by reference in its entirety. The $IC_{50}$ of Compound 1 was measured by the procedure in Assay B infra and found to be ≤100 nM at Pim1, Pim2, and Pim3. The phosphoric acid salt, dihydrochlorlic acid salt, hydrochloric acid salt, maleic acid salt, adipic acid salt, hydrobromic acid salt, (R)-(−)-mandelic acid salt, salicylic acid salt, benzoic acid salt, benzenesulfonic acid salt, L-pyroglutamic acid salt, methanesulfonic acid salt, (1S)-(+)-10-camphorsulfonic acid salt, fumaric acid salt, sulfuric acid salt, L-tartaric acid salt, and D-tartaric acid salt of Compound 1 can be prepared as described in US 2017/0121310, which is incorporated herein by reference in its entirety. The $IC_{50}$ of the dihydrochloric acid and phosphoric acid salts of Compound 1 was measured by the procedure in Assay B infra and found to be <35 nM at Pim1, Pim2, and Pim3.

Compound 1

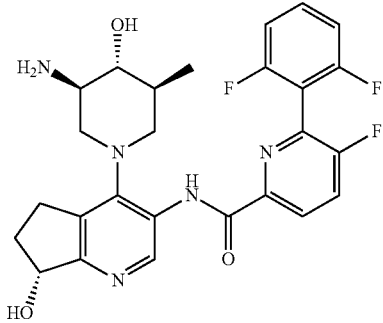

Accordingly, the present application provides a method of treating a myeloproliferative neoplasm in a patient in need thereof, comprising administering to said patient N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, and ruxolitinib, or a pharmaceutically acceptable salt thereof.

The present application further provides a method of treating a myeloproliferative neoplasm in a patient in need thereof, comprising administering to said patient a dose from about 2 mg/day to about 160 mg/day N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, and a therapeutically effective amount of ruxolitinib, or a pharmaceutically acceptable salt thereof.

The present application further provides a method of treating a myeloproliferative neoplasm in a patient in need thereof, comprising administering to said patient a dose from about 2 mg/day to about 100 mg/day N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, and a therapeutically effective amount of ruxolitinib, or a pharmaceutically acceptable salt thereof.

The present application further provides a method of treating a myeloproliferative neoplasm in a patient in need thereof, comprising administering to said patient a dose from about 5 mg/day to about 100 mg/day N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, and a therapeutically effective amount of ruxolitinib, or a pharmaceutically acceptable salt thereof.

The present application also provides a method of treating a myeloproliferative neoplasm in a patient in need thereof, comprising administering to said patient a dose from about 5 mg/day to about 100 mg/day N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, and a dose of from about 10 mg/day to about 50 mg/day of ruxolitinib, or a pharmaceutically acceptable salt thereof.

In some embodiments, the dose of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, is from about 5 mg/day to about 100 mg/day.

In some embodiments, the dose of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, is from about 8 mg/day to about 80 mg/day.

In some embodiments, the dose of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, is from about 8 mg/day to about 70 mg/day.

In some embodiments, the dose of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, is from about 8 mg to about 60 mg/day.

In some embodiments, the dose of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, is from about 8 mg/day to about 50 mg/day.

In some embodiments, the dose of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, is from about 8 mg/day to about 40 mg/day.

In some embodiments, the dose of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, is from about 8 mg/day to about 30 mg/day.

In some embodiments, the dose of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, is from about 8 mg/day to about 20 mg/day.

In some embodiments, the dose of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, is from about 2 mg BID to about 50 mg BID.

In some embodiments, the dose of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, is from about 4 mg BID to about 40 mg BID.

In some embodiments, the dose of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, is from about 4 mg BID to about 35 mg BID.

In some embodiments, the dose of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, is from about 4 mg to about 30 mg BID.

In some embodiments, the dose of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, is from about 4 mg BID to about 25 mg BID.

In some embodiments, the dose of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, is from about 4 mg BID to about 20 mg BID.

In some embodiments, the dose of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, is from about 4 mg BID to about 15 mg BID.

In some embodiments, the dose of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, is from about 4 mg BID to about 10 mg BID.

In some embodiments, the dose of ruxolitinib, or a pharmaceutically acceptable salt thereof, is about 10 mg/day to about 30 mg/day.

In some embodiments, the dose of ruxolitinib, or a pharmaceutically acceptable salt thereof, is about 10 mg/day to about 50 mg/day.

In some embodiments, the dose of ruxolitinib, or a pharmaceutically acceptable salt thereof, is about 10 mg/day to about 30 mg/day.

In some embodiments, the dose of ruxolitinib, or a pharmaceutically acceptable salt thereof, is about 10 mg/day.

In some embodiments, the dose of ruxolitinib, or a pharmaceutically acceptable salt thereof, is about 20 mg/day.

In some embodiments, the dose of ruxolitinib, or a pharmaceutically acceptable salt thereof, is about 30 mg/day.

In some embodiments, the dose of ruxolitinib, or a pharmaceutically acceptable salt thereof, is about 5 mg BID to about 25 mg BID.

In some embodiments, the dose of ruxolitinib, or a pharmaceutically acceptable salt thereof, is about 5 mg BID to about 15 mg BID.

In some embodiments, the dose of ruxolitinib, or a pharmaceutically acceptable salt thereof, is about 5 mg BID.

In some embodiments, the dose of ruxolitinib, or a pharmaceutically acceptable salt thereof, is about 10 mg BID.

In some embodiments, the dose of ruxolitinib, or a pharmaceutically acceptable salt thereof, is about 15 mg BID.

In some embodiments, ruxolitinib, or a pharmaceutically acceptable salt thereof, is ruxolitinib phosphate.

In some embodiments, the N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, is selected from the phosphoric acid salt, dihydrochlorlic acid salt, hydrochloric acid salt, maleic acid salt, adipic acid salt, hydrobromic acid salt, (R)-(−)-mandelic acid salt, salicylic acid salt, benzoic acid salt, benzenesulfonic acid salt, L-pyroglutamic acid salt, methanesulfonic acid salt, (1S)-(+)-10-camphorsulfonic acid salt, fumaric acid salt, sulfuric acid salt, L-tartaric acid salt, and D-tartaric acid salt of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide.

In some embodiments, the N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, is the phosphoric acid salt of N-{(7R)-4-[(3R,4R,5S)-3-Amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide.

In some embodiments, the myeloproliferative neoplasm is selected from polycythemia vera (PV), essential thrombocythemia (ET), primary myelofibrosis, chronic myelogenous leukemia (CML), chronic myelomonocytic leukemia (CMML), hypereosinophilic syndrome (HES), systemic mast cell disease (SMCD), chronic neutrophilic leukemia (CNL), and chronic eosinophilic leukemia.

In some embodiments, the myeloproliferative neoplasm is selected from polycythemia vera (PV).

In some embodiments, the myeloproliferative neoplasm is selected from essential thrombocythemia (ET).

In some embodiments, the myeloproliferative neoplasm is selected from primary myelofibrosis.

In some embodiments, the myeloproliferative neoplasm is myelofibrosis.

In some embodiments, the ruxolitinib, or pharmaceutically acceptable salt thereof, and the N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, are administered orally.

The preceding embodiments are intended to be combined in any suitable combination as if the embodiments are multiply dependent claims (e.g., the embodiments related to the individual doses for ruxolitinib, the embodiments related to the individual doses for the PIM inhibitor (Compound 1), the embodiments related to the salt forms, the embodiments related to the individual types of myeloproliferative neoplasms, and the embodiments related to oral administration can be combined in any combination). The combinations are not separately listed herein merely for the sake of brevity.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19, and in Stahl et al., *Handbook of Pharmaceutical Salts: Properties, Selection, and Use*, (Wiley, 2002). In some embodiments, the compounds described herein include the N-oxide forms.

The dosages described herein are on a free base basis.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

The term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease. In one embodiment, treating or treatment includes preventing or reducing the risk of developing the disease; e.g., preventing or reducing the risk of developing a disease, condition or disorder in an individual who may be predisposed to the disease, condition or disorder but does not yet experience or display the pathology or symptomatology of the disease. The term "BID" means two times a day.

Additional Combinations

Cell growth and survival can be impacted by multiple signaling pathways. Thus, it is useful to combine different kinase inhibitors, exhibiting different preferences in the kinases which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

Accordingly, the methods can further comprise the administration of one or more other kinase inhibitors. For example, the compounds of the invention can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSF1R, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Additionally, the Pim inhibitors of the invention can be combined with inhibitors of kinases associated with the PIK3/Akt/mTOR signaling pathway, such as PI3K, Akt (including Akt1, Akt2 and Akt3) and mTOR kinases.

The methods can further be used in combination with other methods of treatment, for example by chemotherapy, irradiation, or surgery. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

The methods can further be used in combination with one or more anti-inflammatory agents, steroids, immunosuppressants, or therapeutic anti-bodies.

When more than one pharmaceutical agent is administered to a patient, they can be administered simultaneously, sequentially, or in combination (e.g., for more than two agents).

Compositions

The compounds can be administered in the form of pharmaceutical compositions. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

The pharmaceutical compositions can contain, as the active ingredient, the compounds, or a pharmaceutically acceptable salt thereof, in combination with one or more pharmaceutically acceptable carriers (excipients). In some embodiments, the composition is suitable for topical administration. In making the compositions, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; and sweetening agents and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline® (petroleum jelly) and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose and the like.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

Kits

The present application also includes pharmaceutical kits useful, which include one or more containers containing a pharmaceutical composition comprising a therapeutically effective amount of the compound, or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be Pim-kinase inhibitors according to at least one assay described herein.

EXAMPLES

Example A: In Vitro JAK Kinase Assay

Compounds herein were tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) were expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). $IC_{50}$s of compounds were measured for each kinase in the 40 μL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM $IC_{50}$ measurements, ATP concentration in the reactions was 1 mM. Reactions were carried out at room temperature for 1 hour and then stopped with 20 μL 45 mM EDTA, 300 nM SA-APC, 6 nM Eu-Py20 in assay buffer (Perkin Elmer, Boston, Mass.). Binding to the Europium labeled antibody took place for 40 minutes and HTRF signal was measured on a PHERA star plate reader (BMG, Cary, N.C.). The data for the JAK1 and/or JAK2 inhibitors were obtained by testing the compounds in the Example A assay at 1 mM ATP.

Example B. Pim Enzyme Assays

Pim-1 and Pim-3 kinase assays—20 μL reactions were run in white 384 well polystyrene plates dotted with 0.8 μL compound/DMSO in the assay buffer (50 mM Tris, pH 7.5, 0.01% Tween-20, 5 mM $MgCl_2$, 0.01% BSA, 5 mM DTT), containing 0.05 μM Biotin-labeled BAD peptide substrate (AnaSpec 62269), 1 mM ATP, and 2.5 pM (Pim-1, Invitrogen PV3503) or 1.25 pM (Pim-3, Millipore 14-738) enzyme for 1 h at 25° C. Reactions were stopped by addition of 10 μL STOP Buffer (150 mM Tris, pH=7.5, 150 mM NaCl, 75 mM EDTA, 0.01% Tween-20, 0.3% BSA) supplemented with Phospho-Bad (Ser112) Antibody (Cell Signaling 9291) diluted 666-fold, and Streptavidin donor beads (PerkinElmer 6760002) along with Protein-A acceptor beads (PerkinElmer 6760137) at 15 μg/mL each. Supplementation of the STOP buffer with beads and stopping the reactions were done under reduced light. Prior to the stopping reactions STOP buffer with beads was pre-incubated for 1 h in the dark at room temperature. After stopping the reactions, plates were incubated for 1 h in the dark at room temperature before reading on a PHERAstar FS plate reader (BMG Labtech) under reduced light.

Pim-2 kinase assay—20 μL reactions were run in white 384 well polystyrene plates dotted with 0.8 μL compound/DMSO in the assay buffer (50 mM Tris, pH 7.5, 0.01% Tween-20, 5 mM $MgCl_2$, 0.01% BSA, 5 mM DTT), containing 0.05 μM Fluorescein-labeled CREBtide peptide substrate (Invitrogen PV3508), 1 mM ATP, and 1 nM enzyme (Invitrogen PV3649) for 2 h at 25° C. Reactions were stopped by addition of 10 μL TR-FRET Dilution Buffer (Invitrogen PV3574) with 30 mM EDTA and 1.5 nM LanthaScreen Tb-CREB pSer133 antibody (Invitrogen PV3566). After 30 min. incubation at room temperature, plates were read on a PHERAstar FS plate reader (BMG Labtech).

Compounds of the invention having an $IC_{50}$ of 2 μM or less when tested for PIM kinase activity under the assay conditions disclosed above are considered active.

Although the above in vitro assays are conducted at 1 mM ATP compounds can also be evaluated for potency and in vitro activity against PIM targets utilizing $K_m$ conditions, where the concentration of ATP is set to the $K_m$ value and the assay is more sensitive to PIM inhibition activity.

Example C. Pim Cellular Assays

One or more compounds of the invention were tested for inhibitory activity of PIM according to at least one of the following cellular assays. Compounds of the invention having an $IC_{50}$ of 10 μM or less when tested for PIM kinase activity under the cellular assay conditions disclosed below would be and were considered active.

Pim Cell Proliferation Assays

KG-1A cells are purchased from ATCC (Manassas, Va.) and KMS.12.BM cells are purchased from NIBIO, JCRB cell bank (Tokyo, Japan) and maintained in the culture mediums recommended, RPMI, 10% FBS (Roswell Park Memorial Institute 1640 Medium supplemented with 10% fetal bovine serum) and IMDM 20% FBS (Iscove's Modified Dulbecco's Medium (MDM) with 20% fetal bovine strum) (Mediatech, Manassas, Va.) respectively. To measure the anti-proliferation activity of test compounds, both cell lines are plated with the culture medium ($2 \times 10^3$ cells/well/in 200 μL) into 96-well polystyrene ultralow binding (Costar®) in the presence or absence of a concentration range of test compounds. After 4 days, [$^3$H]-thymidine, 1 μCi/10 μL/well (PerkinElmer, Boston, Mass.) in culture medium is then added to the cell culture for an additional 16 h before the incorporated radioactivity is separated by filtration with a Packard Microplate Harvester with water through a 0.3% polyethylenimine pre-wetted glass fiber GF/B filter plates (Packard Bioscience/PerkinElmer, Boston, Mass.). The plate is measured by liquid scintillation counting with a TopCount® scintillation sounter (PerkinElmer). $IC_{50}$ determination is performed by fitting the curve of percent inhibition versus the log of the inhibitor concentration using GraphPad Prism® 5.0 software.

Pim pBAD Signaling Assays

KG-1A cells are purchased from ATCC (Manassas, Va.) and KMS.12.BM cells are purchased from NIBIO, JCRB cell bank (Tokyo, Japan) and maintained in the culture mediums recommended, RPMI, 10% FBS and IMDM 20% FBS (Mediatech, Manassas, Va.) respectively. To measure the pBAD inhibitory activity of the compounds, both cell lines are plated with the culture medium ($1 \times 10^6$/well/100 μL for KG1A and $4 \times 10^5$ cells/well/in 100 μL for KMS12BM) into 96-well V bottom polypropylene plates (Matrix, Thermo Fisher, USA) and incubated 30 min. at 37° C. to normalize cell signaling from handling. Test compounds are added at an appropriate concentration range and further incubated for 2.5 h for KMS.12.BM cells and 4 h for KG1-A cells. Plates are centrifuged at 2000 RPM for 10 min. and supernatants aspirated. 100 μL lysis buffer with protease inhibitors (Cell Signaling Technologies, Danver, Mass., Sigma, St Louis Mo., EMD, USA) is added to the pellets, mixed well and set on ice for 30 min. Lysates are frozen overnight at −80° C. To measure the pBAD activity, a Cell Signaling ELISA (enzyme-linked immunosorbent assay) kit (Cell Signaling Path Scan phosphor pBAD ELISA) is utilized. 50 μL of the lysate is tested per the ELISA protocol and the data analysis is performed by software on a SpectraMax® M5 plate reader (Molecular Devices, Sunnyvale, Calif.). $IC_{50}$ determination is performed by fitting the curve of percent inhibition versus the log of the inhibitor concentration using GraphPad Prism® 5.0 software.

Figure 1C:
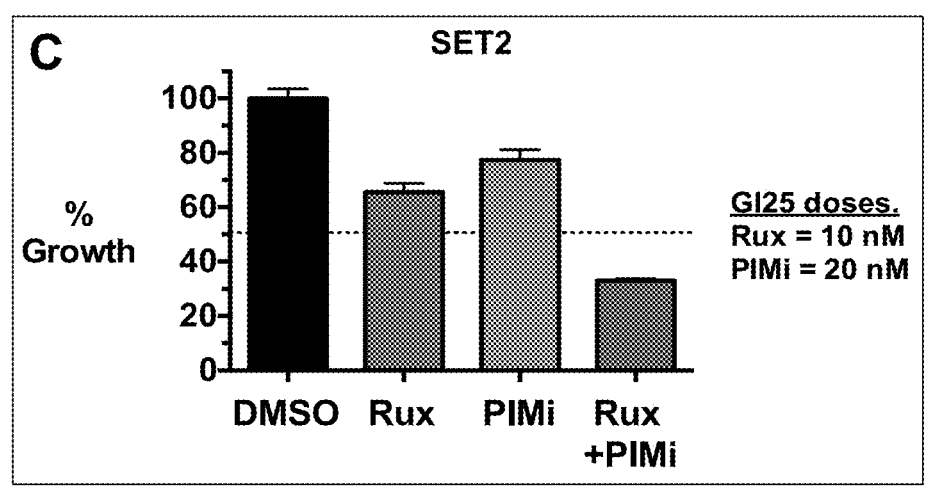
Figure 1A:
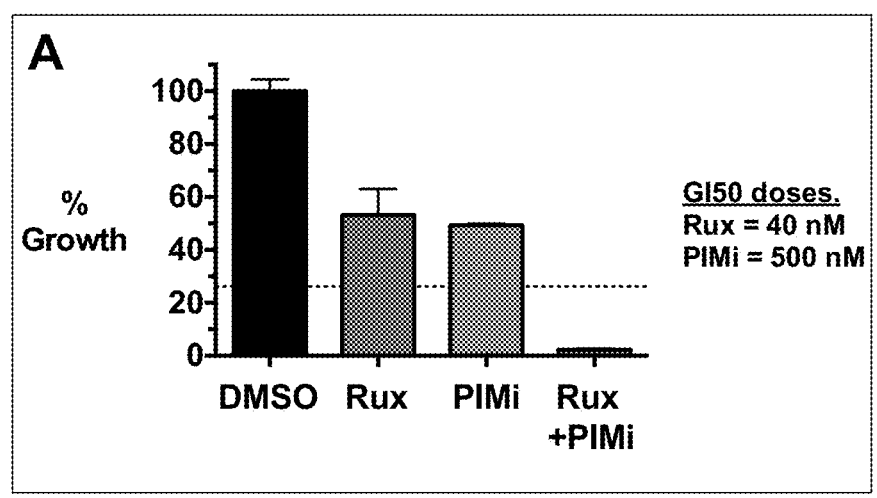

Example 1: The Pim Inhibitor, Compound 1, Synergizes with Ruxolitinib to Inhibit MPN Model Cell Growth BaF3/EpoR/JAK2-V617F, UKE1, and SET2 cells were either left untreated (DMSO-vehicle only), or treated with ruxolitinib (Rux) or Compound 1 (PIMi), and these two together (Rux+PIMi). Results for BaF3/EpoR/JAK2-V617F cells are shown in FIG. 1(A); results for UKE1 cells are shown in FIG. 1(B); and results for SET2 cells are shown in FIG. 1(C). Synergy studies were performed by CellTiter-Glo at 72 hr. Expected % growth of combinations using the Bliss independence model is indicated by the dotted line: the lower measured % growth suggests synergy.

Example 2: Compound 1 and Ruxolitinib Syngeristically Induce Apoptosis

UKE1 and SET2 cells were treated with either DMSO, ruxolitinib, Compound 1 (PIMi), or these two together. Cells were stained using FITC Annexin V and PI and analyzed by flow cytometry. Error bars indicate s.d. The p value was calculated by one-way ANOVA using Prism (GraphPad Software, Inc.). Result for UKE1 cells are shown in FIG. 2(A); and results for SET2 cells are shown in FIG. 2(B).

Figure 3:
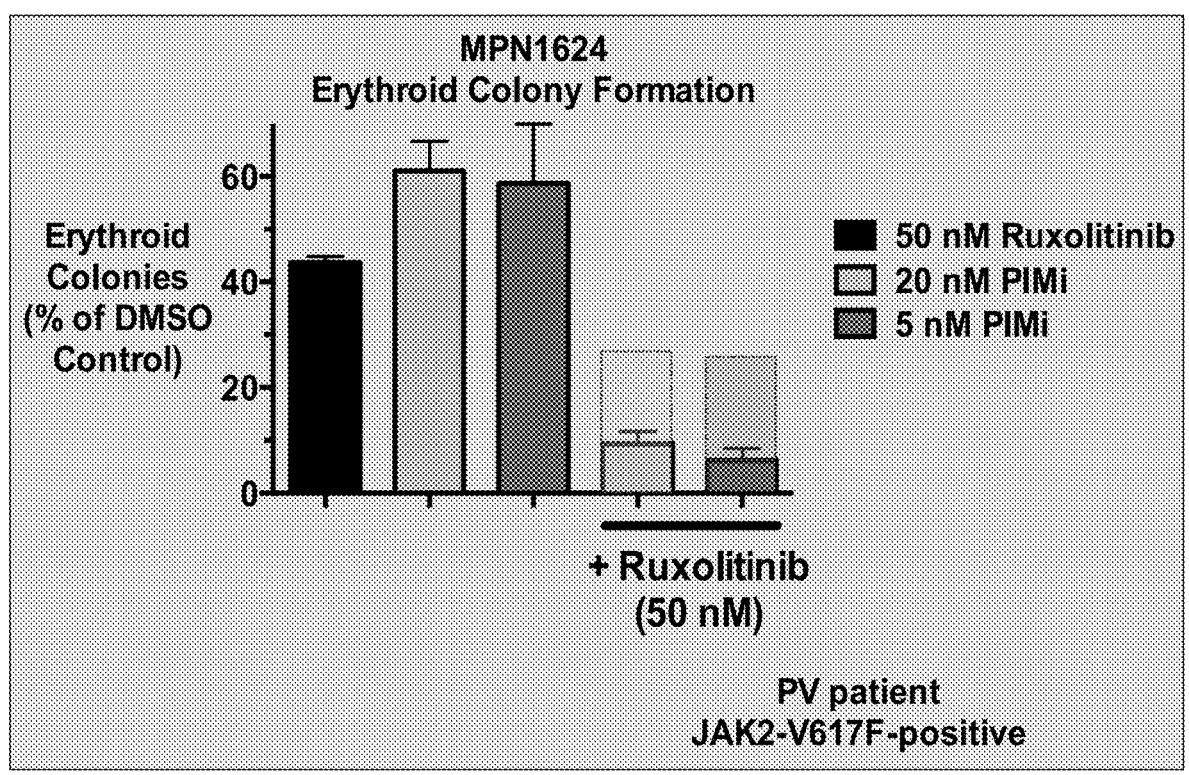
FIG. 3 depicts the % growth in peripheral blood mononuclear cells from an MPN patient (PV, JAK2-V617F+) in the presence of either DMSO-vehicle, 50 nM ruxolitinib (Rux), 20 nM or 5 nM Compound 1 (PIMi) or the two drugs in combination. Epo-independent erythroid colonies were scored after 12 days. Results are shown in FIG. 3. Expected % growth of combinations using the Bliss independence model is indicated by the transparent bars with dotted lines. The lower measured % growth indicates synergy.

Example 3: Inhibition of Neoplastic Erythroid Colony Formation of JAK2-V617F(+) MPN Hematopoietic Progenitors by Compound 1 and Synergistic Inhibition in Combination with Ruxolitinib at Very Low Doses of PIMi Peripheral blood mononuclear cells from an MPN patient (PV, JAK2-V617F+) were plated in methylcellulose containing cytokines without erythropoietin (Epo), and in the presence of either DMSO-vehicle, 50 nM ruxolitinib (Rux), 20 nM or 5 nM Compound 1 (PIMi) or the two drugs in combination. Epo-independent erythroid colonies were scored after 12 days. Results are shown in FIG. 3. Expected % growth of combinations using the Bliss independence model is indicated by the transparent bars with dotted lines. The lower measured % growth indicates synergy.

Figure 4:
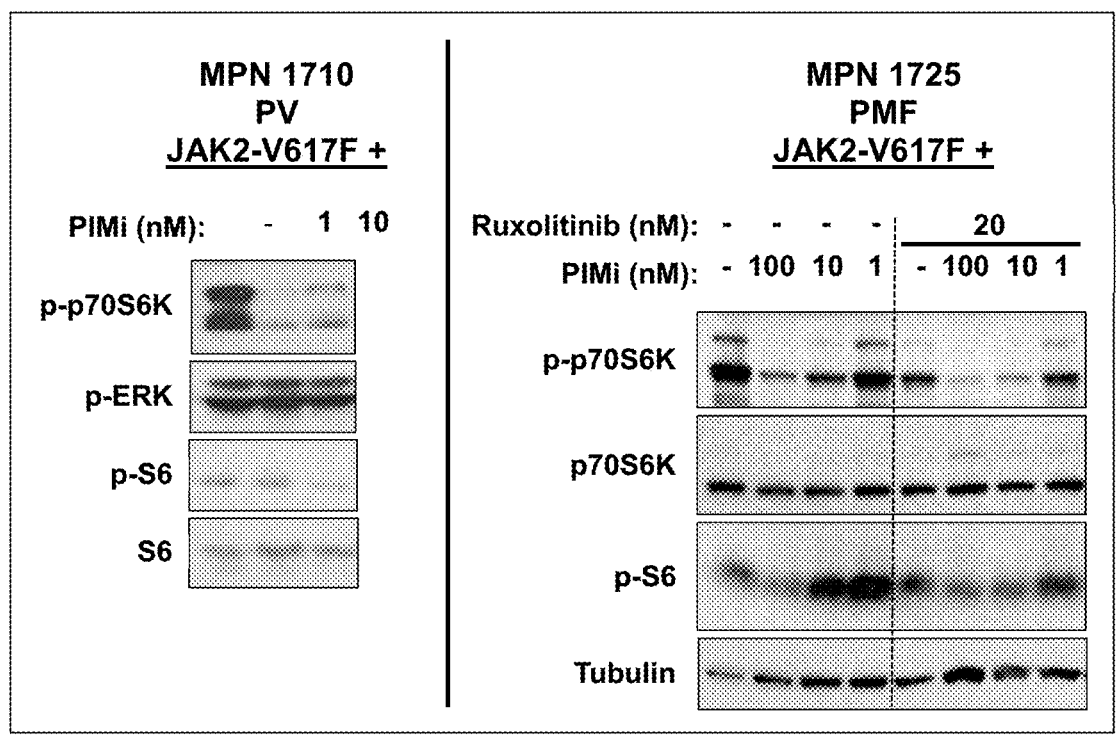
FIG. 4 depicts immunoblot analysis of MPN patient granulocytes left untreated (DMSO only) or treated with the indicated concentrations of Compound 1 (PIMi) or ruxolitinib.

Immunoblot analysis of MPN patient granulocytes left untreated (DMSO only) or treated with the indicated concentrations of Compound 1 (PIMi) or ruxolitinib. Results are shown in FIG. 4.

These results indicate that Compound 1 and ruxolitinib have a synergistic effect at 1 nM, 5 nM, and 20 nM Compound 1 is unexpected.

Example 4: Conversion of Synergistic Effects to Human Doses

Plasma samples from patients were incubated ex vivo with the KMS12BM cell line for 2.5 hours at 37° C. Whole cell lysates were prepared from the cells, and levels of pBAD were determined using an ELISA. Data presented are at 24 hours post dose (FIG. 5(A)) and in a time course (FIG. 5(B)), on cycle 1, day 8 for 80 mg BID of Compound 1 (average inhibition of 76%). The results in FIG. 5(A) indicate that the $IC_{50}$ at trough for Compound 1 is reached at 65 mg BID. In turn, Compound 1 has an $IC_{50}$ of 134 nM when BAD phosphorylation was measured in whole blood samples spiked with KMS-12-BM cells treated ex vivo with Compound 1. Hence, 65 mg BID of Compound 1 results in an $IC_{50}$ of 134 nM in this whole blood assay. As these results are in a whole blood assay unlike the assay in Example 3, an adjustment must be made for protein binding of Compound 1 in the whole blood assay.

Accordingly, the protein binding of Compound 1 was determined in human serum (in vitro) ranging from 0.3 µM-10 µM. Compound 1 exhibited high protein binding. For human, the average in vitro serum fraction unbound (fu) of 7.0%. For the protein binding determination, the Multi-Equilibrium Dialyzer System™ and diachema membranes from Harvard Apparatus (Holliston, Mass.) were utilized. Samples were protein precipitated, matrix matched and then centrifuged. The supernatant was transferred and analyzed using LC-MS/MS. The percent fraction unbound for in vitro samples was calculated using final peak area ratios in post-dialysis buffer divided by final peak area ratios in post-dialysis serum, with correction applied for volume shift.

The assay in Example 3 involved plating cells from blood in media. Due to the protein content in the media, the free fraction of Compound 1 in media is 58%. The serum free fraction and media free fractions of 7% and 58% can be used to convert the results in Example 3 to an human dose assuming a linear dose-response curve. This can be done by calculating the protein-binding adjusted activity as (cell activity*% free in media)/% free in serum—e.g., for cell activity of $IC_{50}$ of 1 nM, then (1 nM*58%)/7%=8.3 nM—an 8.3-fold shift in activity.

TABLE 1

| Cell activity - Example 3 | Protein-binding adjusted activity | Human dose BID | Daily human dose |
| --- | --- | --- | --- |
| 1 nM | 8.3 nM | 4 mg BID | 8 mg/day |
| 5 nM | 41 nM | 20 mg BID | 40 mg/day |
| 20 nM | 166 nM | 80 mg BID | 160 mg/day |

The 50 nM ruxolitinib in Example 3 corresponds a dose of ruxolinitb of about 15 mg BID. Generally, a dose of ruxolitinib in the 5-25 mg BID range would be expected to have synergistic effects.

Hence, the protein-binding adjusted activities of 41 nM and 8.3 nM correspond to $IC_{23}$ and $IC_{5.7}$ for Compound 1. It was unexpected that synergy with ruxolitinib was observed in MPN cells at such low doses of Compound 1—well below $IC_{50}$.

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:

1. A method of inhibiting or ameliorating a myeloproliferative neoplasm in a human patient in need thereof, comprising administering to said human patient a dose from about 2 mg/day to about 160 mg/day of N-{(7R)-4-[(3R,4R,5S)-3-amino-4-hydroxy-5-methylpiperidin-1-yl]-7-hydroxy-6, 7-dihydro-5H-cyclopenta[b]pyridin-3-yl}-6-(2,6-difluorophenyl)-5-fluoropyridine-2-carboxamide, or a pharmaceutically acceptable salt thereof, and about 10 mg/day to about 50 mg/day of ruxolitinib, or a pharmaceutically acceptable salt thereof.

2. The method of claim 1, wherein the ruxolitinib, or a pharmaceutically acceptable salt thereof, is ruxolitinib phosphate.

3. The method of claim 1, wherein the N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, is selected from the phosphoric acid salt, dihydrochloric acid salt, hydrochloric acid salt, maleic acid salt, adipic acid salt, hydrobromic acid salt, (R)-(–)-mandelic acid salt, salicylic acid salt, benzoic acid salt, benzenesulfonic acid salt, L-pyroglutamic acid salt, methanesulfonic acid salt, (1S)-(+)-10-camphorsulfonic acid salt, fumaric acid salt, sulfuric acid salt, L-tartaric acid salt, and D-tartaric acid salt of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide.

4. The method of claim 1, wherein the N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, is the phosphoric acid salt of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide.

5. The method of claim 1, wherein the dose of N-{(7R)-4-[(3R,4R, 5 S)-3-amino-4-hydroxy-5-methylpiperidin-1-yl]-7-hydroxy-6, 7-dihydro-5H-cyclopenta[b]pyridin-3-yl}-6-(2,6-difluorophenyl)-5-fluoropyridine-2-carboxamide, or a pharmaceutically acceptable salt thereof, is from about 5 mg/day to about 100 mg/day.

6. The method of claim 1, wherein the dose of N-{(7R)-4-[(3R,4R, 5 S)-3-amino-4-hydroxy-5-methylpiperidin-1-yl]-7-hydroxy-6, 7-dihydro-5H-cyclopenta[b]pyridin-3-yl}-6-(2,6-difluorophenyl)-5-fluoropyridine-2-carboxamide, or a pharmaceutically acceptable salt thereof, is from about 8 mg/day to about 80 mg/day.

7. The method of claim 1, wherein the dose of N-{(7R)-4-[(3R,4R, 5 S)-3-amino-4-hydroxy-5-methylpiperidin-1-yl]-7-hydroxy-6, 7-dihydro-5H-cyclopenta[b]pyridin-3-yl}-6-(2,6-difluorophenyl)-5-fluoropyridine-2-carboxamide, or a pharmaceutically acceptable salt thereof, is from about 8 mg/day to about 60 mg/day.

8. The method of claim 1, wherein the dose of N-{(7R)-4-[(3R,4R, 5 S)-3-amino-4-hydroxy-5-methylpiperidin-1-yl]-7-hydroxy-6, 7-dihydro-5H-cyclopenta[b]pyridin-3-yl}-6-(2,6-difluorophenyl)-5-fluoropyridine-2-carboxamide, or a pharmaceutically acceptable salt thereof, is from about 8 mg/day to about 50 mg/day.

9. The method of claim 1, wherein the dose of N-{(7R)-4-[(3R,4R, 5 S)-3-amino-4-hydroxy-5-methylpiperidin-1-yl]-7-hydroxy-6, 7-dihydro-5H-cyclopenta[b]pyridin-3-yl}-6-(2,6-difluorophenyl)-5-fluoropyridine-2-carboxamide, or a pharmaceutically acceptable salt thereof, is from about 8 mg/day to about 40 mg/day.

10. The method of claim 1, wherein the dose of N-{(7R)-4-[(3R,4R, 5 S)-3-amino-4-hydroxy-5-methylpiperidin-1-yl]-7-hydroxy-6, 7-dihydro-5H-cyclopenta[b]pyridin-3-yl}-6-(2,6-difluorophenyl)-5-fluoropyridine-2-carboxamide, or a pharmaceutically acceptable salt thereof, is from about 8 mg/day to about 20 mg/day.

11. The method of claim 1, wherein the dose of N-{(7R)-4-[(3R,4R,5 S)-3-amino-4-hydroxy-5-methylpiperidin-1-yl]-7-hydroxy-6, 7-dihydro-5H-cyclopenta[b]pyridin-3-yl}-6-(2,6-difluorophenyl)-5-fluoropyridine-2-carboxamide, or a pharmaceutically acceptable salt thereof, is from about 2 mg BID to about 50 mg BID.

12. The method of claim 1, wherein the dose of N-{(7R)-4-[(3R,4R, 5 S)-3-amino-4-hydroxy-5-methylpiperidin-1-yl]-7-hydroxy-6, 7-dihydro-5H-cyclopenta[b]pyridin-3-yl}-6-(2,6-difluorophenyl)-5-fluoropyridine-2-carboxamide, or a pharmaceutically acceptable salt thereof, is from about 4 mg BID to about 40 mg BID.

13. The method of claim 1, wherein the dose of N-{(7R)-4-[(3R,4R, 5 S)-3-amino-4-hydroxy-5-methylpiperidin-1-yl]-7-hydroxy-6, 7-dihydro-5H-cyclopenta[b]pyridin-3-yl}-6-(2,6-difluorophenyl)-5-fluoropyridine-2-carboxamide, or a pharmaceutically acceptable salt thereof, is from about 4 mg BID to about 30 mg BID.

14. The method of claim 1, wherein the dose of N-{(7R)-4-[(3R,4R, 5 S)-3-amino-4-hydroxy-5-methylpiperidin-1-yl]-7-hydroxy-6, 7-dihydro-5H-cyclopenta[b]pyridin-3-yl}-6-(2,6-difluorophenyl)-5-fluoropyridine-2-carboxamide, or a pharmaceutically acceptable salt thereof, is from about 4 mg BID to about 25 mg BID.

15. The method of claim 1, wherein the dose of N-{(7R)-4-[(3R,4R, 5 S)-3-amino-4-hydroxy-5-methylpiperidin-1-yl]-7-hydroxy-6, 7-dihydro-5H-cyclopenta[b]pyridin-3-yl}-6-(2,6-difluorophenyl)-5-fluoropyridine-2-carboxamide, or a pharmaceutically acceptable salt thereof, is from about 4 mg BID to about 20 mg BID.

16. The method of claim 1, wherein the dose of N-{(7R)-4-[(3R,4R, 5 S)-3-amino-4-hydroxy-5-methylpiperidin-1-yl]-7-hydroxy-6, 7-dihydro-5H-cyclopenta[b]pyridin-3-yl}-6-(2,6-difluorophenyl)-5-fluoropyridine-2-carboxamide, or a pharmaceutically acceptable salt thereof, is from about 4 mg BID to about 10 mg BID.

17. The method of claim 1, wherein the dose of ruxolitinib, or a pharmaceutically acceptable salt thereof, is about 10 mg/day to about 30 mg/day.

18. The method of claim 1, wherein the dose of ruxolitinib, or a pharmaceutically acceptable salt thereof, is about 10 mg/day.

19. The method of claim 1, wherein the dose of ruxolitinib, or a pharmaceutically acceptable salt thereof, is about 20 mg/day.

20. The method of claim 1, wherein the dose of ruxolitinib, or a pharmaceutically acceptable salt thereof, is about 30 mg/day.

21. The method of claim 1, wherein the dose of ruxolitinib, or a pharmaceutically acceptable salt thereof, is about 5 mg BID to about 25 mg BID.

22. The method of claim 1, wherein the dose of ruxolitinib, or a pharmaceutically acceptable salt thereof, is about 5 mg BID to about 15 mg BID.

23. The method of claim 1, wherein the dose of ruxolitinib, or a pharmaceutically acceptable salt thereof, is about 5 mg BID.

24. The method of claim 1, wherein the dose of ruxolitinib, or a pharmaceutically acceptable salt thereof, is about 10 mg BID.

25. The method of claim 1, wherein the dose of ruxolitinib, or a pharmaceutically acceptable salt thereof, is about 15 mg BID.

26. The method of claim 1, wherein the myeloproliferative neoplasm is selected from polycythemia vera (PV).

27. The method of claim 1, wherein the myeloproliferative neoplasm is selected from essential thrombocythemia (ET).

28. The method of claim 1, wherein the myeloproliferative neoplasm is selected from primary myelofibrosis.

29. The method of claim 1, wherein the myeloproliferative neoplasm is selected from chronic myelogenous leukemia (CIVIL).

30. The method of claim 1, wherein the myeloproliferative neoplasm is selected from chronic myelomonocytic leukemia (CMML).

31. The method of claim 1, wherein the myeloproliferative neoplasm is selected from hypereosinophilic syndrome (HES).

32. The method of claim 1, wherein the myeloproliferative neoplasm is selected from systemic mast cell disease (SMCD).

33. The method of claim 1, wherein the myeloproliferative neoplasm is selected from chronic neutrophilic leukemia (CNL).

34. The method of claim 1, wherein the myeloproliferative neoplasm is selected from chronic eosinophilic leukemia.

35. The method of claim 1, wherein the ruxolitinib, or pharmaceutically acceptable salt thereof, and the N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, are administered orally.

36. The method of claim 1, wherein the ruxolitinib, or a pharmaceutically acceptable salt thereof, is ruxolitinib phosphate and the N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, or a pharmaceutically acceptable salt thereof, is the phosphoric acid salt of N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide.

* * * * *

UNITED STATES PATENT AND TRADEMARK OFFICE
CERTIFICATE OF CORRECTION

PATENT NO. : 11,278,541 B2
APPLICATION NO. : 16/783663
DATED : March 22, 2022
INVENTOR(S) : Holly K. Koblish and Gary Reuther It is certified that error appears in the above-identified patent and that said Letters Patent is hereby corrected as shown below:

In the Claims

Column 16, Lines 61-64, Claim 1, delete "N-{(7R)-4-[(3R,4R,5S)-3-amino-4-hydroxy-5-methylpiperidin-1-yl]-7-hydroxy-6, 7-dihydro-5H-cyclopenta[b ]pyridin-3-yl }-6-(2,6-difluorophenyl)-5-fluoropyridine-2-carboxamide" and insert -- N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide --;

Column 17, Lines 28-31, Claim 5, delete "N-{ (7R)-4-[(3R,4R, 5 S)-3-amino-4-hydroxy-5-methylpiperidin-1-yl]-7-hydroxy-6, 7-dihydro-5H-cyclopenta[b ]pyridin-3-yl}-6-(2,6-difluorophenyl)-5-fluoropyridine-2-carboxamide" and insert -- N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide --;

Column 17, Lines 34-37, Claim 6, delete "N-{ (7R)-4-[(3R,4R, 5 S)-3-amino-4-hydroxy-5-methylpiperidin-1-yl]-7-hydroxy-6, 7-dihydro-5H-cyclopenta[b ]pyridin-3-yl}-6-(2,6-difluorophenyl)-5-fluoropyridine-2-carboxamide" and insert -- N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide --;

Column 17, Lines 40-43, Claim 7, delete "N-{ (7R)-4-[(3R,4R, 5 S)-3-amino-4-hydroxy-5-methylpiperidin-1-yl]-7-hydroxy-6, 7-dihydro-5H-cyclopenta[b ]pyridin-3-yl}-6-(2,6-difluorophenyl)-5-fluoropyridine-2-carboxamide" and insert -- N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide --;

Column 17, Lines 46-49, Claim 8, delete "N-{ (7R)-4-[(3R,4R, 5 S)-3-amino-4-hydroxy-5-methylpiperidin-1-yl]-7-hydroxy-6, 7-dihydro-5H-cyclopenta[b ]pyridin-3-yl}-6-(2,6-difluorophenyl)-5-fluoropyridine-2-carboxamide" and insert -- N-{(7R)-4-[(3R,4R,5S)-3-amino-4-hydroxy-5-

Signed and Sealed this
Twenty-fourth Day of May, 2022

Katherine Kelly Vidal
*Director of the United States Patent and Trademark Office* methylpiperidin-1-yl]-7-hydroxy-6,7-dihydro-5H-cyclopenta[b]pyridin-3-yl}-6-(2,6-difluorophenyl)-5-fluoropyridine-2-carboxamide --;

Column 17, Lines 52-55, Claim 9, delete "N-{ (7R)-4-[(3R,4R, 5 S)-3-amino-4-hydroxy-5-methylpiperidin-1-yl]-7-hydroxy-6, 7-dihydro-5H-cyclopenta[b ]pyridin-3-yl}-6-(2,6-difluorophenyl)-5-fluoropyridine-2-carboxamide" and insert -- N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide --;

Column 17, Lines 58-61, Claim 10, delete "N-{ (7R)-4-[(3R,4R, 5 S)-3-amino-4-hydroxy-5-methylpiperidin-1-yl]-7-hydroxy-6, 7-dihydro-5H-cyclopenta[b ]pyridin-3-yl}-6-(2,6-difluorophenyl)-5-fluoropyridine-2-carboxamide" and insert -- N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide --;

Column 17, Lines 64-67, Claim 11, delete "N-{(7R)-4-[ (3R,4R,5 S)-3-amino-4-hydroxy-5-methylpiperidin-1-yl]-7-hydroxy-6, 7-dihydro-5H-cyclopenta[b ]pyridin-3-yl}-6-(2,6-difluorophenyl)-5-fluoropyridine-2-carboxamide" and insert -- N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide --;

Column 18, Lines 3-6, Claim 12, delete "N-{(7R)-4-[(3R,4R, 5 S)-3-amino-4-hydroxy-5-methylpiperidin-1-yl]-7-hydroxy-6, 7-dihydro-5H-cyclopenta[b ]pyridin-3-yl }-6-(2,6-difluorophenyl)-5-fluoropyridine-2-carboxamide" and insert -- N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide --;

Column 18, Lines 9-12, Claim 13, delete "N-{(7R)-4-[(3R,4R, 5 S)-3-amino-4-hydroxy-5-methylpiperidin-1-yl]-7-hydroxy-6, 7-dihydro-5H-cyclopenta[b ]pyridin-3-yl }-6-(2,6-difluorophenyl)-5-fluoropyridine-2-carboxamide" and insert -- N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide --;

Column 18, Lines 16-19, Claim 14, delete "N-{(7R)-4-[(3R,4R, 5 S)-3-amino-4-hydroxy-5-methylpiperidin-1-yl]-7-hydroxy-6, 7-dihydro-5H-cyclopenta[b ]pyridin-3-yl }-6-(2,6-difluorophenyl)-5-fluoropyridine-2-carboxamide" and insert -- N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide --;

Column 18, Lines 22-25, Claim 15, delete "N-{(7R)-4-[(3R,4R, 5 S)-3-amino-4-hydroxy-5-methylpiperidin-1-yl]-7-hydroxy-6, 7-dihydro-5H-cyclopenta[b ]pyridin-3-yl }-6-(2,6-difluorophenyl)-5-fluoropyridine-2-carboxamide" and insert -- N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide --;

CERTIFICATE OF CORRECTION (continued)
U.S. Pat. No. 11,278,541 B2

Column 18, Lines 28-31, Claim 16, delete "N-{(7R)-4-[(3R,4R, 5 S)-3-amino-4-hydroxy-5-methylpiperidin-1-yl]-7-hydroxy-6, 7-dihydro-5H-cyclopenta[b ]pyridin-3-yl }-6-(2,6-difluorophenyl)-5-fluoropyridine-2-carboxamide" and insert -- N-{(7R)-4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide --.